US008999645B2

(12) United States Patent
Menon et al.

(10) Patent No.: US 8,999,645 B2
(45) Date of Patent: Apr. 7, 2015

(54) BIOREACTORS COMPRISING FUNGAL STRAINS

(75) Inventors: Suresh M. Menon, San Diego, CA (US); Samantha S. Orchard, San Diego, CA (US); Jessica Badger, San Diego, CA (US); David Lipson, San Diego, CA (US); Sara Guidi, San Diego, CA (US); David Newman, San Diego, CA (US)

(73) Assignee: Menon Renewable Products, Inc., San Diego, CA (US)

( * ) Notice: Subject to any disclaimer, the term of this patent is extended or adjusted under 35 U.S.C. 154(b) by 830 days.

(21) Appl. No.: 13/102,965

(22) Filed: May 6, 2011

(65) Prior Publication Data

US 2012/0058550 A1 Mar. 8, 2012

Related U.S. Application Data

(60) Provisional application No. 61/344,011, filed on May 7, 2010, provisional application No. 61/372,828, filed on Aug. 11, 2010, provisional application No. 61/411,860, filed on Nov. 9, 2010, provisional application No. 61/475,176, filed on Apr. 13, 2011.

(51) Int. Cl.

| | | |
|---|---|---|
| *C12Q 1/00* | (2006.01) | |
| *A23K 1/18* | (2006.01) | |
| *A23K 1/00* | (2006.01) | |
| *C11B 1/10* | (2006.01) | |
| *C11C 3/00* | (2006.01) | |
| *C12M 1/06* | (2006.01) | |
| *C12M 1/00* | (2006.01) | |
| *C12N 1/14* | (2006.01) | |
| *C12P 5/00* | (2006.01) | |
| *C12P 5/02* | (2006.01) | |
| *C12P 7/64* | (2006.01) | |
| *C12R 1/645* | (2006.01) | |
| *A01N 63/04* | (2006.01) | |
| *A23K 1/16* | (2006.01) | |
| *A23L 1/30* | (2006.01) | |

(52) U.S. Cl.
CPC .............. *A23K 1/1813* (2013.01); *A23K 1/007* (2013.01); *A23K 1/188* (2013.01); *C11B 1/10* (2013.01); *C11C 3/003* (2013.01); *C12M 27/02* (2013.01); *C12M 27/20* (2013.01); *C12N 1/14* (2013.01); *C12P 5/005* (2013.01); *C12P 5/02* (2013.01); *C12P 7/6463* (2013.01); *C12P 7/6481* (2013.01); *C12R 1/645* (2013.01); *C12P 2203/00* (2013.01); *A01N 63/04* (2013.01); *A23K 1/003* (2013.01); *A23K 1/1631* (2013.01); *A23K 1/1634* (2013.01); *A23K 1/164* (2013.01); *A23K 1/1826* (2013.01); *A23K 1/1853* (2013.01); *A23L 1/3008* (2013.01); *A23V 2002/00* (2013.01); *Y10S 426/805* (2013.01); *Y10S 426/807* (2013.01)

(58) Field of Classification Search
CPC ......................................................... C12Q 1/00
USPC ........................................................ 435/6.13
See application file for complete search history.

(56) References Cited

U.S. PATENT DOCUMENTS

| | | | |
|---|---|---|---|
| 4,870,011 A | 9/1989 | Suzuki et al. | |
| 5,952,020 A | 9/1999 | Lizak | |
| 6,258,964 B1 | 7/2001 | Nakajima et al. | |
| 6,441,208 B2 | 8/2002 | Bilj et al. | |
| 6,872,523 B1 * | 3/2005 | Iwen et al. .................... | 435/6.13 |
| 7,374,925 B2 | 5/2008 | Sabatier et al. | |
| 2006/0246563 A1 | 11/2006 | Eroma et al. | |
| 2007/0161095 A1 | 7/2007 | Gurin | |
| 2008/0057555 A1 | 3/2008 | Nguyen | |
| 2008/0086938 A1 | 4/2008 | Hazlebeck et al. | |
| 2008/0086939 A1 | 4/2008 | Dunlop et al. | |
| 2008/0124446 A1 | 5/2008 | Markels | |
| 2008/0160593 A1 | 7/2008 | Oyler | |
| 2009/0155873 A1 | 6/2009 | Kashiyama et al. | |
| 2009/0181440 A1 | 7/2009 | Rush | |

FOREIGN PATENT DOCUMENTS

| | | |
|---|---|---|
| EP | 0207475 | 1/1987 |
| WO | WO 2008/139641 | 11/2008 |
| WO | WO 2010/018105 | 2/2010 |

OTHER PUBLICATIONS

Chang Ji Zheng, et al., Vinaxanthone, a new FabI inhibitor from *Penicillium* sp. Journal of Antimicrobial Chemotherapy, 2009, vol. 63, No. 5, pp. 949-953.

Gincy Marina Mathew et al., "Progress in research on fungal cellulases for lignocellulose degradation" Journal of Scientific and Industrial Research, 2008, vol. 67. No. 11, pp. 898-907.

Howard et al., "Lignocellulose biotechnology: issues of bioconversion and enzyme production," Afican Journal of Biotechnology, 2003, vol. 2, No. 12, pp. 602-619.

Jorgensen, et al., "Production of cellulases and hemicellulases by three *Penicillium* species: effect of substrate and evaluation of cellulose absorption by capillary electrophoresis" *Enzyme and Microbial Tech.* (2005) 36: 42-48.

Li, et al., "Perspectives of microbial oils for biodiesel production" *Appl. Microbiol. Biotechnol.* (2008) 80: 749-756.

Lundquist, et al., "A Realistic Technology and Engineering Assessment of Algae Biofuel Production" Energy Biosciences Institute, University of California, Berkeley, California, Oct. 2010 (title page and i-153).

Meng, et al., "Biodiesel production from oleaginous microorganisms" *Renewable Energy* (2009) 34: 1-5.

(Continued)

*Primary Examiner* — Bin Shen

(74) *Attorney, Agent, or Firm* — Knobbe, Martens, Olson & Bear, LLP

(57) ABSTRACT

Disclosed herein are compositions comprising an isolated cellulose degrading fungus. Also disclosed are culture compositions and bioreactor compositions comprising the cellulose degrading fungus. Further described herein are filtration and extraction devices comprising the cellulose degrading fungus. Still further disclosed are bioprocessing facilities for and methods for producing co-products resulting from one or more bioprocesses of the cellulose degrading fungus.

20 Claims, 18 Drawing Sheets

(56) References Cited

OTHER PUBLICATIONS

Merdinger, E. & Devine, Jr. "Lipids of Debaryomyces Hansenii" *J. Bacteriol.* (1965) 89(6): 1488-1493.

Onyegeme-Okerenta et al., Online J. Health Allied Scs. 2009; 8(1):9.

Papanikolaou, et al., "Biotechnological valorization of raw glycerol discharged after bio-diesel (fatty acid methyl esters) manufacturing process: Production of 1,3-propanediol, citric acid and single cell oil" *Biomass and Bioenergy* (2008) 32: 60-70.

Peterson, et al., "*Penicillium pimiteouiense*: A New Species Isolated from Polycycstic Kidney Cell Cultures" *Mycologia* (1999) 91: 269-277.

Ragsdale, S.W., "Nickel-based Enzyme Systems" *J. Biol. Chem.* (2009) 284: 18571-18575.

Extended European Search Report dated May 16, 2012, issued in European Appl. No. 09819946.6.

International Search Report and Written Opinion dated May 3, 2010, issued in International Application No. PCT/US2009/060169.

International Search Report and Written Opinion dated Apr. 6, 2012, issued in International Application No. PCT/US2011/035644.

\* cited by examiner

5.8s rRNA

AAACTTTCAACAACGGATCTCTTGGTTCCGGCATCGATGAAGAACGCAGCGAAATGCGATAAGTAATGTGAATTG
CAGAATTCAGTGAATCATCGAGTCTTTGAACGCACATTGCGCCCCCTGGTATTCCGGGGGGCATGCCTGTCCGAGC
GTCATT       (SEQ ID NO: 1)

ITS1

AAGGATCATTACCGAGTGAGGGCCCTCTGGGTCCAACCTCCCACCCGTGTTTATCGTACCTTGTTGCTTCGGCGGG
CCCGCCGGCAAGGCCGCCGGGGGGCTTCCGTCCCCGGGTCCGCGCCCCGCCGAAGACACCTGTGAACGCTGTCTGAA
GATTGCAGTCTGAGCGAAAAGCTAAAATGTATTA  (SEQ ID NO: 2)

ITS2

GCTGCCCTCAAGCACGGCTTGTGTGTTGGGCCTCTCGTCCCTCCCGGGACGGGCCCGAAAGGCAGCGGCGGCACC
GCGTCCGGTCCTCGAGCGTATGGGGCTTCGTCACCCGCTCCGTAGGCCCGGCCGGCGCCCTGCCGGCACCATCAAT
CTTGTTTTTCCAGG       (SEQ ID NO: 3)

28s rRNA

TTGACCTCGGATCAGGTAGGGATACCCGCTGAACTTAAGCATATCAATAAGCGGAGGAAAAGAAACCAACAGGG
ATTGCCTCAGTAACGGCGAGTGAAGCGGCAAGAGCTCAAATTTGAAAGCTGGCTCCTTCGGGGTCCGCATTGTAA
TTTGCAGAGGATGCTTCGGGAGCGGCCCCATCTAAGTGCCCTGGAACGGGCCGTCATAGAGGGTGAGAATCCC
GTATGGGATGGGGTGCCCGCGACCATGTGAAGCTCCTTCGACGA      (SEQ ID NO: 4)

Complete internal transcribed spacer (ITS) 1, 5.8S rRNA gene, and ITS 2 and partial 28S rRNA gene nucleotide sequence (also includes 225 nucleotides 5' of ITS1):

5'-CTCTTCACGAGGATGCCTAGTAGGCACGAGTCATCAGCTCGTGCCGATTACGTCCCTGCCCTTTGTACACACCGC
CCGTCGCTACTACCGATTGAATGGCTCAGTGAGGCCTTCGGACTGGCTCAGGAGGGTTGGCAACGACCCCCCAGA
GCCGGAAAGTTGGTCAAACTCGGTCATTTAGAGGAAGTAAAAGTCGTAACAAGGTTTCCGTAGGTGAACCTGCGG
AAGGATCATTACCGAGTGAGGGCCCTCTGGGTCCAACCTCCCACCCGTGTTTATCGTACCTTGTTGCTTCGGCGGG
CCCGCCGGCAAGGCCGCCGGGGGGCTTCCGTCCCCGGGTCCGCGCCCCGCCGAAGACACCTGTGAACGCTGTCTGAA
GATTGCAGTCTGAGCGAAAAGCTAAAATGTATTAAAACTTTCAACAACGGATCTCTTGGTTCCGGCATCGATGAAG
AACGCAGCGAAATGCGATAAGTAATGTGAATTGCAGAATTCAGTGAATCATCGAGTCTTTGAACGCACATTGCGC
CCCCTGGTATTCCGGGGGGCATGCCTGTCCGAGCGTCATTGCTGCCCTCAAGCACGGCTTGTGTGTTGGGCCTCTC
GTCCCTCCCGGGACGGGCCCGAAAGGCAGCGGCGGCACCGCGTCCGGTCCTCGAGCGTATGGGGCTTCGTCACC
CGCTCCGTAGGCCCGGCCGGCGCCCTGCCGGCACCATCAATCTTGTTTTTCCAGGTTGACCTCGGATCAGGTAGGGA
TACCCGCTGAACTTAAGCATATCAATAAGCGGAGGAAAAGAAACCAACAGGGATTGCCTCAGTAACGGCGAGTG
AAGCGGCAAGAGCTCAAATTTGAAAGCTGGCTCCTTCGGGGTCCGCATTGTAATTTGCAGAGGATGCTTCGGGAG
CGGCCCCATCTAAGTGCCCTGGAACGGGCCGTCATAGAGGGTGAGAATCCCGTATGGGATGGGGTGCCCGCGA
CCATGTGAAGCTCCTTCGACGAG-3'  (SEQ ID NO: 5)

FIG. 14

SEQUENCE LISTING

```
<160> NUMBER OF SEQ ID NOS: 5

<210> SEQ ID NO 1
<211> LENGTH: 157
<212> TYPE: DNA
<213> ORGANISM: Penicillium menonorum

<400> SEQUENCE: 1
aaactttcaa caacggatct cttggttccg gcatcgatga agaacgcagc gaaatgcgat      60
aagtaatgtg aattgcagaa ttcagtgaat catcgagtct ttgaacgcac attgcgcccc    120
ctggtattcc gggggcatg cctgtccgag cgtcatt                             157

<210> SEQ ID NO 2
<211> LENGTH: 185
<212> TYPE: DNA
```

<213> ORGANISM: Penicillium menonorum

<400> SEQUENCE: 2

```
aaggatcatt accgagtgag ggccctctgg gtccaacctc ccacccgtgt ttatcgtacc    60
ttgttgcttc ggcgggcccg ccgcaaggcc gccgggggc ttccgtcccc gggtccgcgc   120
ccgccgaaga cacctgtgaa cgctgtctga agattgcagt ctgagcgaaa agctaaaatg   180
tatta                                                              185
```

<210> SEQ ID NO 3
<211> LENGTH: 164
<212> TYPE: DNA
<213> ORGANISM: Penicillium menonorum

<400> SEQUENCE: 3

```
gctgccctca agcacggctt gtgtgttggg cctctcgtcc ctcccgggac gggcccgaaa    60
ggcagcggcg gcaccgcgtc cggtcctcga gcgtatgggg cttcgtcacc cgctccgtag   120
gcccggccgg cgcctgccgg caccatcaat cttgttttc cagg                     164
```

<210> SEQ ID NO 4
<211> LENGTH: 267
<212> TYPE: DNA
<213> ORGANISM: Penicillium menonorum

<400> SEQUENCE: 4

```
ttgacctcgg atcaggtagg gatacccgct gaacttaagc atatcaataa gcggaggaaa    60
agaaaccaac agggattgcc tcagtaacgg cgagtgaagc ggcaagagct caaatttgaa   120
agctggctcc ttcggggtcc gcattgtaat ttgcagagga tgcttcggga gcggccccca   180
tctaagtgcc ctggaacggg ccgtcataga gggtgagaat cccgtatggg atggggtgcc   240
cgcgaccatg tgaagctcct tcgacga                                      267
```

<210> SEQ ID NO 5
<211> LENGTH: 999
<212> TYPE: DNA
<213> ORGANISM: Penicillium menonorum

<400> SEQUENCE: 5

```
ctcttcacga ggatgcctag taggcacgag tcatcagctc gtgccgatta cgtccctgcc    60
ctttgtacac accgcccgtc gctactaccg attgaatggc tcagtgaggc cttcggactg   120
gctcaggagg gttggcaacg acccccaga gccggaaagt tggtcaaact cggtcattta   180
gaggaagtaa aagtcgtaac aaggtttccg taggtgaacc tgcggaagga tcattaccga   240
gtgagggccc tctgggtcca acctccacc cgtgtttatc gtaccttgtt gcttcggcgg   300
gcccgccgca aggccgccgg ggggcttccg tccccgggtc cgcgcccgcc gaagacacct   360
gtgaacgctg tctgaagatt gcagtctgag cgaaaagcta aaatgtatta aaactttcaa   420
caacggatct cttggttccg gcatcgatga agaacgcagc gaaatgcgat aagtaatgtg   480
aattgcagaa ttcagtgaat catcgagtct ttgaacgcac attgcgcccc ctggtattcc   540
gggggcatg cctgtccgag cgtcattgct gccctcaagc acggcttgtg tgttgggcct   600
ctcgtccctc ccgggacggg cccgaaaggc agcggcggca ccgcgtccgg tcctcgagcg   660
tatgggcttt cgtcacccgc tccgtaggcc cggccgcgc ctgccggcac catcaatctt   720
gttttccag gttgacctcg gatcaggtag ggatacccgc tgaacttaag catatcaata   780
agcggaggaa aagaaaccaa cagggattgc ctcagtaacg gcgagtgaag cggcaagagc   840
```

```
tcaaatttga aagctggctc cttcggggtc cgcattgtaa tttgcagagg atgcttcggg    900
agcggccccc atctaagtgc cctggaacgg gccgtcatag agggtgagaa tcccgtatgg    960
gatggggtgc ccgcgaccat gtgaagctcc ttcgacgag                           999
```

BIOREACTORS COMPRISING FUNGAL STRAINS

CROSS-REFERENCE TO RELATED APPLICATIONS

This application is a nonprovisional application of and claims priority to U.S. Provisional Application No. 61/344,011, filed May 7, 2010; U.S. Provisional Application No. 61/372,828, filed Aug. 11, 2010; U.S. Provisional Application No. 61/411,860, filed Nov. 9, 2010; and U.S. Provisional Application No. 61/475,176, filed Apr. 13, 2011, each of which is incorporated herein by reference in its entirety.

SEQUENCE LISTING

The present application is being filed along with a Sequence Listing in electronic format. The Sequence Listing is provided as a file entitled MENON001A.TXT, created May 4, 2011, which is 3.1 Kb in size. The information in the electronic format of the Sequence Listing is incorporated herein by reference in its entirety.

FIELD OF THE INVENTION

The present application generally relates to the use of microbial and chemical systems to convert biomass to commodity chemicals, such as biofuels/biopetrols.

BACKGROUND

Petroleum is facing declining global reserves and contributes to more than 30% of greenhouse gas emissions driving global warming. Annually 800 billion barrels of transportation fuel are consumed globally. Diesel and jet fuels account for greater than 50% of global transportation fuels.

Significant legislation has been passed, requiring fuel producers to cap or reduce the carbon emissions from the production and use of transportation fuels. Fuel producers are seeking substantially similar, low net carbon fuels that can be blended and distributed through existing infrastructure (e.g., refineries, pipelines, tankers).

Due to increasing petroleum costs and reliance on petrochemical feedstocks, the chemicals industry is also looking for ways to improve margin and price stability, while reducing its environmental footprint. The chemicals industry is striving to develop greener products that are more energy, water, and $CO_2$ efficient than current products. Fuels produced from biological sources, such as biomass, represent one aspect of the process.

SUMMARY OF THE INVENTION

A system and method are provided which utilize microbes to convert biomass feedstock into fuel. In one aspect of the invention, a method of producing aromatic compounds, animal feed, and lipids includes receiving a feedstock including biological matter; separating the feedstock into a liquid phase feedstock and a solid phase feedstock; adding water and nutrients to the solid phase feedstock, thereby producing a liquid culture; inoculating the liquid culture with one or more microbes capable of converting the solid phase feedstock into aromatic compounds and lipids, the inoculated liquid culture yielding microbial biomass; providing suitable conditions for the microbes to convert the solid phase feedstock to aromatic compounds and lipids; and extracting produced aromatic compounds and lipids. Lipids are chemically converted to alkanes and related hydrocarbons for fuel, or alternatively are transesterified to produce biodiesel, both using processes known in the art.

In some aspects, the liquid feedstock and the solid feedstock are not separated prior to inoculation of the culture. In some aspects, the solid phase feedstock is pretreated to release cellulosic and/or hemicellulosic breakdown products, such as oligosaccharides, into the liquid medium. In other embodiments, the solid phase feedstock need not be pretreated.

In another aspect of the invention, the liquid phase feedstock, representing hydrolyzates of the cellulosic and/or hemicellulosic portions of the biological matter, is inoculated with microbes capable of converting the hydrolyzates into lipids. Lipids are chemically converted to alkanes and related hydrocarbons for fuel, or alternatively are transesterified to produce biodiesel, both using processes known in the art.

In another aspect of the invention, a system for producing fuel components includes a bioreactor having an inoculated liquid culture including microbes and biomass; and a controller in communication with the bioreactor, the controller providing operating instructions to the bioreactor; and where the bioreactor yields the fuel components.

In yet another aspect of the invention, a method of producing aromatic compounds, animal feed, and lipids includes receiving a feedstock including biological matter; adding water and nutrients to the feedstock; inoculating the feedstock with microbes capable of converting a portion of the feedstock into aromatic compounds and lipids; providing suitable conditions for the microbes to convert a portion of the feedstock to aromatic compounds and lipids; and extracting produced aromatic compounds and lipids.

Also described herein are compositions and processes that comprise or otherwise utilize a cellulose degrading fungus of the genus *Penicillium*.

Some aspects of the compositions described herein relate to an isolated cellulose degrading fungus of the genus *Penicillium*. In some such aspects, the isolated cellulose degrading fungus of the genus *Penicillium* comprises a fungus that is the same species as the fungus having NRRL deposit Accession No: 50410. In other aspects, the isolated cellulose degrading fungus of the genus *Penicillium* comprises an isolated fungus comprising a 5.8S ribosomal RNA gene sequence having at least 98% nucleotide sequencing identity with the nucleic acid of SEQ ID NO: 1. In still another aspect, the isolated cellulose degrading fungus of the genus Penicillium further comprises an ITS1 sequence with at least 98% sequence identity to SEQ ID NO: 2. In yet another aspect, the isolated cellulose degrading fungus of the genus *Penicillium* further comprises an ITS2 sequence with at least 98% sequence identity to SEQ ID NO: 3. In still another aspect, the isolated cellulose degrading fungus of the genus *Penicillium* further comprises a 28S ribosomal RNA gene sequence with at least 98% sequence identity to SEQ ID NO: 4. In yet another aspect, the isolated cellulose degrading fungus of the genus *Penicillium* comprises *Penicillium menonorum*.

Also described herein is a living, in vitro culture of a cellulose degrading fungus of the genus *Penicillium* comprising a nutrient medium, wherein the fungus is growing on the medium. In certain aspects, the medium is a solid medium. In other aspects, the medium is a liquid medium. In certain aspects, the medium comprises a carbon source and a nitrogen source, wherein the ratio of carbon to nitrogen in the medium ranges from about 1:1 to about 1000:1. In other aspects, the ratio of carbon to nitrogen in the medium ranges from about 20:1 to about 100:1. In still other aspects, the ratio of carbon to nitrogen in the medium is greater than about 100:1.

In some aspects, the carbon source comprises one or more simple sugars. In one such aspect, the carbon source comprises cane juice and/or its condensates including, but not limited to, dry solid obtained by complete evaporation.

In other aspects, the carbon source comprises a cellulosic carbon source or a lysate thereof. In a preferred aspect, the cellulosic carbon source comprises a hydrolysate of a cellulosic carbon. In certain aspects, the carbon source comprises or is derived from a material selected from the group consisting of grains, stover, forage, grasses, oilseed crops, nut shells, nut hulls, fruit pomace, plant waste, algae, wood, wood byproducts, bark, paper, paper products, animal manure and food waste. In preferred aspects, the carbon source comprises or is derived from a material selected from the group consisting of stover of grains, stover of oilseed crops, almond hulls, grape pomace, agriculture waste, yard waste, wood chips, sawdust, the manure of herbivorous animals and food waste of plant origin. In other aspects, the cellulosic carbon source comprises a lignocellulosic carbon source or a lysate thereof. In still other aspects, the cellulosic carbon source comprises a hemicellulosic carbon source or a lysate thereof.

Also described herein is a bioprocess reactor or bioreactor comprising a cellulose degrading fungus of the genus *Penicillium* growing in a liquid medium, wherein the fungus comprises at least 5% triacylglyceride ("TAG") by weight. In a preferred aspect, the weight is dry weight. In some aspects, the cellulose degrading fungus of the genus *Penicillium* comprises at least about 10% to about 50% triacylglyceride by dry weight. In a preferred aspect, the cellulose degrading fungus of the genus *Penicillium* comprises at least about 25% to about 50% triacylglyceride by dry weight. In some aspects, the liquid method comprises a carbon source.

In some aspects, the carbon source comprises one or more simple sugars. In one such aspect, the carbon source comprises cane juice and/or its condensates including, but not limited to, dry solid obtained by complete evaporation.

In other aspects, the carbon source comprises a cellulosic carbon source or a lysate thereof. In a preferred aspect, the cellulosic carbon source comprises a hydrolysate of a cellulosic carbon. In certain aspects, the carbon source comprises or is derived from a material selected from the group consisting of grains, stover, forage, grasses, oilseed crops, nut shells, nut hulls, fruit pomace, plant waste, algae, wood, wood byproducts, bark, paper, paper products, animal manure and food waste. In preferred aspects, the carbon source comprises or is derived from a material selected from the group consisting of stover of grains, stover of oilseed crops, almond hulls, grape pomace, agriculture waste, yard waste, wood chips, sawdust, the manure of herbivorous animals and food waste of plant origin. In other aspects, the cellulosic carbon source comprises a lignocellulosic carbon source or a lysate thereof. In still other aspects, the cellulosic carbon source comprises a hemicellulosic carbon source or a lysate thereof.

Also described herein is a bioprocess reactor or bioreactor comprising a cellulose degrading fungus of the genus *Penicillium* growing in a liquid medium, wherein the liquid medium comprises a carbon source and a nitrogen source. In some aspects, the ratio of carbon to nitrogen in the medium ranges from about 1:1 to about 1000:1. In some aspects, the ratio of carbon to nitrogen in the medium ranges from about 20:1 to about 100:1. In some aspects, the ratio of carbon to nitrogen in the medium is greater than about 100:1.

In some aspects, the carbon source comprises one or more simple sugars. In one such aspect, the carbon source comprises cane juice and/or its condensates including, but not limited to, dry solid obtained by complete evaporation.

In other aspects, the carbon source comprises a cellulosic carbon source or a lysate thereof. In a preferred aspect, the cellulosic carbon source comprises a hydrolysate of a cellulosic carbon. In certain aspects, the carbon source comprises or is derived from a material selected from the group consisting of grains, stover, forage, grasses, oilseed crops, nut shells, nut hulls, fruit pomace, plant waste, algae, wood, wood byproducts, bark, paper, paper products, animal manure and food waste. In preferred aspects, the carbon source comprises or is derived from a material selected from the group consisting of stover of grains, stover of oilseed crops, almond hulls, grape pomace, agriculture waste, yard waste, wood chips, sawdust, the manure of herbivorous animals and food waste of plant origin. In other aspects, the cellulosic carbon source comprises a lignocellulosic carbon source or a lysate thereof. In still other aspects, the cellulosic carbon source comprises a hemicellulosic carbon source or a lysate thereof.

In certain aspects, the liquid medium comprises dissolved oxygen in a range of about 0.1 mg/L to about 100 mg/L. In certain aspects, the dissolved oxygen is in a range of about 0.5 mg/L to about 40 mg/L.

Also described herein is a bioprocess reactor or bioreactor comprising a cellulosic carbon source having a cellulose degrading fungus of the genus *Penicillium* growing thereon, said cellulosic carbon source or a lysate thereof present in a liquid medium.

In other aspects, the carbon source comprises a cellulosic carbon source or a lysate thereof. In a preferred aspect, the cellulosic carbon source comprises a hydrolysate of a cellulosic carbon. In certain aspects, the carbon source comprises or is derived from a material selected from the group consisting of grains, stover, forage, grasses, oilseed crops, nut shells, nut hulls, fruit pomace, plant waste, algae, wood, wood byproducts, bark, paper, paper products, animal manure and food waste. In preferred aspects, the carbon source comprises or is derived from a material selected from the group consisting of stover of grains, stover of oilseed crops, almond hulls, grape pomace, agriculture waste, yard waste, wood chips, sawdust, the manure of herbivorous animals and food waste of plant origin. In other aspects, the cellulosic carbon source comprises a lignocellulosic carbon source or a lysate thereof. In still other aspects, the cellulosic carbon source comprises a hemicellulosic carbon source or a lysate thereof.

Also described herein is a bioprocess reactor or bioreactor comprising a cellulose degrading fungus of the genus *Penicillium* growing in a liquid medium, said liquid medium comprising at least one lipid selected from the group consisting of triacylglyceride and phospholipids. In some aspects, the liquid medium comprises a carbon source and a nitrogen source, wherein the ratio of carbon to nitrogen in the medium ranges from about 1:1 to about 1000:1. In some aspects, the ratio of carbon to nitrogen in the medium ranges from about 20:1 to about 100:1. In some aspects, the ratio of carbon to nitrogen in the medium is greater than about 100:1.

In some aspects, the carbon source comprises one or more simple sugars. In one such aspect, the carbon source comprises cane juice and/or its condensates including, but not limited to, dry solid obtained by complete evaporation.

In other aspects, the carbon source comprises a cellulosic carbon source or a lysate thereof. In a preferred aspect, the cellulosic carbon source comprises a hydrolysate of a cellulosic carbon. In certain aspects, the carbon source comprises or is derived from a material selected from the group consisting of grains, stover, forage, grasses, oilseed crops, nut shells, nut hulls, fruit pomace, plant waste, algae, wood, wood byproducts, bark, paper, paper products, animal manure and food waste. In preferred aspects, the carbon source comprises or is derived from a material selected from the group consisting of stover of grains, stover of oilseed crops, almond hulls, grape pomace, agriculture waste, yard waste, wood chips, sawdust, the manure of herbivorous animals and food waste of plant origin. In other aspects, the cellulosic carbon source comprises a lignocellulosic carbon source or a lysate thereof. In still other aspects, the cellulosic carbon source comprises a hemicellulosic carbon source or a lysate thereof.

In some aspects, the bioprocess reactor and bioreactor compositions described above can further comprise an impeller rotating at a stir rate of about 1 RPM to about 1200 RPM. In some aspects the stir rate can be about 1 RPM to about 300 RPM. In some aspects the stir rate can be about 20 to about 100 RPM. In other aspects, the stir rate can be about 60-70 RPM.

Also described herein is a fungal culture in a vessel, wherein the culture comprises a liquid medium comprising a cellulose degrading fungus of the genus *Penicillium* in growth phase, a carbon source, a non-carbon nutrient mix, and $MgSO_4$ and/or other salt(s) of Mg at a concentration of at least 0.5 mM. In certain aspects, the culture is approximately 0, 12, 24, 48, 72, 96, 120, 144, 168, 192, 216, 240 or greater than 240 hours old. In some aspects, the ratio of carbon to nitrogen in the medium ranges from about 1:1 to about 1000:1. In some aspects, the ratio of carbon to nitrogen in the medium ranges from about 20:1 to about 100:1. In some aspects, the ratio of carbon to nitrogen in the medium is greater than about 100:1.

In some aspects, the carbon source comprises one or more simple sugars. In one such aspect, the carbon source comprises cane juice and/or its condensates including, but not limited to, dry solid obtained by complete evaporation.

In other aspects, the carbon source comprises a cellulosic carbon source or a lysate thereof. In a preferred aspect, the cellulosic carbon source comprises a hydrolysate of a cellulosic carbon. In certain aspects, the carbon source comprises or is derived from a material selected from the group consisting of grains, stover, forage, grasses, oilseed crops, nut shells, nut hulls, fruit pomace, plant waste, algae, wood, wood byproducts, bark, paper, paper products, animal manure and food waste. In preferred aspects, the carbon source comprises or is derived from a material selected from the group consisting of stover of grains, stover of oilseed crops, almond hulls, grape pomace, agriculture waste, yard waste, wood chips, sawdust, the manure of herbivorous animals and food waste of plant origin. In other aspects, the cellulosic carbon source comprises a lignocellulosic carbon source or a lysate thereof. In still other aspects, the cellulosic carbon source comprises a hemicellulosic carbon source or a lysate thereof.

Also described herein is a filtration apparatus comprising a filter housing with a filtration surface disposed therein, and a mycelial mat of a cellulose degrading fungus of the genus *Penicillium* dispersed on said filtration surface. In some aspects, the mycelial mat comprises a moisture content of less than about 50% w/w. In other aspects, the mycelial mat comprises a moisture content of less than about 25% w/w. In still other aspects, the mycelial mat comprises a moisture content of less than about 15% w/w. In yet other aspects, the mycelial mat comprises a moisture content of less than about 5% w/w.

Also described herein is an extraction apparatus comprising a vessel comprising a solvent and a fungus, wherein the solvent is in contact with the fungus. In a preferred embodiment, the extraction apparatus comprises hyphal filaments and/or other tissues or cellular components of a cellulose degrading fungus of the genus *Penicillium* dispersed in an aprotic solvent.

Also described herein is an extraction apparatus comprising a vessel comprising a solvent and a fungus, wherein the solvent is in contact with the fungus. In a preferred embodiment, the extraction apparatus comprises hyphal filaments and/or other tissues or cellular components of a cellulose degrading fungus of the genus *Penicillium* dispersed in a solvent comprising less than 80% water. In some aspects, the solvent comprises at least one aliphatic solvent. In certain aspects, the solvent comprises at least one polar solvent. In certain aspects, the polar solvent is aprotic. In a preferred aspect, the solvent comprises hexane and ethanol. In some aspects, the ethanol is at a concentration of about 5-25%. In some aspects, the ethanol is at a concentration of about 10-20%.

Also described herein is a bioprocessing facility for producing co-products, the facility comprising a plurality of bioprocess reactors comprising: a cellulose degrading fungus of the genus *Penicillium* growing in a liquid medium. In some aspects, the liquid medium comprises a carbon source and a nitrogen source, wherein the ratio of carbon to nitrogen in the medium ranges from about 1:1 to about 1000:1. In some aspects, the ratio of carbon to nitrogen in the medium ranges from about 20:1 to about 100:1. In some aspects, the ratio of carbon to nitrogen in the medium is greater than about 100:1.

In some aspects, the cellulose degrading fungus of the genus *Penicillium* comprises at least 5% triacylglyceride by weight. In a preferred aspect, the weight is dry weight. In some aspects, the cellulose degrading fungus of the genus *Penicillium* comprises at least about 10% to about 50% triacylglyceride by dry weight. In a preferred aspect, the cellulose degrading fungus of the genus *Penicillium* comprises at least about 25% to about 50% triacylglyceride by dry weight.

In some aspects, the carbon source comprises one or more simple sugars. In one such aspect, the carbon source comprises cane juice and/or its condensates including, but not limited to, dry solid obtained by complete evaporation.

In other aspects, the carbon source comprises a cellulosic carbon source or a lysate thereof. In a preferred aspect, the cellulosic carbon source comprises a hydrolysate of a cellulosic carbon. In certain aspects, the carbon source comprises or is derived from a material selected from the group consisting of grains, stover, forage, grasses, oilseed crops, nut shells, nut hulls, fruit pomace, plant waste, algae, wood, wood byproducts, bark, paper, paper products, animal manure and food waste. In preferred aspects, the carbon source comprises or is derived from a material selected from the group consisting of stover of grains, stover of oilseed crops, almond hulls, grape pomace, agriculture waste, yard waste, wood chips, sawdust, the manure of herbivorous animals and food waste of plant origin. In other aspects, the cellulosic carbon source comprises a lignocellulosic carbon source or a lysate thereof. In still other aspects, the cellulosic carbon source comprises a hemicellulosic carbon source or a lysate thereof.

In some aspects of the above-described bioprocessing facilities, one or more bioprocess reactors can further comprise an impeller rotating at a stir rate of about 1 RPM to about 1200 RPM. In some aspects the stir rate can be about 1 RPM to about 300 RPM. In some aspects the stir rate can be about 20 to about 100 RPM. In other aspects, the stir rate can be about 60-70 RPM.

Also described herein is a process for manufacturing a plurality of co-products, the process comprising: a) inoculating a bioprocess reactor with an inoculum of a cellulose degrading fungus of the genus *Penicillium*; b) allowing a sufficient time for production of TAG by said fungus, wherein said TAG comprises at least 5% of the dry weight of the fungus; c) harvesting said fungus; d) extracting lipids from said fungus, thereby producing a lipid co-product. The process can further comprise e) drying said fungus, thereby producing a feed co-product. In some aspects, the TAG comprises at least 35% of the dry weight of the fungus. In other aspects, the lipid co-product comprises a TAG co-product and a phospholipid co-product. In still other aspects, the phospholipid co-product comprises lecithin. In yet other aspects, the feed co-product is suitable for animal and/or human consumption. In certain preferred aspects, the fungus comprises *Penicillium menonorum*. In preferred aspects, the fungus comprises a species being the same as NRRL deposit Accession No: 50410.

Also described herein is a process for producing a harvested fungus and a conditioned liquid medium, the process comprising: a) incubating a cellulose degrading fungus of the genus *Penicillium* in a liquid medium for a sufficient time for production of TAG by said fungus; and b) separating said fungus from said liquid medium, thereby producing a harvested fungus and a conditioned liquid medium. In some aspects, the liquid medium comprises a carbon source and a nitrogen source, wherein the ratio of carbon to nitrogen in the medium ranges from about 1:1 to about 1000:1. In some aspects, the ratio of carbon to nitrogen in the medium ranges from about 20:1 to about 100:1. In some aspects, the ratio of carbon to nitrogen in the medium is greater than about 100:1. In certain aspects, the TAG content in said harvested fungus comprises at least 5% of the dry weight of the fungus. In some aspects, the TAG comprises at least 10%, 15%, 20%, 25%, 30%, 35%, 40%, 45%, or at least 50% of the dry weight of the fungus. In certain aspects, the harvested fungus comprises an enriched Fe content. In some aspects, the harvested fungus comprises an enriched Ni content. In some aspects, the harvested fungus comprises an enriched malic acid content. In some aspects, the harvested fungus comprises an enriched content of one or more amino acids selected from the group consisting of: L-isoleucine, L-tryptophan, and L-serine. In certain preferred aspects, the cellulose degrading fungus comprises *Penicillium menonorum*. In preferred aspects, the fungus comprises a species being the same as NRRL deposit Accession No: 50410.

Also described herein is a conditioned liquid medium produced by the process described hereinabove. In certain aspects, the conditioned liquid medium comprises a carbon source and a nitrogen source, wherein the ratio of carbon to nitrogen in the medium ranges from about 1:1 to about 1000:1. In some aspects, the ratio of carbon to nitrogen in the medium ranges from about 20:1 to about 100:1. In some aspects, the ratio of carbon to nitrogen in the medium is greater than about 100:1. In certain preferred aspects, the conditioned liquid medium has been conditioned by a cellulose degrading fungus comprises *Penicillium menonorum*. In preferred aspects, the fungus comprises a species being the same as NRRL deposit Accession No: 50410. In some aspects, the conditioned liquid medium comprises a nutrient mixture comprising increased iron (Fe) content. In certain preferred embodiments, the nutrient mixture comprises a concentration of between 0.1 mM and 10 mM of iron per every 40 g/L of carbon source. In some aspects, the conditioned liquid medium can comprise a nutrient mixture that comprises Ni. In certain aspects, $NiSO_4$ is added in a concentration ranging from about 1 ppm to about 20 ppm of $NiSO_4$. In some aspects, the conditioned liquid medium can comprise a nutrient mixture that comprises malic acid. In certain aspects, malic acid is at a concentration of about 0.01%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or about 10%. In some aspects, the conditioned liquid medium can comprise a nutrient mixture that comprises one or more amino acids selected from the group consisting of: L-isoleucine, L-tryptophan, and L-serine. In certain aspects, the one or more amino acids is at a concentration of about 1 mg/L, 10 mg/L, 50 mg/L, 100 mg/L, 200 mg/L, 300 mg/L, 400 mg/L, 500 mg/L, 600 mg/L, 700 mg/L, 800 mg/L, 900 mg/L, or about 1000 mg/L. In certain aspects, the one or more amino acids is at a concentration of about 400 mg/L.

The conditioned media described herein can be used to support the growth and/or maintenance of various organisms, including organisms capable of degrading cellulose or partially degraded cellulose.

Also described herein is a facility comprising: a vessel for holding liquid medium conditioned by a cellulose degrading fungus of the genus *Penicillium*; an extraction apparatus comprising an extract of lipids derived from said fungus; and a drying apparatus comprising dried fungus. In some aspects, the extract of lipids comprises TAG. In other aspects, the extract of lipids comprises phospholipids. In other aspects, the phospholipids comprise lecithin. In yet other aspects, the dried fungus is suitable for animal and/or human consumption. In certain preferred aspects, the fungus comprises *Penicillium menonorum*. In preferred aspects, the fungus comprises a species being the same as NRRL deposit Accession No: 50410.

With respect to any of the above-described compositions and/or processes, the cellulose degrading fungus of the genus *Penicillium* can be selected from the group consisting of a fungus of the genus *Penicillium* that is the same species as the fungus having NRRL deposit Accession No: 50410; a fungus comprising a 5.8S ribosomal RNA gene sequence having at least 98% nucleotide sequencing identity with the nucleic acid of SEQ ID NO: 1; fungus comprising an ITS1 sequence with at least 98% sequence identity to SEQ ID NO: 2; a fungus comprising an ITS2 sequence with at least 98% sequence identity to SEQ ID NO: 3; a fungus comprising a 28S ribosomal RNA gene sequence with at least 98% sequence identity to SEQ ID NO: 4; and *Penicillium menonorum*.

In some aspects of the above-described compositions and/or processes that include a medium, the medium can comprise at least one dissolved nutrient selected from the group consisting of glycerol, yeast extract, corn steep, mycelial cell extract from earlier cultures of the fungus, sulfates, nitrates, calcium salts, ammonium phosphate, magnesium sulfate, calcium chloride, ferric citrate, potassium sulfate, sodium acetate, sodium molybdate, copper sulfate, cobalt nitrate, zinc sulfate, boric acid and manganese chloride. In certain preferred aspects, the medium comprises $MgSO_4$ and/or other salt(s) of Mg at a concentration of at least 0.5 mM. In other aspects, the medium comprises a detergent. In some such aspects, the medium comprises a non-ionic detergent selected from Polysorbate 80 (Tween80), Polysorbate 20 (Tween20), deoxycholate and Brij-35. In certain aspects, the non-ionic detergent comprises Polysorbate 80 (Tween80). In a preferred aspect, the liquid medium comprises Polysorbate 80 (Tween80) at a concentration of at least 0.01%. In some aspects, the medium is at a pH of at least about 3.5.

In some aspects of the above-described compositions and/or processes that include a liquid medium, the liquid medium can comprise dissolved oxygen in a range of about 0.1 mg/L to about 100 mg/L. In other aspects, the dissolved oxygen is in a range of about 0.5 mg/L to about 40 mg/L.

In some aspects of the above-described compositions and/or processes that include a liquid medium, the liquid medium can comprise nutrient mixtures that provide for enhanced TAG accumulation in cultures of fungal microbes. In some aspects, the nutrient mixture comprises increased iron (Fe) content. In certain aspects, the nutrient mixture comprises increased iron content wherein the iron content in the nutrient mixture is increased by a factor of about two to a factor of about thirty. In certain embodiments, the nutrient mixture comprises a concentration of about 0.1 mM, 0.2 mM, 0.3 mM, 0.4 mM, 0.5 mM, 0.6 mM, 0.7 mM, 0.8 mM, 0.9 mM to about 1 mM of iron per every 40 g/L of carbon source. In certain preferred embodiments, the nutrient mixture comprises a concentration of about 0.5 mM of iron per every 40 g/L of carbon source.

In some aspects of the above-described compositions and/or processes that include a liquid medium, the liquid medium can comprise a nutrient mixture that comprises Ni. In certain aspects, $NiSO_4$ is added in a concentration ranging from about 0.1 ppm, 1 ppm, 10 ppm, 100 ppm to about 1000 ppm. In certain aspects, $NiSO_4$ is added in a concentration ranging from about 1 ppm to about 100 ppm of $NiSO_4$. In certain aspects, $NiSO_4$ is added in a concentration ranging from about 1.1 ppm to about 11.1 ppm of $NiSO_4$.

In some aspects of the above-described compositions and/or processes that include a liquid medium, the liquid medium can comprise a nutrient mixture that comprises malic acid. In certain aspects, malic acid is added to the nutrient mixture before the culture is inoculated. In certain aspects, the malic acid concentration in the nutrient mix prior to inoculation is about 0.01%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or about 10%.

In some aspects of the above-described compositions and/or processes that include a liquid medium, the liquid medium can comprise a nutrient mixture that comprises one or more amino acids selected from the group consisting of: L-isoleucine, L-tryptophan, and L-serine. In certain aspects, the one or more amino acids is added to the nutrient mixture at a concentration of about 1 mg/L, 10 mg/L, 50 mg/L, 100 mg/L, 200 mg/L, 300 mg/L, 400 mg/L, 500 mg/L, 600 mg/L, 700 mg/L, 800 mg/L, 900 mg/L, or about 1000 mg/L. In certain aspects, the one or more amino acids is added to the nutrient mixture at a concentration of about 400 mg/L.

Also presented herein are methods of enhancing TAG accumulation in cultures of fungal microbes. In some aspects, the method can comprise adjusting the iron (Fe) content of a culture medium. In certain aspects, the method comprises increasing the iron concentration in the nutrient mixture by a factor of from two to as high as thirty, with a preferred concentration of about 0.5 mM of iron per every 40 g/L of carbon source.

In some aspects, the method can comprise adding nickel to the nutrient mixture. In certain aspects, $NiSO_4$ is added in a concentration ranging from about 0.1 ppm, 1 ppm, 10 ppm, 100 ppm to about 1000 ppm. In certain aspects, $NiSO_4$ is added in a concentration ranging from about 1 ppm to about 100 ppm of $NiSO_4$. In certain aspects, $NiSO_4$ is added in a concentration ranging from about 1.1 ppm to about 11.1 ppm of $NiSO_4$.

In some aspects, the method can comprise adding malic acid to the nutrient mixture. In certain aspects, malic acid is added to the nutrient mixture before the culture is inoculated. In certain aspects, the malic acid concentration in the nutrient mix prior to inoculation is about 0.01%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or about 10%.

In some aspects, the method can comprise adding to the nutrient mixture one or more amino acids selected from the group consisting of: L-isoleucine, L-tryptophan, and L-serine. In certain aspects, the one or more amino acids is added to the nutrient mixture at a concentration of about 1 mg/L, 10 mg/L, 50 mg/L, 100 mg/L, 200 mg/L, 300 mg/L, 400 mg/L, 500 mg/L, 600 mg/L, 700 mg/L, 800 mg/L, 900 mg/L, or about 1000 mg/L. In certain aspects, the one or more amino acids is added to the nutrient mixture at a concentration of about 400 mg/L.

Also described herein is a biomass of a cellulose degrading fungus of the genus *Penicillium*, wherein the fungus comprises at least 5% triacylglyceride by weight. In certain aspects, the cellulose degrading fungus of the genus *Penicillium* comprises at least about 10% to about 50% triacylglyceride by dry weight. In a preferred aspect, the cellulose degrading fungus of the genus *Penicillium* comprises at least about 25% to about 50% triacylglyceride by dry weight.

In some aspects, the biomass has an enriched iron content. In some aspects, the biomass has an enriched malic acid content. In some aspects, the biomass has an enriched content of one or more amino acids selected from the group consisting of: L-isoleucine, L-tryptophan, and L-serine.

Animal Feed

In some embodiments described herein, compositions and methods are provided which utilize fungal biomass for animal meal. In one aspect of the invention, an admixture is provided comprising fungal biomass and whey. In some aspects, the fungal biomass comprises biomass derived from a cellulose degrading fungus of the genus *Penicillium*. In certain aspects, the admixture is suitable for animal and/or human consumption.

In some aspects, the biomass has been substantially depleted of a lipid product. In certain aspects, the lipid product comprises triacylglycerides (TAG). In other aspects, the lipid product comprises TAG and a phospholipid co-product. In certain aspects, the phospholipid co-product comprises lecithin.

In certain aspects, the biomass and the whey form a slurry. In certain aspects, the biomass and whey can be in a dry biomass/whey ratio ranging from about 1:100 to about 100:1 (vol/vol). In other aspects, the biomass and whey are in a dry biomass/whey ratio ranging from about 1:10 to about 10:1 (vol/vol).

Also provided is a method of manufacture of an animal feed comprising combining dried fungal biomass with whey, thereby forming an admixture. In certain aspects, the method comprises, prior to combining: extracting a lipid product from fungal biomass; and, optionally, drying the fungal biomass, thereby producing dried fungal biomass. In some aspects, the fungal biomass comprises biomass derived from a cellulose degrading fungus of the genus *Penicillium*. In certain aspects, the admixture is suitable for animal and/or human consumption.

In certain aspects, the lipid product extracted from the fungal biomass comprises TAG. In other aspects, the lipid product comprises TAG and a phospholipid co-product. In certain aspects, the phospholipid co-product comprises lecithin.

In certain aspects, the biomass and the whey form a slurry. In certain aspects, the biomass and whey can be in a dry biomass/whey ratio ranging from about 1:100 to about 100:1 (vol/vol). In other aspects, the biomass and whey are in a dry biomass/whey ratio ranging from about 1:10 to about 10:1 (vol/vol).

Also presented herein is a method of shipping a fungal biomass-whey slurry to a farm. In certain aspects the method comprises pumping whey out of a truck. In certain aspects, the method additionally comprises pumping a fungal biomass-whey slurry into a tanker truck. In other aspects, the slurry is pumped to a storage tank for animal feeding.

Also provided is a method of feeding an animal comprising providing to the animal an admixture comprising fungal biomass and whey. In some aspects, the method further comprises identifying an animal that would likely benefit from consuming the admixture. For example, identifying an animal that would likely have a superior rate of growth or enhanced immune system function if fed the fungal biomass or admixture described herein as compared to if fed another feed. In some aspects, the fungal biomass comprises biomass derived from a cellulose degrading fungus of the genus *Penicillium*. In certain aspects, the admixture is suitable for animal and/or human consumption.

In some aspects, the biomass has been substantially depleted of a lipid product. In certain aspects, the lipid product comprises TAG. In other aspects, the lipid product comprises TAG and a phospholipid co-product. In certain aspects, the phospholipid co-product comprises lecithin.

In certain aspects, the biomass and the whey form a slurry. In certain aspects, the biomass and whey can be in a dry biomass/whey ratio ranging from about 1:100 to about 100:1 (vol/vol). In other aspects, the biomass and whey are in a dry biomass/whey ratio ranging from about 1:10 to about 10:1 (vol/vol).

Also presented is a method of feeding an animal comprising providing to the animal a fungal biomass derived from a cellulose degrading fungus of the genus *Penicillium*.

Also presented herein is a method of improving the longevity of an animal, comprising: identifying an animal in need of having improved longevity; and providing to the animal an animal feed comprising fungal biomass derived from a cellulose degrading fungus of the genus *Penicillium*.

Also presented herein is a method of increasing the resistance of an animal to an infection, comprising: identifying an animal in need of increased resistance to an infection; and proving to said animal an animal feed comprising a fungal biomass derived from a cellulose degrading fungus of the genus *Penicillium*.

With respect to any of the above-described methods, in certain aspects, the animal can be an aquatic animal. In certain other aspects, the animal can be a terrestrial animal or avian. In certain aspects, the biomass has been substantially depleted of a lipid product. In certain aspects, the lipid product comprises TAG. In other aspects, the lipid product comprises TAG and a phospholipid co-product. In certain aspects, the phospholipid co-product comprises lecithin.

In some aspects of the above above-described methods, the animal feed can comprise the biomass in an amount ranging from 1% to 100% by weight. Accordingly, in some embodiments, the animal feed comprises fungal biomass without whey. In some aspects, the animal feed can comprise the biomass in an amount ranging from 5% to 10% by weight.

Also presented herein is an oxygenated mycelial mat comprising a cellulose degrading fungus of the genus *Penicillium*. In certain aspects, the mycelial mat comprises dissolved oxygen in an amount greater than at least 0.1 milligrams per liter.

Also presented herein is a mycelial mat comprising a cellulose degrading fungus of the genus *Penicillium*, the fungus comprising greater than about 25% (cdw) crude protein. In certain aspects, the fungus comprises greater than about 30% (cdw) crude protein.

Also presented herein is a mycelial mat comprising a cellulose degrading fungus of the genus *Penicillium*, said fungus comprising greater than about 10%, 15%, 20%, 25%, 30%, 35%, 40%, 45%, 50%, 55% or greater than 60% (cdw) TAG content.

With respect to any of the above-described compositions and/or methods, the cellulose degrading fungus of the genus *Penicillium* can be selected from the group consisting of a fungus of the genus *Penicillium* that is the same species as the fungus having NRRL deposit Accession No: 50410; a fungus comprising a 5.8S ribosomal RNA gene sequence having at least 98% nucleotide sequencing identity with the nucleic acid of SEQ ID NO: 1; fungus comprising an ITS1 sequence with at least 98% sequence identity to SEQ ID NO: 2; a fungus comprising an ITS2 sequence with at least 98% sequence identity to SEQ ID NO: 3; a fungus comprising a 28S ribosomal RNA gene sequence with at least 98% sequence identity to SEQ ID NO: 4; and *Penicillium menonorum*.

Other features and advantages of the invention will be apparent from the following detailed description, the claims and the appended drawings.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 14 depicts the sequence of the internal transcribed spacer (ITS) 1 (SEQ ID NO: 2), 5.8S rRNA gene (SEQ ID NO: 1), and ITS 2 (SEQ ID NO:3) and partial 28S rRNA gene (SEQ ID NO: 4) nucleotide sequences. The entire sequence shown in the figure is set forth as SEQ ID NO. 5, which also depicts the 225 nucleotides that are 5' of ITS1.

DETAILED DESCRIPTION OF THE INVENTION

Figure 1:
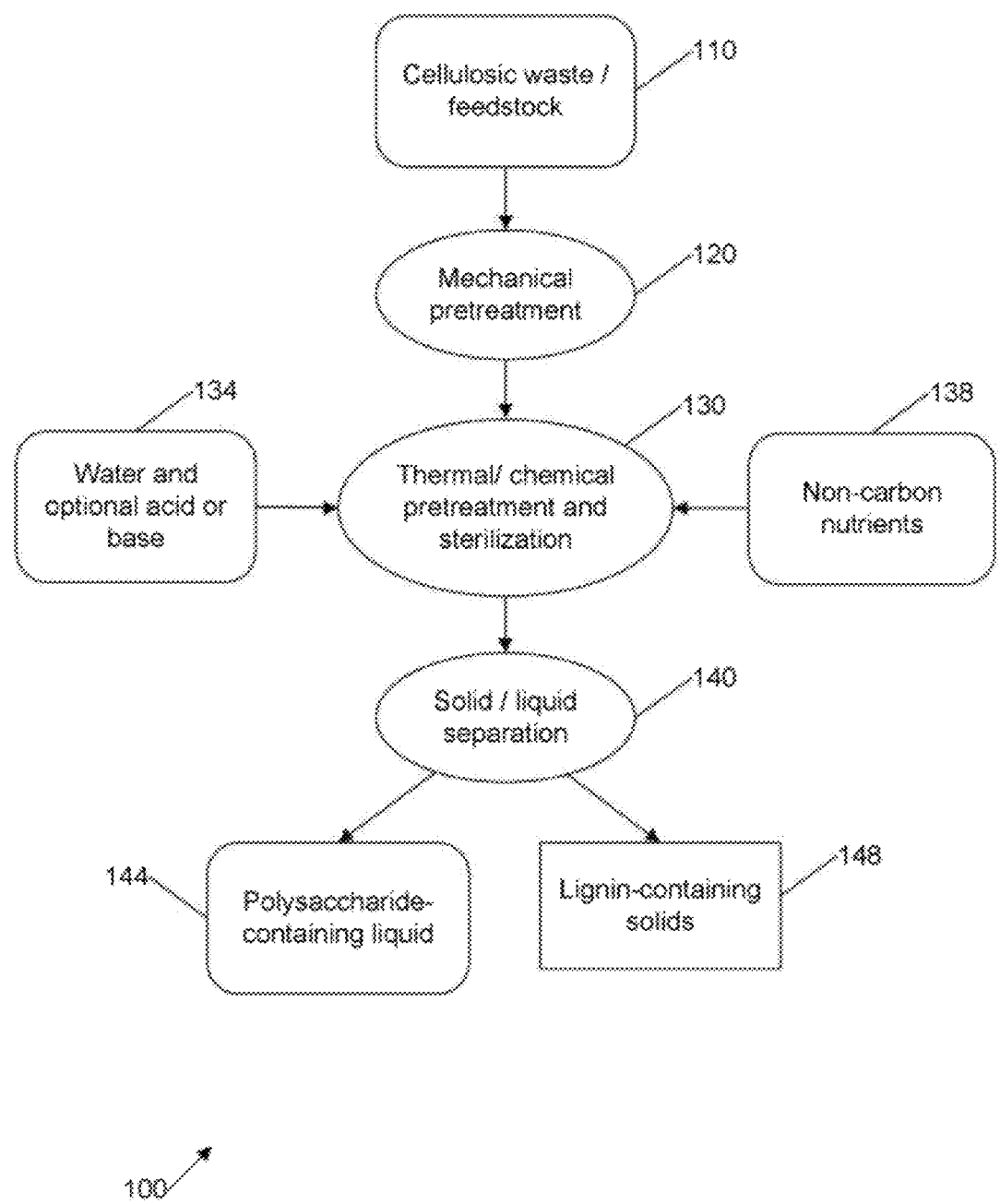
FIG. 1 is a flow chart of a cellulosic feedstock pretreatment process according to an embodiment of the invention.

After reading this description it will become apparent to one skilled in the art how to implement the invention in various alternative embodiments and alternative applications.

However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

The described embodiments relate to systems and methods for production of liquid biofuel from low-value starting materials. In some embodiments, the systems and methods relate specifically to the production of diesel, gasoline and/or aviation fuel from cellulosic feedstocks. In some embodiments, the method includes a multi-step process that inputs raw feedstock and outputs triacylglyceride ("TAG") and aromatic compounds. In some embodiments, the systems and methods relate specifically to the production of biodiesel fuel. The production of biodiesel fuel is further described in co-pending application Ser. No. 12/573,732, filed Oct. 5, 2009, entitled "Microbial Processing of Cellulosic Feedstocks for Fuel," which is incorporated herein by reference.

Present methods of converting cellulosic biomass utilize biomasses specifically cultivated for producing biofuels. In addition to these "cultivated cellulosic biomasses", cellulosic biomass may be obtained from cellulosic waste materials such as sawdust, wood chips, cellulose, algae, other biological materials, municipal solid waste (e.g., paper, cardboard, food waste, garden waste, etc.), and the like.

A process in accordance with an embodiment of the present invention includes converting cellulosic waste materials into liquid fuel. In one aspect, cellulosic material such as agricultural waste is converted into lipids such as TAG, using specially selected or developed microbes (e.g., including genetically engineered microbes, competitively bred microbes, etc.). These microbes convert free sugars, cellulose and hemicellulose, major components of plant matter, into TAG.

TAG includes three fatty acids linked to a glycerol backbone. When dissociated from the glycerol and hydrotreated, the fatty acids are converted to hydrocarbons, which form the major components of diesel, gasoline and jet fuel. In some embodiments, TAG itself may serve as a component of fuel. A benefit associated with the present process is that no net carbon is added to the atmosphere when the fuel is burned because the feedstock was originally produced by photosynthesis, sequestering carbon dioxide from the atmosphere.

Gasoline and jet fuel specifications require, in addition to alkanes, a certain proportion of aromatic compounds. TAG cannot be readily converted to aromatic compounds. However, plant matter also contains lignin, a polymeric agglomeration of aromatic compounds that can be broken down into the aromatics required for fuel. Specialized microbes attack lignin and convert it into smaller, individual aromatic compounds. Thus, microbial conversion processes can suffice to convert agricultural and municipal waste originating from plant matter into all the components of fuel.

Additionally, contemplated herein are compositions that include one or more specific genera and species of microbes that not only convert a wide range of cellulosic feedstocks into lipids effectively, but also yield desirable co-products. An example of the latter includes the spent microbial biomass after the lipids have been extracted, which can be sold as protein meal to feed livestock in agriculture and aquaculture. The protein meal may also find use as a source of human nutrition. Metabolites produced and/or secreted by the one or more microbes provide another class of co-products. In some embodiments, the metabolites may be primary metabolites.

It will be appreciated that not every microbe is suitable for the conversion of cellulosic matter to lipids for fuel. For example, many microbes convert excess energy inputs into wax esters or polyhydroxyalkanoates, which are less desirable than triaclyglycerides (TAG). Many microbes are pathogenic or otherwise unsuitable for animal or human consumption, or they provide insufficient nutritional value to make a valuable nutritional co-product. Many microbes also do not produce useful or economically valuable metabolite co-products.

In addition to the foregoing, the use of genetically modified organisms is discouraged because of concerns about environmental release. As such, specific genera and species of microbes that are suitable for efficient production of biofuels from cellulosic materials would be beneficial. Furthermore, specific genera and species of microbes that are capable of and/or useful for both the production of biofuel and one or more economically valuable co-products would be even more beneficial.

Described herein is a novel cellulose degrading fungus of the species *Penicillium*. It has been surprisingly found that this fungus can be grown in culture in vitro. It has also been surprisingly found that this fungus can be grown in a bioprocess reactor under conditions that permit the fungus to produce biofuel using a cellulosic carbon source. Furthermore, it has been surprisingly found that this fungus can be grown in a bioprocess reactor under conditions that permit the fungus to produce biofuel and one or more economically valuable co-products.

The novel cellulose degrading fungus is designated herein as *Penicillium menonorum*. In a preferred embodiment, the fungus comprises the strain designated "MM-P1," which is a wild-type strain of *Penicillium menonorum* that was isolated from an environmental sample and surprisingly shown to have the following desirable properties. First, *Penicillium menonorum* efficiently converts cellulosic sugars to lipids effectively. Second, *Penicillium menonorum* is able to store excess energy primarily in the form of TAG rather than or in addition to wax esters, polyhydroxyalkanoates or other substances. Third, Penicillium menonorum is non-pathogenic to animals and humans. Additionally, *Penicillium menonorum* is a wild-strain microbe and has not been genetically engineered, thus alleviating concern over its release into the environment. In a preferred embodiment, the cellulose degrading fungus comprises a *Penicillium* species that is the same as the deposited strain having NRRL Accession No. 50410.

As used herein, the term "cellulose degrading" refers to the ability of an organism to consume cellulose, hemicellulose, and/or other saccharides derived from lignocellulosic materials. In some embodiments, cellulose degrading refers to an organism that produces enzymes that degrade cellulose and/or hemicellulose. In other embodiments, cellulose degrading refers to an organism can break down cellulose and use portions of polymeric cellulose as an energy source.

In accordance with an embodiment of the present invention, a biomass feedstock (e.g., sawdust, wood chips, cellulose, algae, other biological materials, or other solid materials) includes high-molecular-weight, high-energy-content molecules including cellulose, hemicellulose and lignin to be converted into fuel. The feedstock can generally be biological matter, which generally includes organic compounds from plant or other lignocellulosic sources. The resulting fuel may be in fluid form, meaning that gaseous and liquid components may contribute to the make up of the fuel. For example, in one embodiment, the resulting fuel may include methane (gas) and octane (liquid), as well as a variety of other components. The feedstock material may be a low-value or waste material.

In certain embodiments of the present invention, a cellulosic biomass feedstock includes at least 10% cellulosic waste materials. In some embodiments, the cellulosic biomass feedstock includes greater than 50% cellulosic waste materials. In still other embodiments, the cellulosic biomass feedstock includes up to 100% cellulosic waste materials.

In one aspect, the feedstock may be a biological product of plant origin, thus resulting in no net increase in atmospheric carbon dioxide when the resultant fuel product is combusted.

In some embodiments, two or more feedstocks may be used. For example, a secondary feedstock may include any material by-product of a cellulose conversion process, which material is capable of being converted into fuel by microbial action. The secondary feedstock may include glycerol molecules or fragments thereof, or glycerol with additional carbon atoms or short paraffinic chains attached. Such compounds can be produced, for example, when alkanes are cleaved from TAG or when TAG is transesterified to produce biodiesel.

For simplicity of explanation, a process in accordance with the present invention may be divided into three main steps: (1) feedstock pretreatment, (2) inoculation and fermentation/digestion, and (3) harvesting and extraction of the TAG and/or aromatic products.

(1) Feedstock Pretreatment

In an embodiment, raw feedstock is pretreated to make its carbon content accessible to microbial digestion and to kill any naturally present microbes that might compete with the preferred species introduced for the purpose of TAG and/or aromatic compound production. Pretreatment can include three steps: (1) mechanical pretreatment, (2) thermal-chemical pretreatment and heat sterilization and/or ultraviolet ("UV") irradiation and/or pasteurization, and (3) filtration/separation. In the mechanical pretreatment step, raw feedstock may be conveyed to a chopper, shredder, grinder or other mechanical processor to increase the ratio of surface area to volume.

The thermal-chemical pretreatment step can treat the mechanically processed material with a combination of water, heat and pressure. Optionally, acidic or basic additives or enzymes may also be added prior to heat-pressure treatment. This treatment further opens up the solid component (e.g., increases the ratio of surface area to volume) for microbial access and releases sugars and other compounds (e.g., dissociates cellulose and hemicellulose into component sugars, dimers and/or oligomers) into a liquid phase to make it more amenable to microbial digestion. Examples of such treatment include the class of processes known variously as hydrolysis or saccharification, but lower-energy processing, such as simple soaking, boiling, or cooking in water, may also be utilized.

In one embodiment, non-carbon microbial nutrients are added prior to the thermal-chemical pretreatment step. Non-carbon microbial nutrients include, for example, sources of nitrogen, phosphorus, sulfur, metals, etc. After adding the non-carbon microbial nutrients, the entirety may then be sterilized, such as via autoclaving. In some embodiments, the non-carbon microbial nutrients are sterilized separately from the sugar components. In some embodiments, the sugar components are not sterilized.

The filtration/separation step 140 preferably separates the solid matter (e.g., where the lignin is concentrated) from the liquid (e.g., which contains most of the sugars and polysaccharides from the cellulose and hemicellulose in the feedstock). In some embodiments, the filtration/separation step 140 is optional. Consequently, in these embodiments, the solid matter and liquid remain together throughout processing.

In some embodiments, the feedstock is fortified (e.g., via the addition of glycerol.) For example, glycerol used in the feedstock fortification may be obtained as a byproduct of some TAG-to-alkanes conversion processes. Generally, glycerol is released by the conversion of TAG to produce biodiesel fuel (e.g. via transesterification). The released glycerol may then be metabolized to contribute to TAG formation. A benefit of using the glycerol to form TAG is that it may speed the growth or TAG accumulation of certain microbial species during fermentation, discussed below. It is understood that glycerol obtained from transesterification is not high-purity, but rather includes a variety of constituents.

Referring now to FIG. 1, a flow chart of a cellulosic feedstock pretreatment process 100 in accordance with an embodiment of the invention is shown. The pretreatment process 100 includes a receiving stage 110 for receiving the cellulosic feedstock and a mechanical pretreatment stage 120 for transforming the feedstock into small particles.

The pretreatment process 100 also includes a thermo-chemical pretreatment stage 130 to open up the cellulosic structure, rendering the cellulosic structure more accessible to the microbes and to bring some of the sugars and polysaccharides into solution. In some embodiments, water and, optionally, acidic or basic additives 134 are added to the feedstock during this thermo-chemical pretreatment stage 130. In some embodiments, non-carbon nutrients 138 used for the microbial metabolization are also added during this thermo-chemical pretreatment stage 130. In some embodiments, the non-carbon nutrients 138 are sterilized separately from the feedstock in the thermal/chemical pretreatment and sterilization step 130. Thereafter, the non-carbon nutrients 138 and the feedstock are combined after the solid/liquid separation step 140. In other embodiments, the non-carbon nutrients and the feedstock are combined prior to the solid/liquid separation step 140. It should be appreciated that the thermo-chemical treatment step 130 also serves to sterilize the cellulosic material and surrounding liquid to inhibit potentially competing microorganisms. In other embodiments the non-carbon nutrients can be added to the liquid medium after the liquid/solid separation step.

The pretreatment process 100 also includes a solid-liquid separation stage 140 which may use mechanical means such as filters and/or centrifuges to separate the bulk of the solid feedstock from the liquid portion. As described above, the liquid portion 144 includes mostly sugars and polysaccharides, while the solid portion 148 includes lignin as well as undissolved cellulose and hemicellulose.

(2) Inoculation and Fermentation

In the inoculation and fermentation stage, the solid and liquid portions of the treated feedstock can be placed in separate digesters. In some embodiments the solid and liquid portions of the treated feedstock are not placed in separate digesters. The digesters are vessels containing the feedstock material and microbes that utilize the feedstock to generate lipids and/or break down the feedstock into aromatic compounds, respectively, a solvent (e.g., water), and non-carbon nutrients (e.g., nitrates, phosphates, trace metals, and the like).

The microbes may be species of any of two classes: one class which converts cellulose, hemicellulose or glycerol into lipids, and a second class which breaks lignin down into aromatic compounds. Microbes including bacterial and/or fungal species which convert cellulose, hemicellulose or glycerol into lipids include, for example, *Trichoderma reesi*,

*Acinetobacter* sp., and members of the *Actinomyces* and *Streptomyces* genera, some of which have been reported to store up to 80% of dry cell mass as lipids. In a preferred embodiment, the microbes comprise a cellulose degrading fungus of the genus *Penicillium* as described in further detail below. Other species of bacteria and fungi break lignin down into aromatics. In some embodiments, the microbes are filamentatious or have a filamentatious morphology or structure. This filamentatious morphology often results in chain growth of the microbes, which allows the microbes to be collected in traditional sieves or separation means.

Isolated Fungus

In accordance with the above, described herein is a cellulose degrading fungus of the genus *Penicillium*. In some embodiments, the fungus comprises a fungus of the same species as the isolated *Penicillium menonorum* strain MM-P1 deposited with the Agricultural Research Service Culture Collection (NRRL) on Aug. 2, 2010, having been assigned deposit Accession No: 50410. The address of the depository, NRRL, is 1815 North University Street, Peoria, Ill. 61604. This deposit has been made in full accordance with the Budapest Treaty on the International Recognition of the Deposit of Microorganisms for the Purposes of Patent Procedure. In a preferred embodiment, the isolated fungus comprises *Penicillium menonorum* and progeny thereof. In another preferred embodiment, the isolated fungus comprises NRRL deposit Accession No: 50410 and progeny thereof.

In one embodiment, the isolated fungus can comprise a 5.8S ribosomal RNA gene sequence as set forth in SEQ ID NO: 1. Accordingly, it will be appreciated that the isolated fungus can have a 5.8S ribosomal RNA gene sequence with at least 10%, 20%, 30%, 40%, 50%, 60%, 70%, 80%, 85%, 86%, 87%, 88%, 89%, 90%, 91%, 92%, 93%, 94%, 95%, 96%, 97%, 98% or at least 99% nucleotide sequence identity with the nucleic acid of SEQ ID NO: 1.

In another embodiment, the isolated fungus can comprise an internal transcribed spacer 1 (ITS1) sequence as set forth in SEQ ID NO: 2. Accordingly, it will be appreciated that the isolated fungus can have an ITS1 sequence with at least 10%, 20%, 30%, 40%, 50%, 60%, 70%, 80%, 85%, 86%, 87%, 88%, 89%, 90%, 91%, 92%, 93%, 94%, 95%, 96%, 97%, 98% or at least 99% nucleotide sequence identity with the nucleic acid of SEQ ID NO: 2.

In still another embodiment, the isolated fungus can comprise an internal transcribed spacer 2 (ITS2) sequence as set forth in SEQ ID NO: 3. Accordingly, it will be appreciated that the isolated fungus can have an ITS2 sequence with at least 10%, 20%, 30%, 40%, 50%, 60%, 70%, 80%, 85%, 86%, 87%, 88%, 89%, 90%, 91%, 92%, 93%, 94%, 95%, 96%, 97%, 98% or at least 99% nucleotide sequence identity with the nucleic acid of SEQ ID NO: 3.

In yet another embodiment, the isolated fungus can comprise a 28S ribosomal RNA gene sequence as set forth in SEQ ID NO: 4. Accordingly, it will be appreciated that the isolated fungus can have a 28S ribosomal RNA gene sequence with at least 10%, 20%, 30%, 40%, 50%, 60%, 70%, 80%, 85%, 86%, 87%, 88%, 89%, 90%, 91%, 92%, 93%, 94%, 95%, 96%, 97%, 98% or at least 99% nucleotide sequence identity with the nucleic acid of SEQ ID NO: 4.

Figure 15:
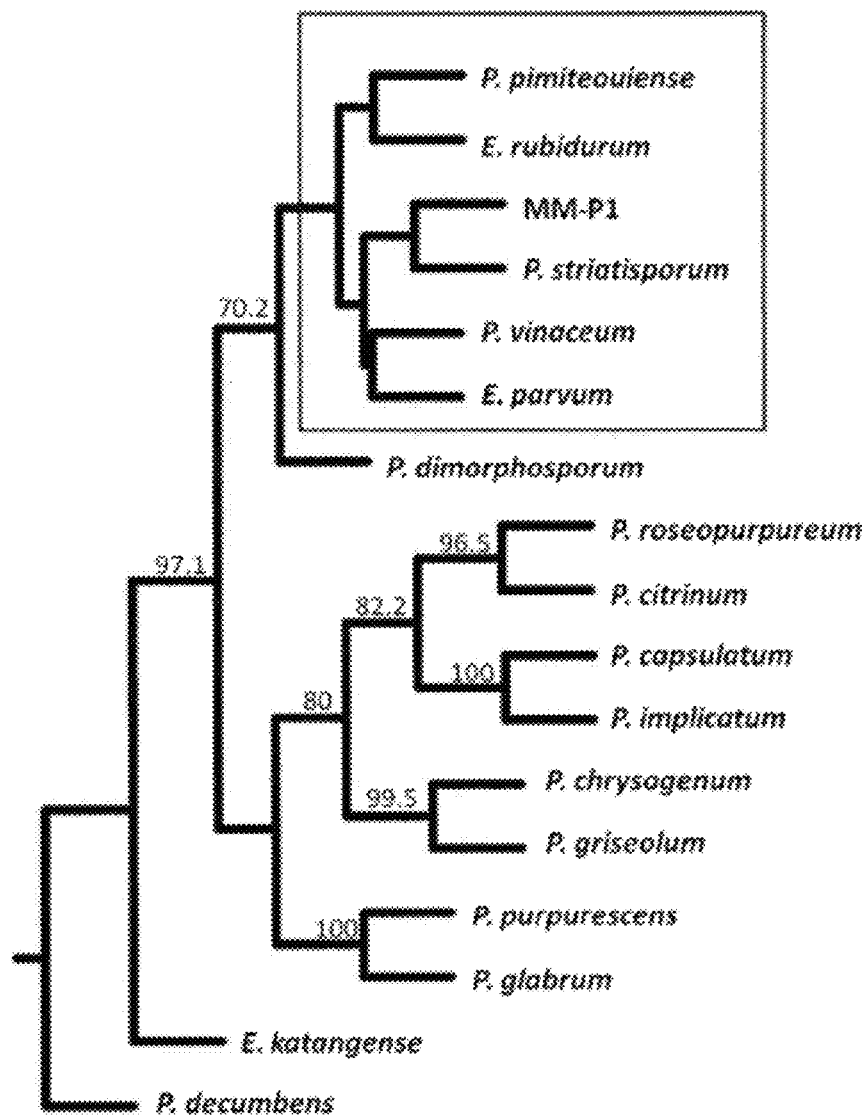
FIG. 15 depicts a dendrogram of MM-P1, its closest known relatives, and other *Penicillium* (P.) and *Eupenicillium* (E.) strains, to show relatedness of the species, as determined by parsimony analysis. Numbers above the lines indicate bootstrap values for those nodes; only bootstrap values over 70% are shown.
Figure 16:
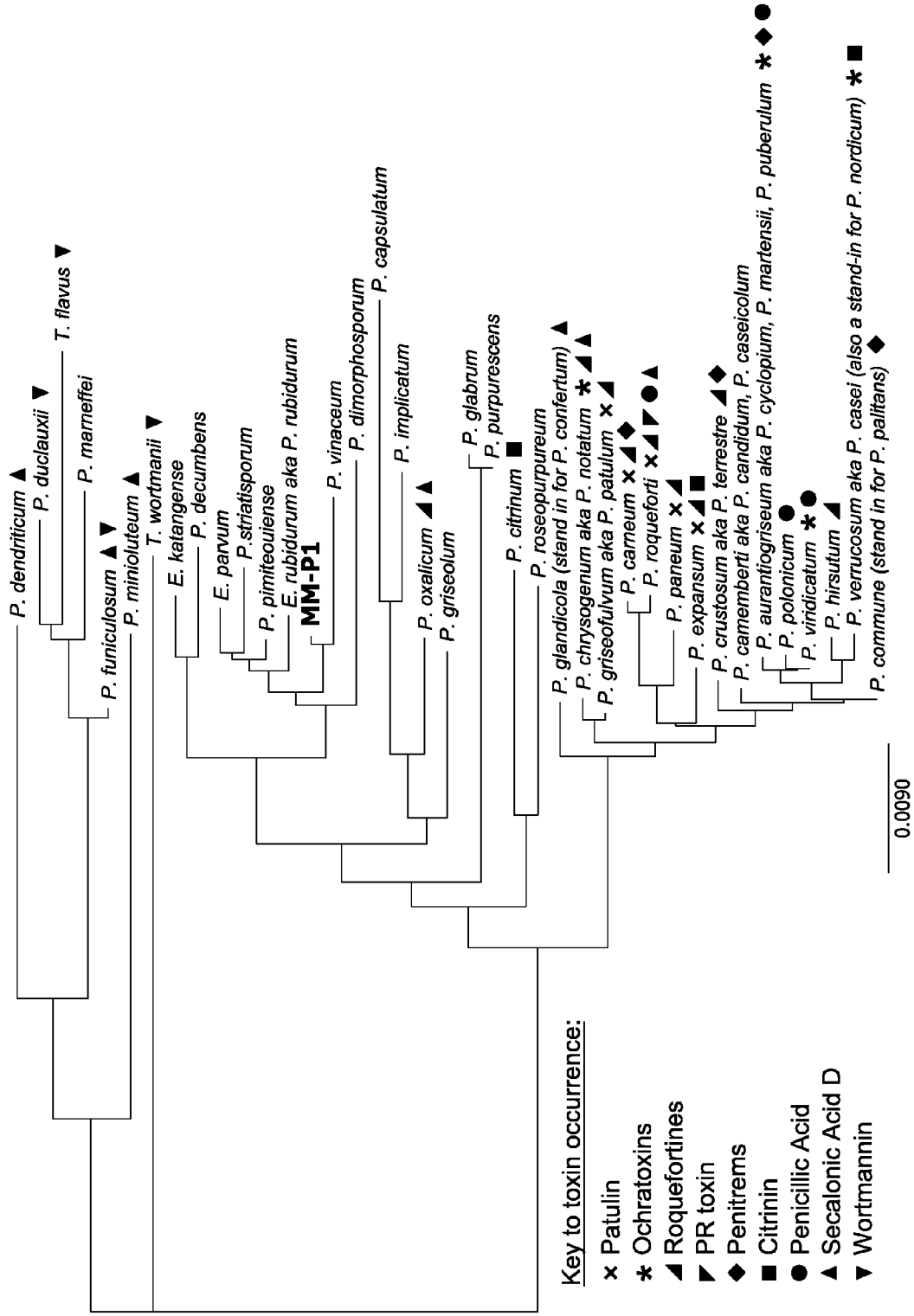
FIG. 16 depicts a Phylogenetic Tree of certain *Penicillium* (P.), *Eupenicillium* (E.), and *Talaromyces* (T.) species with occurrences of some important toxins noted.

In some embodiments, the isolated fungus having the above-described sequence identity with SEQ ID NOs: 1, 2, 3 or 4 is of the genus *Penicillium*. As shown in FIGS. 15 and 16, the isolated fungus may have *Penicillium striatisporum* as its closest identified relative. In some embodiments, the isolated fungus is the teleomorph of *Penicillium menonorum*. In some embodiments, the isolated fungus is the anamorph of *Penicillium menonorum*.

A Nutrient Medium Comprising the Fungus (Fungal Cultures)

It will be appreciated the when an environmental sample of microorganisms is obtained it cannot be predicted whether any of the microorganisms can be extracted from the sample and cultivated in an isolated form. In fact, with many microorganisms, it cannot be predicted whether the microbe can even be successfully cultured in vitro.

The microbes described herein can be grown and cultivated for storage or for scale-up for use in the fermentation processes described elsewhere herein. Accordingly, presented herein is a living, in vitro culture of a cellulose degrading fungus of the genus *Penicillium* growing on a nutrient medium. In preferred embodiments, the fungus growing on the nutrient medium comprises *Penicillium menonorum*. Accordingly, in one embodiment, the cellulose degrading fungus is of the genus *Penicillium*, the species being the same as NRRL deposit Accession No: 50410.

In certain embodiments, the medium is a solid medium. Techniques for preparing solid nutrient growth media are well-known. For example, a gelified nutrient medium such as an agar plate or dish may be used. A preferred medium for growth of *Penicillium menonorum* is potato dextrose agar (PDA). Another preferred medium for growth of *Penicillium menonorum* is cornmeal agar. Another preferred medium for growth of *Penicillium menonorum* is carboxymethylcellulose (CMC). It will be appreciated that any other suitable solid medium, such as a grain, may be utilized. The fungus may be transferred from the solid medium to other media and/or vessels by removing from a dish culture an agar plug having mycelium growing thereon and transferring the plug to the other media and/or vessels. In other embodiments, spores, such as conidiospores (conidia) can be transferred.

In some preferred embodiments, the nutrient medium can be a liquid medium. Techniques for preparing solid nutrient liquid media are well-known. Examples of nutrient-rich liquid culture media, such as malt extract broth and Sabouraud dextrose broth. Typically, liquid cultures are started by inoculating with isolated conidia or conidia obtained from a plate culture.

Here, it has been surprisingly found that the novel *Penicillium* species *Penicillium menonorum* has enhanced growth and enhanced capacity to produce molecules used in biofuel production and/or other co-products in both liquid and solid medium when certain nutrients are present in specified amounts and/or ratios. In some preferred embodiments, the growth and/or capacity to produce molecules used in biofuel production and/or other co-products is optimized. Compositions comprising such media provide conditions where the fungus can produce metabolic products that can be used in biofuel production and/or the production of other valuable co-products. In a preferred embodiment, the media provide conditions where the fungus can produce such metabolic products in an economically feasible and/or economically efficient manner.

In a preferred embodiment, the fungal culture comprises a medium comprising a carbon source and a nitrogen source, wherein the ratio of carbon to nitrogen in the medium ranges from about 1:1 to about 1000:1. In a more preferred embodiment, the ratio of carbon to nitrogen in the medium ranges from about 20:1 to about 30:1, about 40:1, about 50:1, about 60:1, about 70:1, about 80:1, about 90:1 or about 100:1. In a more preferred embodiment, the ratio of carbon to nitrogen is 35:1 to about 55:1 for a balance of biomass yield and TAG yield. Where biomass yield is optimized, a ratio of about 20:1 to about 50:1, and preferably about 23:1 is typical. In other preferred embodiments where TAG yield is optimized, a larger ratio is typical, such as greater than about 100:1 and preferably greater than 200:1.

The carbon source in the liquid or solid medium can be any suitable carbon source for growth of *Penicillium* species in a liquid medium. In certain embodiments, the carbon source can be one or more sugars of non-cellulosic origin. For example, the carbon source can comprise a mixture of sugars such as fructose, glucose and sucrose. In another exemplary embodiment, the carbon source can be a juice material such as cane juice and/or its condensates, up to and including dry solid obtained by complete evaporation. Furthermore, the carbon source can be free sugars transported in a plant material, such as free-running sap of plants. In another such aspect, the carbon source can comprise sugars derived from corn starch.

In other preferred embodiments, the carbon source comprises a cellulosic carbon source or a lysate thereof. For example, the cellulosic carbon source can be derived from a biomass cultivated specifically for biofuels production. Such cultivated cellulosic biomasses can include crops such as algae, grasses, agricultural crops such as corn, soy, sorghum and the like. In addition to these "cultivated cellulosic biomasses", the cellulosic carbon source may be obtained from cellulosic waste materials such as sawdust, wood chips, cellulose, algae, other biological materials, municipal solid waste (e.g., paper, cardboard, food waste, garden waste, etc.), and the like. In some preferred embodiments, the cellulosic carbon source is, or is a hydrolysate of, for example, an origin selected from the group consisting of sorghum grain, other grains, stover of different grains; forage and other grasses; oilseed crops and their stover; nut shells and hulls, including almond hulls; grape and other fruit pomace; yard and agricultural waste of plant origin; algae; wood and wood byproducts including wood chips, bark and sawdust; paper products; animal manure especially including the manure of herbivorous animals; and food waste, especially food waste of plant origin. However, it will be readily appreciated that any suitable cellulosic carbon source can be utilized with the cellulose degrading fungus described herein. In some embodiments the cellulosic carbon source comprises other materials including, but not limited to, lignocelluloses and lysates thereof as well as hemicelluloses and lysates thereof.

As used herein with reference to cellulosic carbon sources, the term "lysate" and other like terms refer to a solubilized or partially solubilized cellulose structure. The term "hydrolysate" refers to a solubilized or partially solubilized cellulose structure produced by a hydrolysis process. Neither lysis nor hydrolysis should be understood to require complete lysis of a cellulosic source material. Generation of a lysate can involve loosening the cellulose structure and/or breaking down or "clipping off" of cellulose chains to produce oligosaccharides that have a one or more beta 1,4 cellulosic linkage.

In some embodiments, the terms "cellulose" and "cellulosic" refer to material comprising cellulose, and include for example, cellulose, hemicellulose, and lignocelluose.

Similarly, as used herein with reference to hemicellulose, hemicellulosic carbon sources, lignocellulose and lignocellulosic carbon sources, the term lysate and like terms refer to a solubilized or partially solubilized cellulose structure derived from hemicellulose, a hemicellulosic material, lignocellulose or a lignocellulosic material. The term "hydrolysate" refers to a solubilized or partially solubilized hemicellulosic or lignocellulose structure produced by a hydrolysis process. Neither lysis nor a hydrolysis should be understood to require complete lysis of a hemicellulosic or lignocellulosic source material. For example, a lysate of lignocellulosic carbon source can contain cellulose and hemicellulose chains that have been loosened from tightly-bound lignin polymers. Generation of a lignocellulosic lysate can involve loosening the cellulose structure and/or breaking down or "clipping off" of cellulose chains to produce oligosaccharides that have a one or more beta 1,4 cellulosic linkage.

In some embodiments, the medium preferably comprises at least one dissolved nutrient. Dissolved nutrients can be any carbon source, nitrogen source or any other mineral or nutrient source. For example, some complex nitrogen sources can include yeast extract, corn steep, mycelial cell extract from earlier cultures of the fungus, and the like. Other dissolved nutrients can include salts such as mineral salts, sulfates, nitrates, calcium salts. For example, the mineral salts can include ammonium salts including ammonium nitrate, ammonium sulfate, and the like. Accordingly, the dissolved nutrients can include nutrients selected from the group consisting of glycerol, yeast extract, corn steep, mycelial cell extract from earlier cultures of the fungus, ammonium phosphate, magnesium sulfate, calcium chloride, ferric citrate, potassium sulfate, sodium acetate, sodium molybdate, copper sulfate, cobalt nitrate, zinc sulfate, boric acid and manganese chloride. It will be appreciated that other nutrients may be selected and added as needed.

In some embodiments, the media can comprise $MgSO_4$ and/or other salt(s) of Mg at a concentration of at least 0.5 mM. Preferably, the concentration of $MgSO_4$ and/or other salt(s) of Mg is at least about 0.5, 1, 5, 10, 20, 30, 40 or at least 50 mM. Furthermore, it has been surprisingly discovered that in the absence of a surfactant such as Tween80, the addition of $MgSO_4$ and/or other salt(s) of Mg increases the amount of TAG produced by the culture when added at approximately 96 hours after inoculation of a culture and increases resultant biomass yield when added at about time 0.

In certain embodiments, the nutrients and procedures described herein can be modulated to significantly increase the accumulation of TAG by *Penicillium menonorum* and other candidate microbes, thus rendering the process more cost-effective. For example, it has been found that standard mineral nutrient recipes for culture of *Penicillium* do not necessarily provide adequate iron for maximum cell growth and thus maximum TAG accumulation by the population. A key enzyme in the lipid synthesis pathway is Acetyl co-A synthetase. The active center of the enzyme, in some organisms, incorporates a nickel (Ni) ion [see, for example, Ragsdale, S W (2009) Nickel-based Enzyme Systems. J. Biol. Chem. 284:18571-18575, hereby incorporated by reference in its entirety]. The standard *Penicillium* culture nutrient formulation includes no Ni. However, presented herein is the surprising discovery that adding Ni to the culture medium of *Penicillium menonorum* can improve TAG accumulation.

Additionally, provided herein is the surprising discovery that adding malic acid to the culture medium of *Penicillium menonorum* can lead to increased biomass and TAG accumulation.

Furthermore, provided herein is the surprising discovery that the presence of tryptophan, serine and isoleucine can enhance *P. menonorum* growth and thus TAG accumulation by the population. In addition, tryptophan may specifically enhance TAG accumulation in each cell of the population.

Accordingly, embodiments of the present disclosure comprise nutrient mixtures that provide for enhanced TAG accumulation in mixtures of fungal microbes. In some aspects, the nutrient mixture comprises increased iron (Fe) content. In certain aspects, the nutrient mixture comprises increased iron content wherein the iron content in the nutrient mixture is increased by a factor of about two to a factor of about thirty.

In certain embodiments, the nutrient mixture comprises a concentration of about 0.1 mM, 0.2 mM, 0.3 mM, 0.4 mM, 0.5 mM, 0.6 mM, 0.7 mM, 0.8 mM, 0.9 mM to about 1 mM of iron per every 40 g/L of carbon source. In certain preferred embodiments, the nutrient mixture comprises a concentration of about 0.5 mM of iron per every 40 g/L of carbon source.

In some aspects, the nutrient mixture comprises Ni. In certain aspects, $NiSO_4$ is added in a concentration ranging from about 0.1 ppm, 1 ppm, 10 ppm, 100 ppm to about 1000 ppm. In certain aspects, $NiSO_4$ is added in a concentration ranging from about 1 ppm to about 100 ppm of $NiSO_4$. In certain aspects, $NiSO_4$ is added in a concentration ranging from about 1.1 ppm to about 11.1 ppm of $NiSO_4$.

In some aspects, the nutrient mixture comprises malic acid. In certain aspects, malic acid is added to the nutrient mixture before the culture is inoculated. In certain aspects, the malic acid concentration in the nutrient mix prior to inoculation is about 0.01%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or about 10%.

In some aspects, the nutrient mixture comprises one or more amino acids selected from the group consisting of: L-isoleucine, L-tryptophan, and L-serine. In certain aspects, the one or more amino acids is added to the nutrient mixture at a concentration of about 1 mg/L, 10 mg/L, 50 mg/L, 100 mg/L, 200 mg/L, 300 mg/L, 400 mg/L, 500 mg/L, 600 mg/L, 700 mg/L, 800 mg/L, 900 mg/L, or about 1000 mg/L. In certain aspects, the one or more amino acids is added to the nutrient mixture at a concentration of about 400 mg/L.

Also presented herein are methods of enhancing TAG accumulation in cultures of fungal microbes. In some aspects, the method can comprise adjusting the iron (Fe) content of a culture medium. In certain aspects, the method comprises increasing the iron concentration in the nutrient mixture by a factor of from two to as high as thirty, with a preferred concentration of about 0.5 mM of iron per every 40 g/L of carbon source.

In some aspects, the method can comprise adding nickel to the nutrient mixture. In certain aspects, $NiSO_4$ is added in a concentration ranging from about 0.1 ppm, 1 ppm, 10 ppm, 100 ppm to about 1000 ppm. In certain aspects, $NiSO_4$ is added in a concentration ranging from about 1 ppm to about 100 ppm of $NiSO_4$. In certain aspects, $NiSO_4$ is added in a concentration ranging from about 1.1 ppm to about 11.1 ppm of $NiSO_4$.

In some aspects, the method can comprise adding malic acid to the nutrient mixture. In certain aspects, malic acid is added to the nutrient mixture before the culture is inoculated. In certain aspects, the malic acid concentration in the nutrient mix prior to inoculation is about 0.01%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or about 10%.

In some aspects, the method can comprise adding to the nutrient mixture one or more amino acids selected from the group consisting of: L-isoleucine, L-tryptophan, and L-serine. In certain aspects, the one or more amino acids is added to the nutrient mixture at a concentration of about 1 mg/L, 10 mg/L, 50 mg/L, 100 mg/L, 200 mg/L, 300 mg/L, 400 mg/L, 500 mg/L, 600 mg/L, 700 mg/L, 800 mg/L, 900 mg/L, or about 1000 mg/L. In certain aspects, the one or more amino acids is added to the nutrient mixture at a concentration of about 400 mg/L.

In some embodiments, the medium comprises a non-ionic detergent such as Polysorbate 80 (Tween80), Polysorbate 20 (Tween20), deoxycholate, Brij-35 and the like. Preferably, the non-ionic detergent is Polysorbate 80 (Tween80). More preferably, the liquid medium comprises Polysorbate 80 (Tween80) at a concentration of at least 0.001%, 0.01% or at least 0.1%. It has been surprisingly found that when $MgSO_4$ and/or other salt(s) of Mg is added at about 96 hours in conjunction with Tween80 added at time 0, both biomass and TAG yields are enhanced.

In preferred embodiments, the medium is at a pH of at about 2.5 to about 10. More preferably, the pH is about 3.0 to about 7.0. More preferably, the pH is about 4.5 to about 6.5. More preferably, the pH is about 5.5. Maintaining a pH that is lower than neutral can help prevent contaminating growth of other organisms such as bacteria. In preferred embodiments, the temperature of the nutrient medium can range from about 20° C. to about 50° C. More preferably, the temperature can range from about 28° C. to about 43° C. Where biomass and/or TAG yield is to be optimized, the optimal temperature can range from about 36° C. to about 39° C., with a preferred temperature of 37° C. It has been surprisingly discovered that the fungus grows well at a temperature of 37° C.

In embodiments where the fungus is cultivated in liquid culture, the medium preferably comprises dissolved oxygen in a range of about 0.01 mg/L to about 1000 mg/L. Preferably, the dissolved oxygen is in a range of about 0.1 mg/L to about 100 mg/L. More preferably, the dissolved oxygen is in a range of about 0.5 mg/L to about 40 mg/L.

In some embodiments, the microbes utilized in inoculation are grown in starter cultures using standard procedures. The standard procedures may vary according to the particular species selected.

Fungal Culture in a Vessel

Additional embodiments described herein relate to a fungal culture in a vessel, said culture comprising a liquid medium comprising a cellulose degrading fungus of the genus *Penicillium* in growth phase, a carbon source, a non-carbon nutrient mix, and $MgSO_4$ and/or other salt(s) of Mg at a concentration of at least 0.5 mM. In certain aspects, the culture is approximately 0, 2, 4, 6, 8, 10, 12, 14, 16, 18, 20, 22, 24, 30, 36, 42, 48, 54, 60, 66, 72, 78, 84, 90, 96, 120, 144, 168, 192, 216, 240 or more than 240 hours old. More preferably, the culture is about 96 hours old.

For growth of a culture in a vessel, the liquid medium can comprise a carbon source and a nitrogen source, wherein the ratio of carbon to nitrogen in the medium ranges from about 1:1 to about 1000:1. In a more preferred embodiment, the ratio of carbon to nitrogen in the medium ranges from about 20:1 to about 30:1, about 40:1, about 50:1, about 60:1, about 70:1, about 80:1, about 90:1 or about 100:1. In a more preferred embodiment, the ratio of carbon to nitrogen is 35:1 to about 55:1 for a balance of biomass yield and TAG yield. Where biomass yield is optimized, a ratio of about 20:1 to about 50:1, and preferably about 23:1 is typical. In other preferred embodiments where TAG yield is optimized, a larger ratio is typical, such as greater than about 100:1 and preferably greater than 200:1.

The carbon source in the liquid medium can be any suitable carbon source for growth of *Penicillium* species in a liquid medium. In certain embodiments, the carbon source can be one or more sugars of non-cellulosic origin. For example, the carbon source can comprise a mixture of sugars such as fructose, glucose and sucrose. In another exemplary embodiment, the carbon source can be a juice material such as cane juice and/or its condensates, up to and including dry solid obtained by complete evaporation. Furthermore, the carbon source can be free sugars transported in a plant material, such as free-running sap of plants. In another such aspect, the carbon source can comprise sugars derived from corn starch.

In other preferred embodiments, the carbon source comprises a cellulosic carbon source or a lysate thereof. For example, the cellulosic carbon source can be derived from a biomass cultivated specifically for biofuels production. Such cultivated cellulosic biomasses can include crops such as algae, grasses, agricultural crops such as corn, soy, sorghum and the like. In addition to these "cultivated cellulosic biomasses", the cellulosic carbon source may be obtained from cellulosic waste materials such as sawdust, wood chips, cellulose, algae, other biological materials, municipal solid waste (e.g., paper, cardboard, food waste, garden waste, etc.), and the like. In some preferred embodiments, the cellulosic carbon source is, or is a hydrolysate of, for example, an origin selected from the group consisting of sorghum grain, other grains, stover of different grains; forage and other grasses; oilseed crops and their stover; nut shells and hulls, including almond hulls; grape and other fruit pomace; yard and agricultural waste of plant origin; algae; wood and wood byproducts including wood chips, bark and sawdust; paper products; animal manure especially including the manure of herbivorous animals; and food waste, especially food waste of plant origin. However, it will be readily appreciated that any suitable cellulosic carbon source can be utilized with the cellulose degrading fungus described herein. In some embodiments the cellulosic carbon source comprises other materials including, but not limited to, lignocelluloses and lysates thereof as well as hemicelluloses and lysates thereof.

The liquid medium preferably comprises at least one dissolved nutrient selected from the group consisting of: glycerol, yeast extract, corn steep, mycelial cell extract from earlier cultures of the fungus, sulfates, nitrates, calcium salts, ammonium phosphate, magnesium sulfate, calcium chloride, ferric citrate, potassium sulfate, sodium acetate, sodium molybdate, copper sulfate, cobalt nitrate, zinc sulfate, boric acid and manganese chloride. It will be appreciated that other nutrients may be selected and added as needed.

In some embodiments, the liquid medium comprises $MgSO_4$ and/or other salt(s) of Mg at a concentration of at least 0.5 mM. Preferably, the concentration of $MgSO_4$ and/or other salt(s) of Mg is at least about 0.5, 1, 5, 10, 20, 30, 40 or at least 50 mM. It has been surprisingly discovered that in the absence of a surfactant such as Tween80, the addition of $MgSO_4$ and/or other salt(s) of Mg increases the amount of TAG produced by the culture when added at approximately 96 hours after inoculation of a culture and increases resultant biomass yield when added at time 0.

In some embodiments, the liquid medium provides for enhanced TAG accumulation in mixtures of fungal microbes. In some aspects, the nutrient mixture comprises increased iron (Fe) content. In certain aspects, the liquid medium comprises increased iron content wherein the iron content in the liquid medium is increased by a factor of about two to a factor of about thirty. In certain embodiments, the liquid medium comprises a concentration of about 0.1 mM, 0.2 mM, 0.3 mM, 0.4 mM, 0.5 mM, 0.6 mM, 0.7 mM, 0.8 mM, 0.9 mM to about 1 mM of iron per every 40 g/L of carbon source. In certain preferred embodiments, the liquid medium comprises a concentration of about 0.5 mM of iron per every 40 g/L of carbon source.

In some aspects, the liquid medium comprises Ni. In certain aspects, $NiSO_4$ is added in a concentration ranging from about 0.1 ppm, 1 ppm, 10 ppm, 100 ppm to about 1000 ppm. In certain aspects, $NiSO_4$ is added in a concentration ranging from about 1 ppm to about 100 ppm of $NiSO_4$. In certain aspects, $NiSO_4$ is added in a concentration ranging from about 1.1 ppm to about 11.1 ppm of $NiSO_4$.

In some aspects, the liquid medium comprises malic acid. In certain aspects, malic acid is added to the liquid medium before the culture is inoculated. In certain aspects, the malic acid concentration in the liquid medium prior to inoculation is about 0.01%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or about 10%.

In some aspects, the liquid medium comprises one or more amino acids selected from the group consisting of: L-isoleucine, L-tryptophan, and L-serine. In certain aspects, the one or more amino acids is added to the liquid medium at a concentration of about 1 mg/L, 10 mg/L, 50 mg/L, 100 mg/L, 200 mg/L, 300 mg/L, 400 mg/L, 500 mg/L, 600 mg/L, 700 mg/L, 800 mg/L, 900 mg/L, or about 1000 mg/L. In certain aspects, the one or more amino acids is added to the liquid medium at a concentration of about 400 mg/L.

In some embodiments, the liquid medium comprises a non-ionic detergent such as Polysorbate 80 (Tween80), Polysorbate 20 (Tween20), deoxycholate, Brij-35 and the like. Preferably, the non-ionic detergent is Polysorbate 80 (Tween80). More preferably, the liquid medium comprises Polysorbate 80 (Tween80) at a concentration of at least 0.001%, 0.01% or at least 0.1%. It has been surprisingly found that when $MgSO_4$ and/or other salt(s) of Mg is added at about 96 hours in conjunction with Tween80 added at about time 0, both biomass and TAG yields are enhanced.

In preferred embodiments, the liquid medium is at a pH of at about 3.0 to about 7.0. More preferably, the pH is about 4.5 to about 6.5. More preferably, the pH is about 5.5. Maintaining a pH that is lower than neutral can help prevent contaminating growth of other organisms such as bacteria. In preferred embodiments, the temperature of the nutrient medium can range from about 20° C. to about 50° C. More preferably, the temperature can range from about 28° C. to about 43° C. Where biomass and/or TAG yield is to be optimized, the optimal temperature can range from about 36° C. to about 39° C., with a preferred temperature of 37° C.

The liquid medium preferably comprises dissolved oxygen in a range of about 0.01 mg/L to about 1000 mg/L. Preferably, the dissolved oxygen is in a range of about 0.1 mg/L to about 100 mg/L. More preferably, the dissolved oxygen is in a range of about 0.5 mg/L to about 40 mg/L.

In a preferred embodiment, the fungal culture in a vessel comprises *Penicillium menonorum*. Preferably, the fungal culture in a vessel comprises a fungus of the genus *Penicillium*, the species being the same as NRRL deposit Accession No: 50410. In one preferred embodiment, the fungus can have a 5.8S ribosomal RNA gene sequence with sequence identity with the nucleic acid of SEQ ID NO: 1. In another preferred embodiment, the fungus can have an ITS1 sequence having sequence identity with the nucleic acid of SEQ ID NO: 2. In still another preferred embodiment, the fungus can have an ITS2 sequence having sequence identity with the nucleic acid of SEQ ID NO: 3. In yet another preferred embodiment, the fungus can have a 28S rRNA gene sequence having sequence identity with the nucleic acid of SEQ ID NO: 4. More preferably, the sequence identity with SEQ ID NOs: 1, 2, 3 and/or 4 is at least 10%, 20%, 30%, 40%, 50%, 60%, 70%, 80%, 85%, 86%, 87%, 88%, 89%, 90%, 91%, 92%, 93%, 94%, 95%, 96%, 97%, 98% or at least 99% nucleotide sequence identity with the nucleic acid of SEQ ID NO: 1, 2, 3 and/or 4.

The resultant lipids may include any molecular forms having a straight-chain saturated hydrocarbon portion. Such lipids are desirable because the straight-chain saturated hydrocarbon portion is relatively easy to convert to vehicle fuel.

Lipids include TAGs and wax esters. Mono- or di-unsaturated hydrocarbon chains are also found in lipids and are suitable for conversion to alkanes, albeit with the requirement of additional hydrogen to saturate them.

The resultant aromatic compounds include any molecular forms having carbon ring structures. Examples of preferred aromatics include xylenes, methyl benzenes, and others.

In some embodiments, TAG and aromatic production is promoted by maintaining the microbes in a high-carbon, low-nitrogen environment, and providing aeration and/or agitation. As is understood, optimizing the percentage of feedstock carbon converted to TAG or aromatics requires controlling the growth of the microbial culture so as to reduce the carbon consumed by cell replication and metabolic activity and to increase the carbon consumed in producing TAG and aromatics. This can be done by controlling the ratio of non-carbon nutrient to carbon in the feedstock, as well as by controlling other parameters such as pH, temperature, dissolved oxygen, carbon dioxide production, fluid shear, and the like. In some embodiments, one or more measurements of these parameters may be used to determine when to harvest produced TAG. For example, in one embodiment, the carbon or nitrogen availability may be changed in order to switch the culture from a rapid growth mode to a TAG accumulation mode. In other words, one or more of these parameters may have a value associated with or which is indicative of desired TAG production.

In a preferred embodiment, nitrogen availability is controlled such that when nitrogen is depleted, the production of TAG is stimulated. In some embodiments, nitrogen can be added during a culture run as needed to control the production of TAG.

For example, in some embodiments, fluid shear is controlled by either moving the reactor vessel as a whole (e.g., by rocking it back and forth at a controlled frequency) or by means of mechanical agitators immersed in the fluid (e.g., any of a variety of paddle or stirrer shapes driven by electrical motors at a controlled frequency).

In some embodiments, aeration or oxygenation of the fluid is accomplished by any number of means, including via entrainment of air due to turbulence caused by mechanical agitation of the fluid and via bubbling or sparging air, air enriched with oxygen, or pure oxygen through the fluid.

In some embodiments, oxygenation of the fluid is accomplished by using turbulence to mix oxygen present in the head space of a bioreactor into the liquid medium. As used herein, the head space is the space above the liquid medium that is occupied by gas and vapor. Without wishing to be bound by any particular theory, use of the head space for oxygenating the fluid is believed to result in a significantly reduced cost of operating an aerobic culture.

Figure 2:
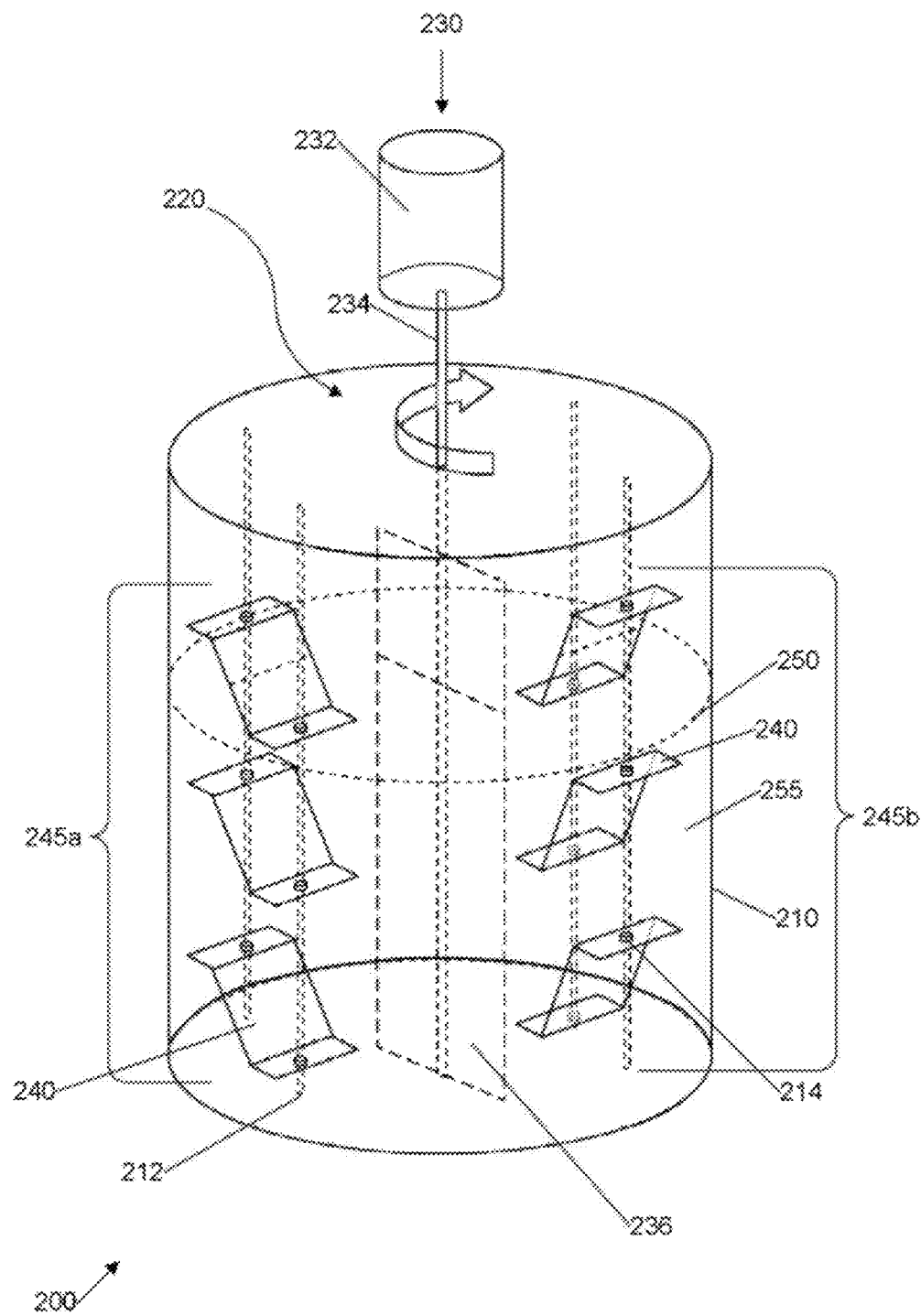
FIG. 2 is a schematic of a bioreactor system for oxygenating fluid according to an embodiment of the invention.
Figure 3:
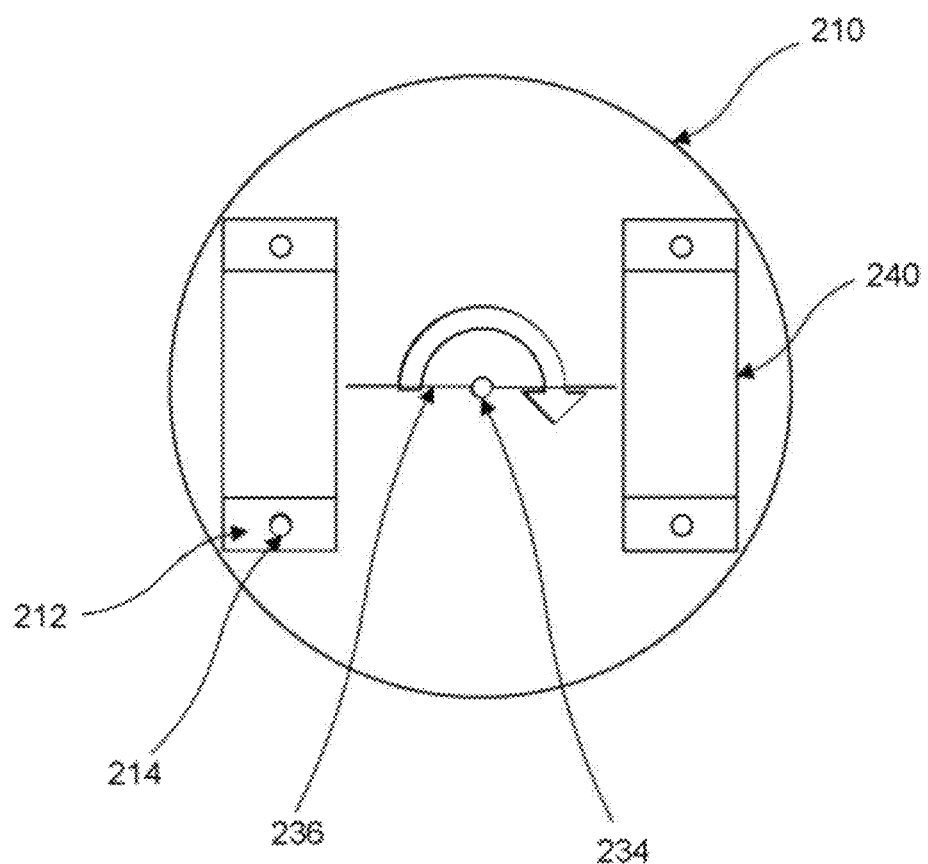
FIG. 3 is a top view of the bioreactor system of FIG. 2.
Figure 4:
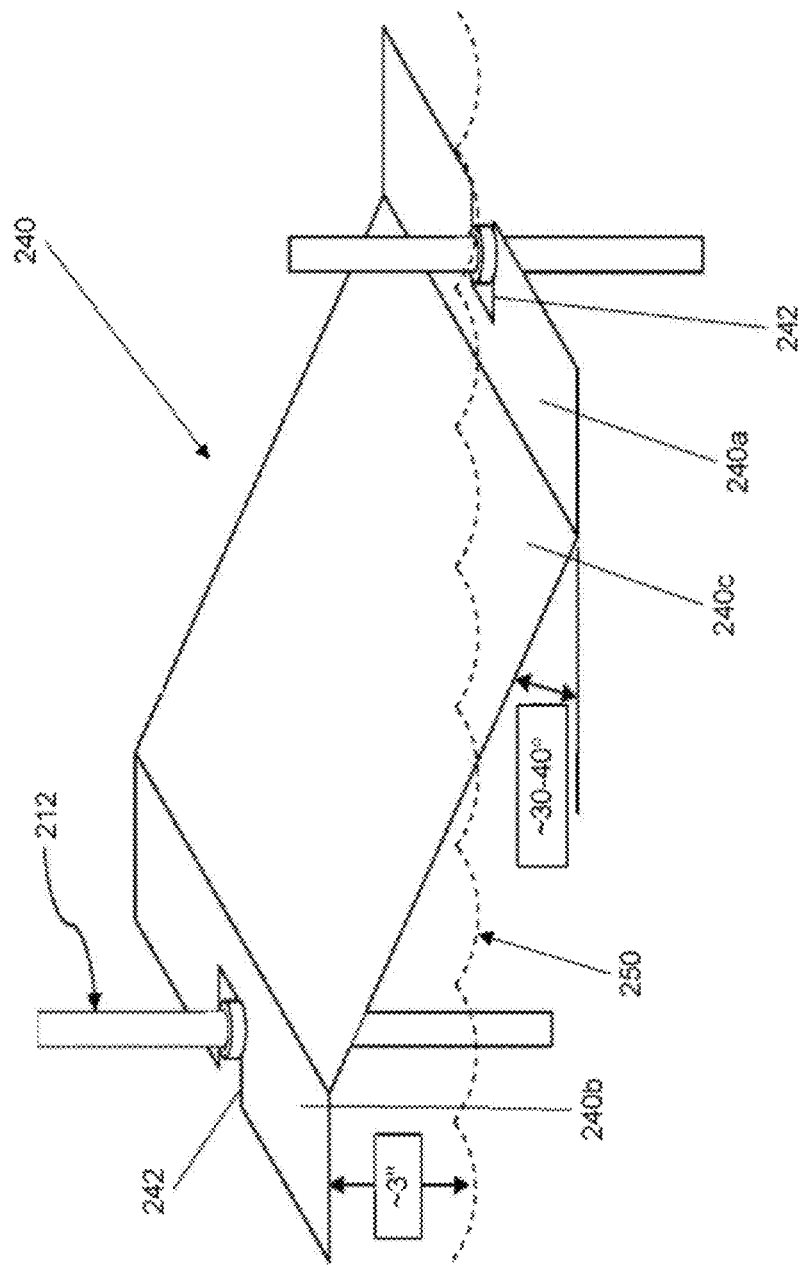
FIG. 4 is a close up of fluid flow ramps, as shown in FIG. 2.

For example, referring to FIGS. 2-4, a bioreactor system 200 including a bioreactor vessel 210 with head space 220 is shown. As presented, bioreactor vessel 210 is rotationally symmetric about a vertical axis (not shown). System 200 includes a rotary agitation mechanism 230 along the vertical axis that forces a strongly azimuthal flow when rotated (in accordance with the arrow shown). For example, as shown, the rotary agitation mechanism 230 includes a drive motor 232, a drive shaft 234, and a paddle 236.

As shown in FIG. 2, a rotary drive motor 232 and drive shaft 234 and a largely vertical paddle 236 induce a strongly azimuthal flow of the liquid medium about the center axis of the vessel 230. In one embodiment, a flat paddle 236 with a radius equal to about one quarter of the bioreactor vessel 210's diameter and rotating at up to 150 revolutions per minute is adequate to drive the desired flow. The clearance between the outer radius of the paddle 236 and the inner edge of the ramps 240 (discussed below) may be minimized, while avoiding impact, rubbing or other physical contact between the two structures.

It will be appreciated that impeller and paddle design and the flow direction are not restricted to those set forth above and in the Figures, but that any suitable type of impeller or flow direction can be used.

In an alternative embodiment, the agitation paddle 236 may be curved, so as to be concave in the direction of rotation. While not wishing to be bound by any particular theory, this change in paddle shape may generate a stronger azimuthal flow for a given paddle speed.

A set of stationary ramps 240 that force fluid to flow along a path with variable vertical displacement are also shown within bioreactor vessel 210. These ramps 240 may be secured to the vessel 210 via support rods 212 and fasteners 214.

As shown in FIGS. 2 and 4, the topmost set of ramps 240 breaks the liquid surface 250 and is designed to cause a substantial fraction of the liquid to flow up the ramp 240 and fall back into the bulk liquid 255. The turbulent re-entry of this "waterfall" entrains gases from the head space 220 back into the bulk liquid 255. The lower-level ramps 240 ensure that the gases thus entrained at the surface are well-mixed at all depths in the vessel 210.

In some embodiments, sets of ramps 240 may be used at various depths to deflect the fluid flow in the vertical direction to generate strong fluid mixing vertically. In such embodiments, the topmost set of ramps 240 may extend across the mean liquid surface 250. It may be desirable to make sure that the topmost ramp's highest surface is low enough to allow most of the fluid to reach and flow over the top, falling freely back into the liquid 255 and entraining gas from the head space 220, such as shown in FIG. 4.

In order to achieve improved results, ramps 240 having ramp angles of 30 to 40 degrees, with the highest point of the topmost ramp 240 extending approximately 3 inches above the mean liquid surface 250 may be used. In such embodiments, the ramp's width is approximately one quarter of the bioreactor vessel 210's diameter, and two stacks of ramps 240 placed diametrically opposite each other may be adequate to achieve the desired mixing and oxygenation.

In one embodiment, ramps 240 having two horizontal end plates 240 a, b and a flat, tilted plate section 240c that generates the vertical flow are used. The end plates 240 a, b may include slots 242 for ease of mounting on vertical support rods 212 fixed in the bioreactor vessel 210 (for example, by being fixed to a top cover plate). The slots 242 may also allow the ramp angle to be adjusted straightforwardly.

As shown in FIG. 2, two stacks 245a, 245b, of ramps 240 located diametrically opposite each other in the vessel 210 are shown. However, any number of stacks of ramps 240 (e.g., three, four, etc.) may be used. Also, as shown, there are two or three ramps 240 in each stack 245a, 245b.

As described above, each ramp 240 includes three planar sections—two horizontal end plates 240a, 240b and one tilted plate 240c. The ramp 240 can be made concave, or given raised lips along its inside and outside edges, to form a trough that can send a larger proportion of the liquid over the lip of the waterfall, for increased gas entrainment efficiency. Alternatively, the ramp 240 can be made as a single, continuous, curvilinear form along the azimuthal direction, rather than out of three planar segments.

As shown in FIG. 4, the ramps 240 are rectangular in shape. In some embodiments, ramps 240 are made as circular arc segments to fit into the circular bioreactor vessel 210, catch a larger fraction of the azimuthal flow and maintain a constant separation from the paddle 236.

Referring back to FIG. 2, support rods 212 may be vertical and threaded for receiving threaded fasteners 214 to mount and hold the ramps 240. The ramps 240 could equally be attached to the side wall of the bioreactor vessel 210 via fastening means such as welding, adhesives, or through fasteners (e.g., bolts or rivets). In one embodiment, pair of rods 212 is used to support each stack of ramps 240, however, any number of rods 212 may be used.

As shown in FIG. 2, the rods 212 are suspended from a top plate (not shown) of the bioreactor vessel 210. However, rods 212 may alternatively or also be anchored to the bottom of the bioreactor vessel 210. In some embodiments, the rods 212 are attached to a collapsible mechanism (not shown) that can be inserted through a smaller opening at the top of the vessel 210.

The bioreactor vessel 210 is shown as a flat-bottomed bioreactor. However, the design may be adapted to a conical-bottom bioreactor or a dish-bottom reactor by reducing radii of ramps 240 and the agitation paddle 236 appropriately, as a function of height in the conical or dished portion of the reactor.

Paddles 236, shafts 234, ramps 240, rods 212 and fasteners 214 may be made of any material that (a) is strong enough to withstand peak and average loadings experienced in course of operation over time, (b) does not corrode in the aqueous culture with its range of pH and temperature, including sterilization temperatures, and (c) does not either interfere with the bioactivity of the culture or suffer biocorrosion. The default material is stainless steel, but many different plastics and metals may be used.

In an alternative embodiment, herein referred to as a "fountain reactor", the reactor simply pumps the aqueous culture into a fountain in the head space, for example, via a spray fan, with the liquid entraining gases as it falls back into the main body of the liquid. The pump can be a submersible, large-diameter pump to avoid clogging or fouling by the biomass generated by the culture. In some embodiments, the pump is mounted outside or external to the reactor.

Fungal Culture in a Bioprocess Reactor (Bioreactors)

In some embodiment, the bioreactor vessel described hereinabove comprises a cellulose degrading fungus. For example, the bioreactor vessel may be a vessel as shown in FIGS. 2-4. However, it will be readily appreciated that any suitable bioreactor system suitable for the growth of a cellulose degrading fungus can be used.

As used herein, the terms "bioprocess reactor", "bioreactor vessel", "bioreactor" and the like can refer to a vessel in which a biological process such as fermentation and microbial growth takes place. Bioprocess reactors such as those described herein and in the Figures are useful for the growth of cellulose degrading fungi such as the fungus described herein as *Penicillium menonorum*. For example, in a bioprocess reactor, any one of a number of variables such as temperature, pH, percent oxygenation, stir rate, and the like may be monitored and/or controlled to achieve a desired growth condition.

Some bioreactor embodiments described herein include a bioprocess reactor comprising a cellulose degrading fungus of the genus *Penicillium* growing in a liquid medium, wherein the fungus comprises at least 5% triacylglyceride by dry weight. In a preferred embodiment, the cellulose degrading fungus of the genus *Penicillium* comprises at least about 10% to about 50% triacylglyceride by dry weight. In a more preferred embodiment, the cellulose degrading fungus of the genus *Penicillium* comprises at least about 25% to about 50% triacylglyceride by dry weight. In a preferred embodiment, the fungus comprises *Penicillium menonorum*.

In preferred embodiments, the bioprocess reactor comprises a fungus of the genus *Penicillium* growing in a liquid medium, said liquid medium comprising a carbon source and a nitrogen source, wherein the ratio of carbon to nitrogen in the medium ranges from about 1:1 to about 1000:1.

In another embodiment, the bioprocess reactor comprises a cellulosic carbon source or a lysate thereof having a cellulose degrading fungus of the genus *Penicillium* growing thereon. In a preferred embodiment, the cellulosic carbon source is present in a liquid medium.

In another embodiment, the bioprocess reactor comprises a cellulose degrading fungus of the genus *Penicillium* growing in a liquid medium, wherein the liquid medium comprises at least one lipid selected from the group consisting of triacylglycerides and phospholipids. In some embodiments, the liquid medium further comprises glycerol.

It will be readily understood that the terms glycerol, glycerin and glycerine and like terms refer to the same organic compound, also known as propan-1,2,3-triol or 1,2,3-trihydroxypropane.

For growth of a culture in a bioprocess reactor, the liquid medium can comprise a carbon source and a nitrogen source, wherein the ratio of carbon to nitrogen in the medium ranges from about 1:1 to about 1000:1. In a more preferred embodiment, the ratio of carbon to nitrogen in the medium ranges from about 20:1 to about 30:1, about 40:1, about 50:1, about 60:1, about 70:1, about 80:1, about 90:1 or about 100:1. In a more preferred embodiment, the ratio of carbon to nitrogen is 35:1 to about 55:1 for a balance of biomass yield and TAG yield. Where biomass yield is optimized, a ratio of about 20:1 to about 50:1, and preferably about 23:1 is typical. In other preferred embodiments where TAG yield is optimized, a larger ratio is typical, such as greater than about 100:1 and preferably greater than 200:1.

The carbon source in the liquid medium in the bioprocess reactor can be any suitable carbon source for growth of *Penicillium* species in a liquid medium. In certain embodiments, the carbon source can be one or more sugars of non-cellulosic origin. For example, the carbon source can comprise a mixture of sugars such as fructose, glucose and sucrose. In another exemplary embodiment, the carbon source can be a juice material such as cane juice and/or its condensates, up to and including dry solid obtained by complete evaporation. Furthermore, the carbon source can be free sugars transported in a plant material, such as free-running sap of plants. In another such aspect, the carbon source can comprise sugars derived from corn starch.

In other preferred embodiments, the carbon source comprises a cellulosic carbon source or a lysate thereof. For example, the cellulosic carbon source can be derived from a biomass cultivated specifically for biofuels production. Such cultivated cellulosic biomasses can include crops such as algae, grasses, agricultural crops such as corn, soy, sorghum and the like. In addition to these "cultivated cellulosic biomasses", the cellulosic carbon source may be obtained from cellulosic waste materials such as sawdust, wood chips, cellulose, algae, other biological materials, municipal solid waste (e.g., paper, cardboard, food waste, garden waste, etc.), and the like. In some preferred embodiments, the cellulosic carbon source is, or is a hydrolysate of, for example, an origin selected from the group consisting of sorghum grain, other grains, stover of different grains; forage and other grasses; oilseed crops and their stover; nut shells and hulls, including almond hulls; grape and other fruit pomace; yard and agricultural waste of plant origin; algae; wood and wood byproducts including wood chips, bark and sawdust; paper products; animal manure especially including the manure of herbivorous animals; and food waste, especially food waste of plant origin. However, it will be readily appreciated that any suitable cellulosic carbon source can be utilized with the cellulose degrading fungus described herein. In some embodiments the cellulosic carbon source comprises other materials including, but not limited to, lignocelluloses and lysates thereof as well as hemicelluloses and lysates thereof.

In some embodiments, the liquid medium in the bioprocess reactor preferably comprises at least one dissolved nutrient selected from the group consisting of glycerol, yeast extract, corn steep, mycelial cell extract from earlier cultures of the fungus, sulfates, nitrates, calcium salts, ammonium phosphate, magnesium sulfate, calcium chloride, ferric citrate, potassium sulfate, sodium acetate, sodium molybdate, copper sulfate, cobalt nitrate, zinc sulfate, boric acid and manganese chloride. It will be appreciated that other nutrients may be selected and added as needed.

In some embodiments, the liquid medium in the bioprocess reactor comprises $MgSO_4$ and/or other salt(s) of Mg at a concentration of at least 0.5 mM. Preferably, the concentration of $MgSO_4$ and/or other salt(s) of Mg is at least about 0.5, 1, 5, 10, 20, 30, 40 or at least 50 mM. It has been surprisingly discovered that in the absence of a surfactant such as Tween80, the addition of $MgSO_4$ and/or other salt(s) of Mg increases the amount of TAG produced by the culture when added at approximately 96 hours after inoculation of a culture and increases resultant biomass yield when added at about time 0.

In some embodiments, the liquid medium in the bioprocess reactor provides for enhanced TAG accumulation in mixtures of fungal microbes. In some aspects, the nutrient mixture in the bioprocess reactor comprises increased iron (Fe) content. In certain aspects, the liquid medium in the bioprocess reactor comprises increased iron content wherein the iron content in the liquid medium is increased by a factor of about two to a factor of about thirty. In certain embodiments, the liquid medium in the bioprocess reactor comprises a concentration of about 0.1 mM, 0.2 mM, 0.3 mM, 0.4 mM, 0.5 mM, 0.6 mM, 0.7 mM, 0.8 mM, 0.9 mM to about 1 mM of iron per every 40 g/L of carbon source. In certain preferred embodiments, the liquid medium in the bioprocess reactor comprises a concentration of about 0.5 mM of iron per every 40 g/L of carbon source.

In some aspects, the liquid medium in the bioprocess reactor comprises Ni. In certain aspects, $NiSO_4$ is added in a concentration ranging from about 0.1 ppm, 1 ppm, 10 ppm, 100 ppm to about 1000 ppm. In certain aspects, $NiSO_4$ is added in a concentration ranging from about 1 ppm to about 100 ppm of $NiSO_4$. In certain aspects, $NiSO_4$ is added in a concentration ranging from about 1.1 ppm to about 11.1 ppm of $NiSO_4$.

In some aspects, the liquid medium in the bioprocess reactor comprises malic acid. In certain aspects, malic acid is added to the liquid medium before the culture is inoculated. In certain aspects, the malic acid concentration in the liquid medium prior to inoculation is about 0.01%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, or about 10%.

In some aspects, the liquid medium in the bioprocess reactor comprises one or more amino acids selected from the group consisting of: L-isoleucine, L-tryptophan, and L-serine. In certain aspects, the one or more amino acids is added to the liquid medium at a concentration of about 1 mg/L, 10 mg/L, 50 mg/L, 100 mg/L, 200 mg/L, 300 mg/L, 400 mg/L, 500 mg/L, 600 mg/L, 700 mg/L, 800 mg/L, 900 mg/L, or about 1000 mg/L. In certain aspects, the one or more amino acids is added to the liquid medium at a concentration of about 400 mg/L.

In some embodiments, the liquid medium in the bioprocess reactor comprises a non-ionic detergent such as Polysorbate 80 (Tween80), Polysorbate 20 (Tween20), deoxycholate, Brij-35 and the like. Preferably, the non-ionic detergent is Polysorbate 80 (Tween80). More preferably, the liquid medium comprises Polysorbate 80 (Tween80) at a concentration of at least 0.001%, 0.01% or at least 0.1%. It has been surprisingly found that when $MgSO_4$ and/or other salt(s) of Mg is added at about 96 hours in conjunction with Tween80 added at about time 0, both biomass and TAG yields are enhanced.

In preferred embodiments, the liquid medium in the bioprocess reactor is at a pH of at about 2.5 to about 10. More preferably, the pH is about 3.0 to about 7.0. More preferably, the pH is about 4.5 to about 6.5. More preferably, the pH is about 5.5. Maintaining a pH that is lower than neutral can help prevent contaminating growth of other organisms such as bacteria. In preferred embodiments, the temperature of the nutrient medium can range from about 20° C. to about 50° C. More preferably, the temperature can range from about 28° C. to about 43° C. Where biomass and/or TAG yield is to be optimized, the optimal temperature can range from about 36° C. to about 39° C., with a preferred temperature of 37° C. It has been surprisingly discovered that the fungus grows well at a temperature of 37° C.

In certain preferred embodiments, the medium in the bioprocess reactor preferably comprises dissolved oxygen in a range of about 0.01 mg/L to about 1000 mg/L. Preferably, the dissolved oxygen is in a range of about 0.1 mg/L to about 100 mg/L. More preferably, the dissolved oxygen is in a range of about 0.5 mg/L to about 40 mg/L.

In another preferred embodiment, the bioprocess reactor comprises *Penicillium menonorum*. Preferably, the fungal culture comprises a fungus of the genus *Penicillium*, the species being the same as NRRL deposit Accession No: 50410.

In one preferred embodiment, the fungus in the bioprocess reactor can have a 5.8S ribosomal RNA gene sequence with sequence identity with the nucleic acid of SEQ ID NO: 1. In a preferred embodiment, the fungus can have an ITS1 sequence having sequence identity with the nucleic acid of SEQ ID NO: 2. In a preferred embodiment, the fungus can have an ITS2 sequence having sequence identity with the nucleic acid of SEQ ID NO: 3. In a preferred embodiment, the fungus can have a 28S rRNA gene sequence having sequence identity with the nucleic acid of SEQ ID NO: 4. More preferably, the sequence identity with SEQ ID NOs: 1, 2, 3 and/or 4 is at least 10%, 20%, 30%, 40%, 50%, 60%, 70%, 80%, 85%, 86%, 87%, 88%, 89%, 90%, 91%, 92%, 93%, 94%, 95%, 96%, 97%, 98% or at least 99% nucleotide sequence identity with the nucleic acid of SEQ ID NO: 1, 2, 3 and/or 4.

In some embodiments of the bioprocess reactors described herein, the bioprocess reactor further comprises an impeller rotating at a stir rate of about 1 RPM to about 1200 RPM. In some embodiments, the stir rate is about 1 RPM to about 300 RPM. In certain aspects the stir rate is about 20 to about 100 RPM. In certain aspects, the stir rate is about 60-70 RPM.

An example illustrating benefits of the bioreactor system 200 will now be described.

Example

Experiments were conducted on two 100-liter microbial cultures that were identical except for the oxygenation mechanism. The first culture (e.g., control sample) used 10 liters per minute of oxygen-enriched air, pumped through a perforated-tube sparger at the bottom of the bioreactor. The second culture (e.g., experimental sample) used the "waterfall" method exemplified by bioreactor system 200 and pumped the same 10 liters per minute of identically enriched air into the headspace.

On the fourth day of the culture, at a time of maximal growth (and, hence, maximal oxygen consumption), the dissolved oxygen in the sparged reactor (e.g., control sample) measured 8 to 9 milligrams of $O_2$ per liter of liquid, while the dissolved oxygen in the waterfall reactor (e.g., experimental sample) measured 17 to 18 milligrams per liter. Based on this example, the waterfall reactor produced a higher dissolved oxygen content (by 8-10 milligrams per liter) than a traditional sparged reactor.

In accordance with some embodiments, using the waterfall method includes optionally, enriching the gas in the head space of an aqueous bioreactor by pumping in air enriched with oxygen by a commercially available oxygen enricher. Because the enriched gas is being pumped into a large manifold, there is no requirement of high pressure pumping, in contrast to approaches relying on bubbling (sparging).

Benefits of the using the bioreactor vessel 210 and the waterfall method include:
No high output pressure oxygen enrichment required;
No high-pressure gas flow required;
No perforated or sintered sparging apparatus to suffer biofouling;
No moving parts other than the rotary agitator;
Very low cost;
Highly effective oxygenation of the culture, even under heavy growth conditions that are often susceptible to oxygen deprivation.

Figure 5:
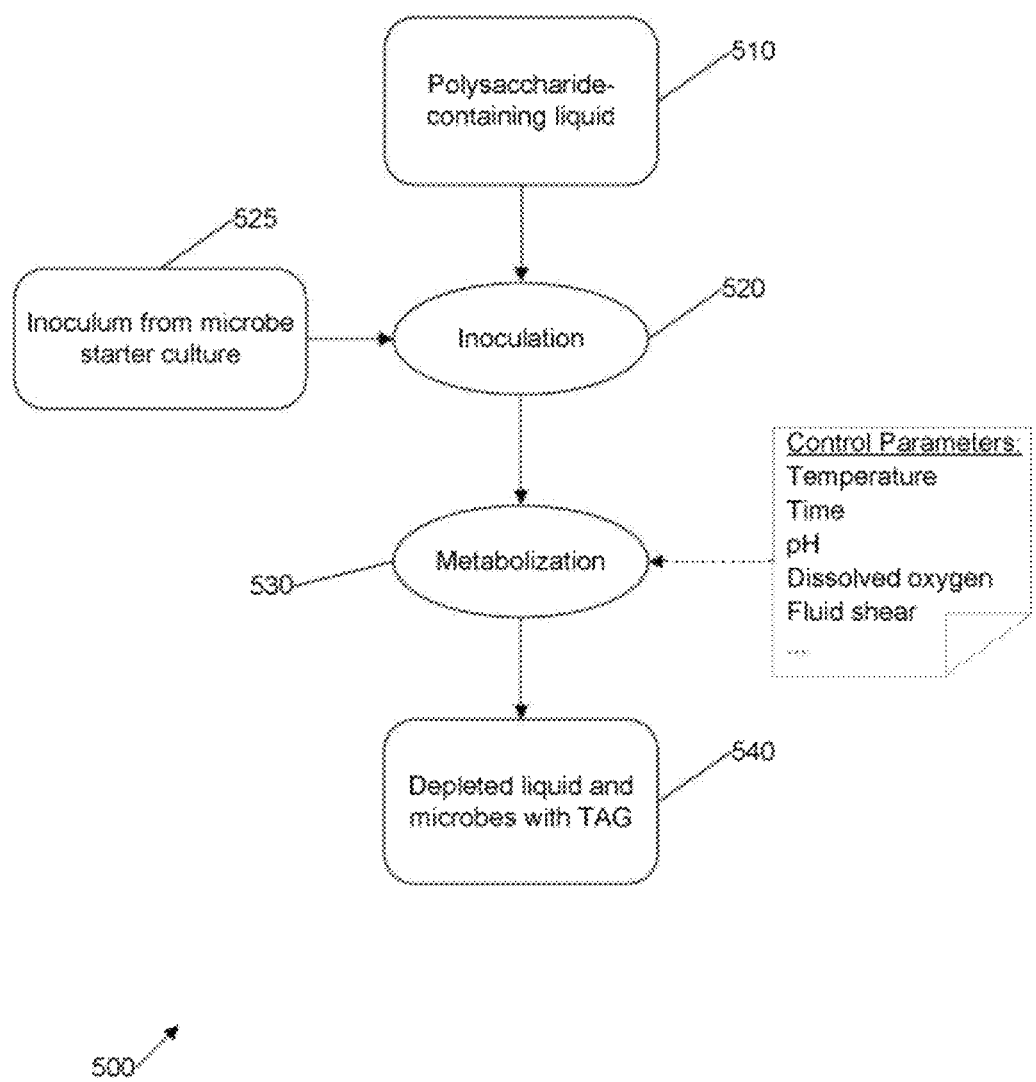
FIG. 5 is a flow chart of an inoculation and fermentation process according to an embodiment of the invention.

Referring now to FIG. 5, a flow chart of an inoculation and fermentation process 500 in accordance with an embodiment of the invention is shown. The inoculation and fermentation process 500 includes a receiving stage 510 for receiving the liquid output 144 from the pretreatment process 100 and an inoculation step 520 that adds a starter culture 525 of the selected microorganism or microorganisms to the liquid 144 to form a mixture at the inoculation step 520. The selected microorganisms may be a single species or strain, or a combination of multiple species or strains. In a preferred embodiment, the microorganism is *Penicillium menonorum*. The inoculum can be in the form of vegetative cells or spores.

The inoculation and fermentation process 500 also includes a metabolization step 530, which takes the mixture and controls parameters such as temperature, pH, dissolved oxygen, and fluid shear using appropriate methods known in the art. During this metabolization step 530, the microorganisms proliferate and metabolize the feedstock, creating intracellular inclusions of lipids in the form of triacylglycerides (TAG). At the end of this stage (e.g., as determined by defined values of one or more of the parameters of time, pH, dissolved oxygen or others) the metabolization is stopped, yielding a depleted fluid 540 with suspended microbes containing TAG.

Figure 6:
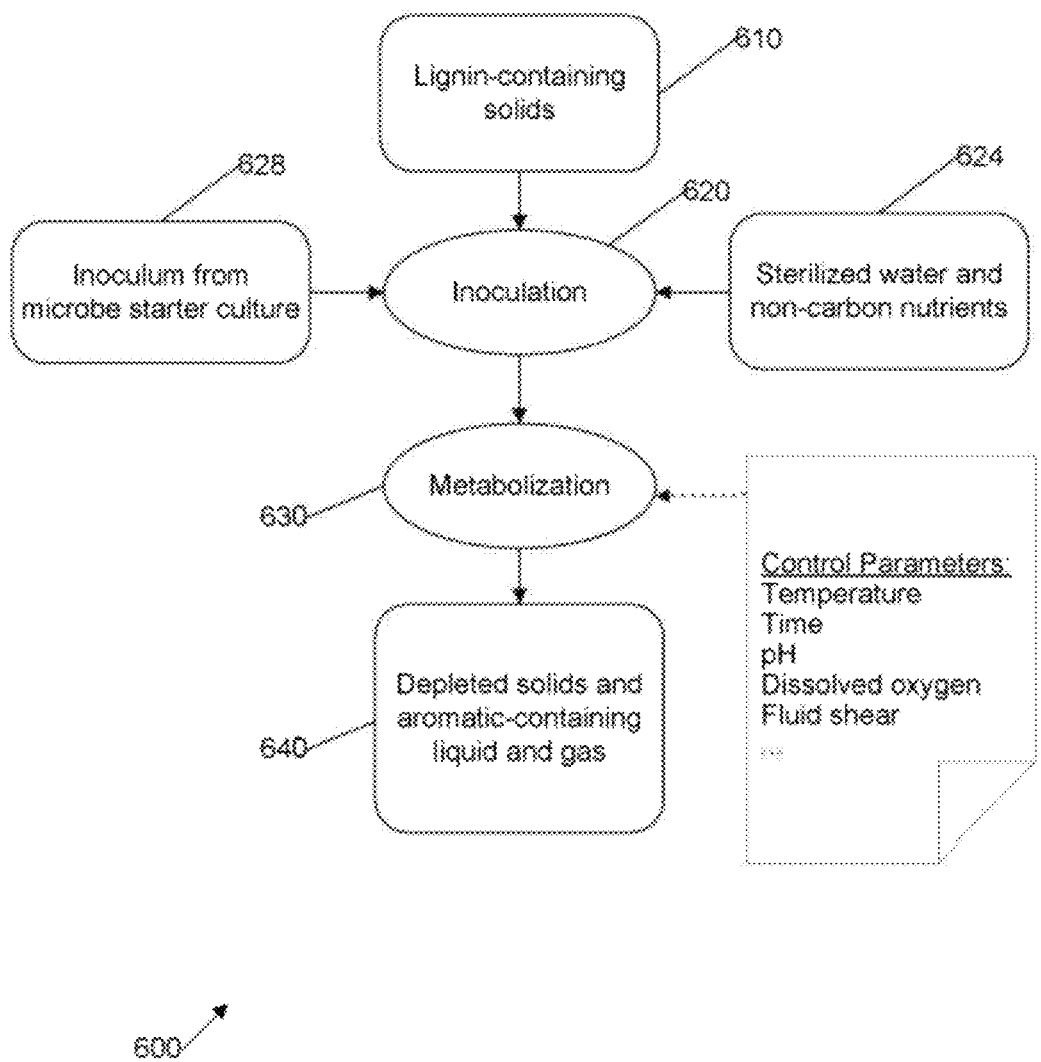
FIG. 6 is a flow chart of an inoculation and fermentation process according to an embodiment of the invention.

Referring now to FIG. 6, a flow chart of an inoculation and fermentation process 600 in accordance with an embodiment of the invention is shown. The inoculation and fermentation process 600 includes a receiving stage 610 for receiving the solid portion of the pretreated feedstock 148 from the pretreatment process 100 and an inoculation step 620, in which the portion of feedstock 148 is mixed with sterilized water and non-carbon nutrients 624 and a starter culture of specially selected microorganisms suited to decomposing the lignin 628. The selected microorganisms may be a single species or strain, or a combination of multiple species or strains. In a preferred embodiment, the microorganism is *Penicillium menonorum*. The inoculum can be in the form of vegetative cells or spores.

The inoculation and fermentation process 600 also includes a metabolization step 630, which takes this mixture and controls parameters such as temperature, pH, dissolved oxygen, and fluid shear using appropriate methods known in the art. During this metabolization step 630, the microorganisms proliferate and metabolize the feedstock, breaking the lignin down into smaller aromatic compounds that are released into the solution. At the end of this stage (e.g., as determined by defined values of one or more of the parameters of time, pH, dissolved oxygen or others) the metabolization is stopped, yielding a mixture 640 containing depleted solids, microbes, and gas and liquid containing the desired aromatic compounds.

(3) Harvesting and Product Extraction

Extracting product from a fermentor is different, depending on whether the product is TAG or protein-rich fungal biomass. Each is considered in turn. In both cases, however, choosing the proper time to harvest will maximize yield. Measurements such as pH, dissolved oxygen, carbon dioxide production, remaining carbon nutrient concentration, and the like can be used to determine the optimal harvest time.

In particular, it has been surprisingly found that during the growth phase (also called "log phase" and "linear phase") of the culture, when microbial cells are dividing rapidly, protein content of the cells is high (approximately 32.2% of cell dry weight, (cdw)) and TAG content is low (typically approximately <6% of cdw). When the nitrogen in the culture medium is low or exhausted but sufficient carbohydrates still exist in the medium, the log phase ceases and a nutritional stress phase commences, where the cells accumulate TAG. In this regime, not only does TAG increase as a percentage of cdw, but the protein content decreases. In fact, the protein content decreases not only as a fraction of total cdw, but also as a fraction of the dry weight of cells after the TAG has been extracted (residual cdw). Accordingly, the ideal time to harvest depends on whether fuel or animal feed is the primary market driving force, and on what amount of protein as a percentage of cdw is desired for the animal feed, and harvest time can be adjusted as market demands change. If fuel is the main desired product, harvest can be delayed until TAG forms >30% of cdw; then the protein content may be as low as <15% of residual cdw. If protein-rich feed is the primary product, harvest can be performed right at the end of the growth phase, when TAG forms <6% of cdw and protein content may be as high as 25% of residual cdw, or higher. If a lower protein content feed is desired, harvest can be performed after the end of the growth phase but before the amount of TAG reaches its maximum percentage of cdw.

Harvesting and Extracting TAG

The liquid medium in the digesters has provided TAG-producing microbes with nourishment, allowing the microbes to flourish and reproduce. These microbes store TAG in intracellular structures. The first step, accordingly, is to harvest or collect the cellular biomass from the liquid medium. Because cells tend to form multicellular agglomerations hundreds of micrometers in size, harvesting may be performed by screening, sieving, centrifugation, or filtration. The multicellular agglomerations may be the result of the filamentatious nature of the microbes, as discussed above. The result of this step is a mass of cellular biomass with remaining excess water, e.g. wet biomass.

In some embodiments, the wet biomass is dried after the collecting step. For example, gross excess water may be removed mechanically from the wet biomass by pressing through a roller press, squeezed, or wrung. Alternatively, water may be removed using a fan separator, screw press, or by spray harvesting techniques. The wet biomass may then be further dried using a vacuum oven, lyophilizer, or other common drying equipment. It should be recognized that when using a vacuum oven, for example, the temperature should be controlled so that TAG is not or is only minimally hydrolyzed (e.g., drying at temperatures of about less than 80° C.). In some embodiments, lyophilizing is selected as the drying means because it has the effect of increasing the surface area to volume ratio of the biomass, which makes subsequent extraction more efficient. In some embodiments, flash freezing (e.g., via immersion in liquid nitrogen or −80° C. freezer) is used to break up the cell structures, improving efficiency of subsequent extraction, and possibly partially disrupting the cells.

Because the wet biomass may be degraded when the water is removed, drying the biomass both efficiently and gently is preferred. In order to achieve gentle drying, processes in accordance with an embodiment generally do not expose or minimize exposure of the biomass to heat.

Additionally, when drying biomass, it may be important to avoid releasing live microbes or spores into the environment. Consequently, microbial cultivators and processors often ensure that any biological material is sterilized prior to release in the atmosphere, drain or trash. In an embodiment, the described apparatus and method ensure biological material is sterilized, thereby avoiding releasing live contaminants (e.g., microbes or spores) into the environment.

In some embodiments, a method of drying the biomass includes exposing the biomass to low-humidity air or dry, inert gas and then sterilizing the air, thereby killing any microbes or spores or other biological material entrained in the air.

Figure 7A:
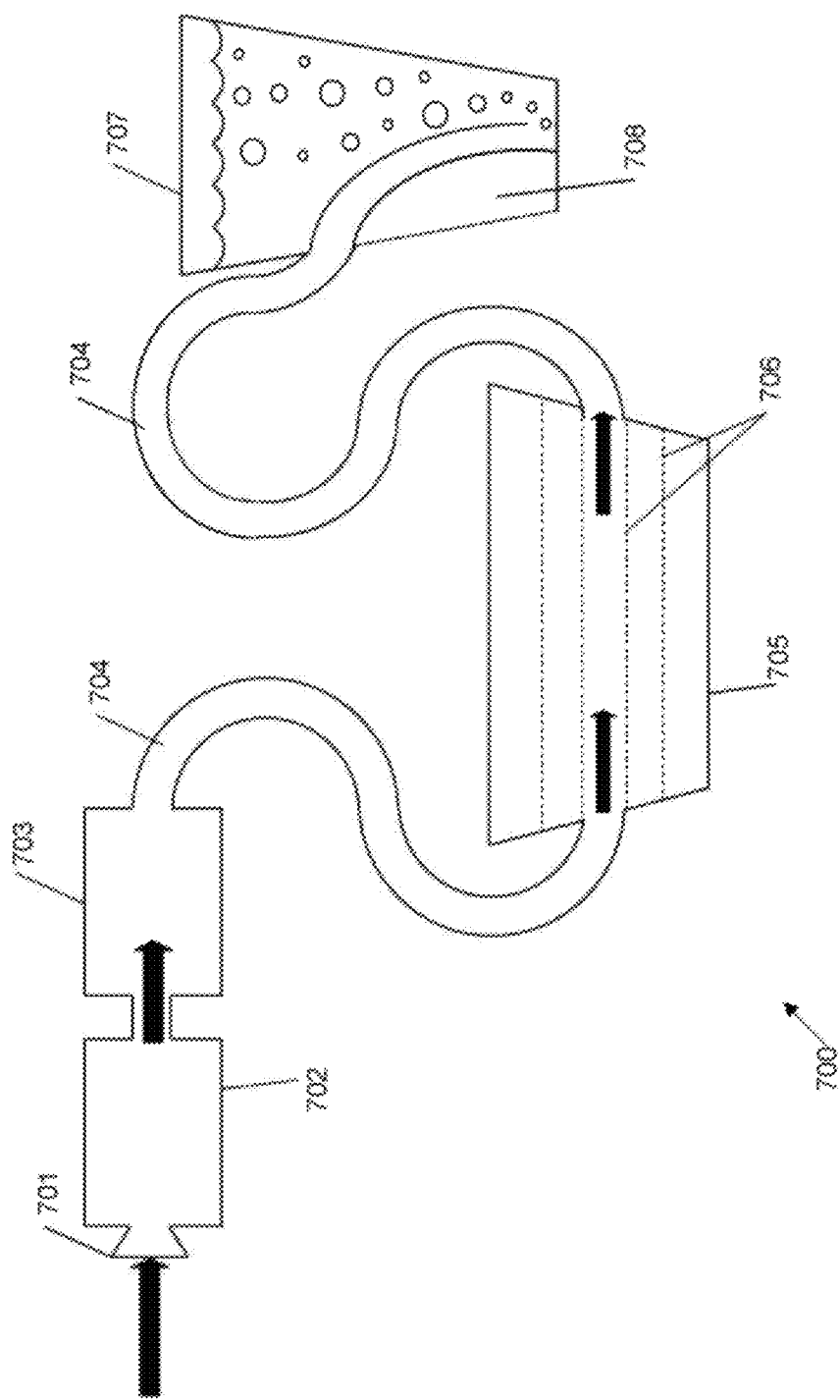
FIGS. 7A and 7B are block diagrams of a system for drying biomass according to an embodiment of the invention.

An exemplary system for drying the biomass is provided in FIG. 7A. As shown in FIG. 7A, system 700 includes a dehumidifying chamber 702, a drying chamber 705, and a sterilization chamber 707. System 700 may additionally include a fluid intake section 701, a fluid pump 703, and hoses or connectors 704. Drying chamber 705 may include one or more perforated drying screens 706. Sterilization chamber 707 may include a sterilization or biocide fluid 708. As used herein, "fluid" includes gases such as air, as well as liquids.

In one embodiment, the system 700 first provides low-humidity air or dry inert gas via fluid intake section 701 and dehumidifying chamber 702. Then, the dry inert gas or low-humidity air is moved past the biomass to be dried in drying chamber 705. The air or inert gas is thereafter sterilized in sterilization chamber 707, thereby killing any microbes or spores or other biological matter entrained in the air. The arrows indicate air flow.

As is appreciated, the source of low-humidity air may be a dehumidifier. Alternatively, when a dry, inert gas is used, the source may be a compressed gas cylinder filled with a suitable gas such as nitrogen or helium.

Drying chamber 705 may be any container such as a metal or plastic box with sufficient volume to contain the material (e.g., biomass) to be dried. Drying chamber 705 typically includes an input duct or port coupled to the source of low-humidity air (e.g., dehumidifying chamber 702), and an output duct or port coupled to the sterilization chamber 707. The material to be dried may be arranged or spread thinly upon on one or more shelves or platforms (e.g., perforated drying screens 706) supported within the drying chamber 705, preferably arranged so that the air passes freely over the material. The shelves may be porous or grid-like to permit evaporation from both top and bottom surfaces of the material.

Figure 7B:
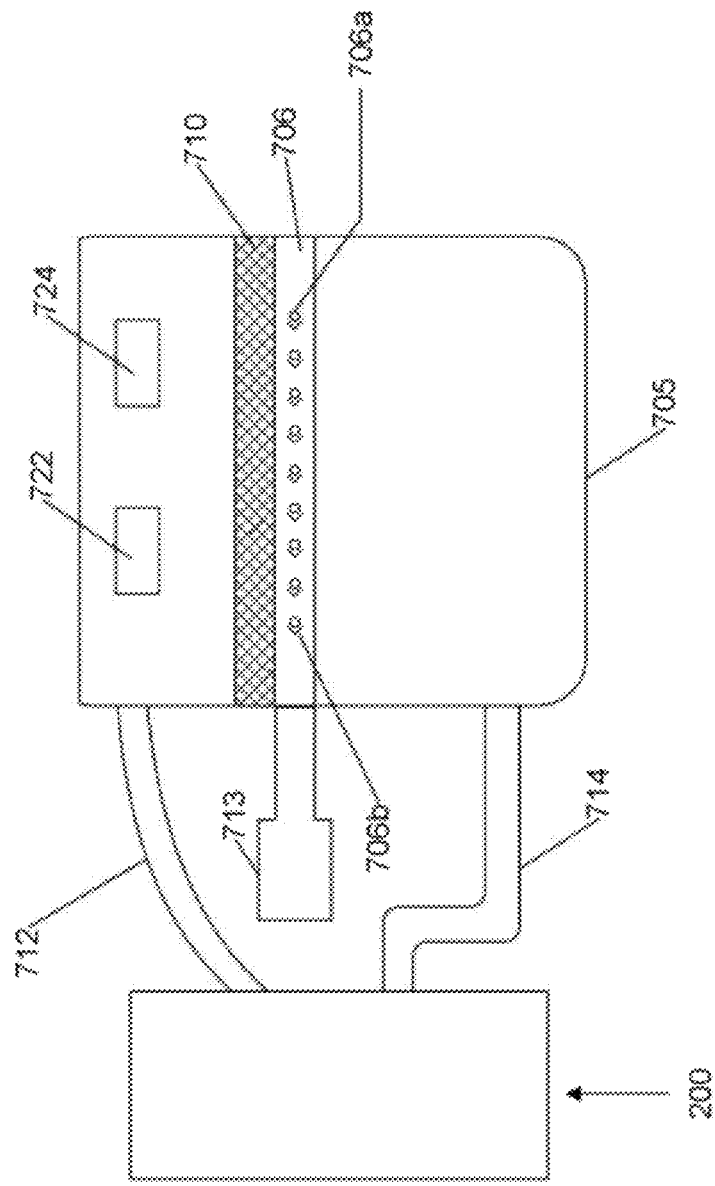

Referring to FIG. 7B, in some embodiments, perforated drying screens 706 have a mesh screen 710 placed on top of the drying screens 706. Thereafter, the biomass may be added to the drying chamber 705 by pumping the biomass into the top of the drying chamber 705 from bioreactor 200 via tubing and/or pump 712. Air may be bubbled up from beneath the drying screens 706 from an air source 713, where each perforation 706a may have a microchannel 706b attaching it to the air source 713 (e.g., a bubbler). In one embodiment, the air source 713 is the same air source as used in FIG. 7A. The air flowing through the screens 706 helps the liquid to flow out of the biomass and through the mesh 710. Additionally, in some embodiments, drying chamber 705 includes a stirrer 722 and/or a heater 724 in the space above mesh 710. While not wishing to be bound by any particular theory, it is believed that stirrer 722 assists the liquid flowing through mesh 710, while trapping the biomass on mesh 710, and heater 724 provides drying to the biomass. Any resulting liquid may be pumped out of the bottom of the tank 705 via tubing and/or pump 714 and recycled back into bioreactor 200. In some embodiments, a dehumidifier and various types of heat can also be used (e.g., heat the air, heat the tank, etc.).

Upon reaching a sufficient dryness, the biomass can be removed from drying chamber 705 via traditional mechanical or pneumatic means and/or automated means. For example, suitable removal means include, but are not limited to, scoops, conveyors, valves, and compressed air or vacuum.

Additionally, while not explicitly shown, the drying chamber may comprise a tumble-dry configuration whereby the material to be dried is agitated with the low-humidity air. Alternatively, any other drying configuration which results in a moisture content of less than or equal to about 10% may be used.

Sterilization chamber 707 may be any container such as a metal or plastic box with sufficient volume to contain the means for sterilizing the air and any entrained biological matter. Sterilization chamber 707 typically includes an input port or duct coupled to the exit port of the drying chamber 705, and an output port or duct through which sterilized air is released. The output port may include a filter (not shown) to further contain biological material.

The sterilizing means may be any means for killing microbes, spores, or other biological matter entrained in the passing air, prior to release. The sterilizing means may be a drum or bucket containing water and bleach through which the air is bubbled. Alternatively, the sterilizing means may be ultraviolet lamps producing radiation with sufficient intensity and wavelength to kill cells in the passing air.

As provided above, system 700 may additionally include a fluid pump 703. Fluid pump 703 may be any type of blowing apparatus such as a fan or pump. Fluid pump 703 preferably provides sufficient airflow volume to effectively remove moisture from the material to be dried, and sufficient pressure to pass the air through the chambers 702, 705, 707, including the sterilization chamber 707 back-pressure if present. In some embodiments, fluid pump 703 includes multiple fans or blowers. For example, dehumidifying chamber 702 may include a built-in fan to urge air into the drying chamber 705, and another fan may be positioned between the drying chamber 705 to urge air into the sterilization chamber 707 and a third fan may be arranged to draw air out of the sterilization chamber 707 and pass the air through a filter before release.

The system 700 may be open-cycle or closed-cycle. An open-cycle system draws air from the environment or other source such as a compressed-gas cylinder, dehumidifies it if necessary, passes it over the material to be dried, sterilizes it, and then releases it to the environment. A closed-cycle system passes the air from the sterilization chamber 707 back to the dehumidifying chamber 702 for re-use. The open-cycle system is simpler, but the closed-cycle system may be more economical when using an alternative gas such as nitrogen for drying.

In an exemplary embodiment, to remove water from the wet biomass, the biomass is spread in a thin layer across the screens 706. Perforations in the screens allow the air or dry gas access to both upper and lower surfaces of the biomass layer. The chamber 705 is then closed.

An air dehumidifier or cylinder of compressed dry gas (e.g., nitrogen or helium—any gas that is inert with respect to biological materials) is connected to a fan or pump 703 to force it through the drying chamber 705, largely parallel to the layers. The fan or pump 703 may be connected at the inlet, forcing the air through; or it may be connected at the outlet, using a vacuum to draw the air through; or both. The dry gas or dehumidified air flowing past the layer effectively draws water from the biomass.

During this process, the gas may pick up microscopic amounts of biological material, including cells of the microbial culture, as it passes through the drying chamber 705. To prevent spreading of potentially undesirable organisms, in one embodiment, the air is bubbled through a reservoir of bleach or other biocidal liquid upon exiting the drying chamber 705 in sterilization chamber 707 before being released into the atmosphere. Alternatively, the air may pass through a region of intense ultraviolet illumination that also acts as a biocide. This alternative embodiment is shown in FIG. 8, described below.

Figure 8:
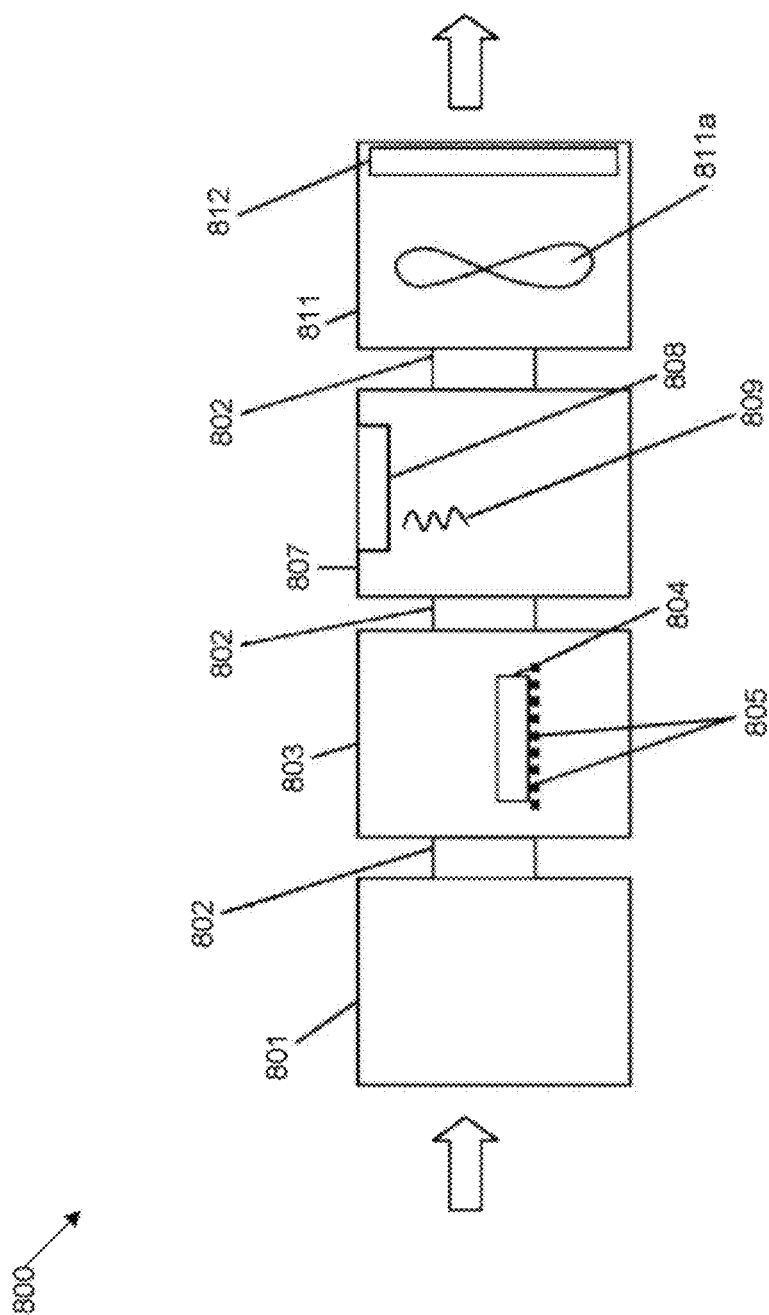
FIG. 8 is a block diagram of a system for drying biomass according to an alternative embodiment of the invention.

Referring now to FIG. 8, in an alternate embodiment, system 800 includes a dehumidifying chamber 801, a drying chamber 803, and a sterilization chamber 807. System 800 may additionally include hoses or connectors 802. Drying chamber 803 may include one or more perforated drying screens or perforated shelves 805 for drying material to be dried 804. Sterilization chamber 807 may include an ultraviolet lamp 808 that emits ultraviolet radiation 809, which is used to sterilize the air. System 800 may additionally include a fan 811 having blades 811*a* and filter 812. Once again, arrows indicate air flow.

As provided above, a system or apparatus for removing moisture from biological material includes: a source of low-humidity air or dry inert gas, a first enclosure containing material to be dried (e.g., drying chamber), a second enclosure containing means for sterilizing matter (e.g., sterilization chamber), means for moving the air through the first enclosure so as to evaporatively dry the material to be dried, and means for moving the air from the first enclosure through the second enclosure so as to sterilize the air prior to release.

Benefits of the system for drying the biomass include:
No exposure to elevated temperatures, preserving stability of heat-sensitive chemicals of interest;
Rapid drying due to thin-layer distribution of the biomass, exposure to dehumidified air or dry gas, and reliance on continuous air flow; rapid drying can also serve to stop cells' metabolic activities, potentially preserving TAG stores.
Reduced energy expenditure by avoiding either heating or active cooling of materials; and
Active control of the exhaust gas to prevent the spread of undesirable organisms.

Because extracted liquids may contain residual nutrients, as well as microbial cells that escaped harvest, this fluid may be recycled. For example, in one embodiment, the recycled fluid constitutes a portion of the starting broth (e.g., liquid medium) of the next production cycle. Because the fluid may also contain metabolites released by the reproducing and digesting microbes, and high metabolite concentration may inhibit the succeeding production cycle, in one embodiment, the recycled fluid is treated to neutralize the metabolites. The recycled fluid may also, in some instances, be sterilized.

Following collection, the cellular biomass is exposed to a cell disruptor, e.g., means for extracting the lipid material from within the cells. In some embodiments, the cell disruptor frees lipids from microbe cells using, for example, heat, cold, ultrasound or chemical disruption (lysis) of the cells. In one embodiment, chemical lysis includes utilizing a polar/non-polar solvent mix, such as a chloroform-methanol solution to lyse the cells and their internal structures. Without wishing to be bound by any particular theory, it is believed that the methanol disrupts the cell, and the chloroform extracts the lipids. Other chemical solvents, including but not limited to methylene chloride and chloroform-methanol, as well as hexane-ethanol and others, may also be used in chemical lysis and lipid extraction.

Once the lipids have been released from the intracellular structure, they are separated from the cellular debris. In some embodiments, a mechanical lipid separator is used. For example, a doctor-blade to guide a floating lipid-rich mass from the top of the mixture, a sump to draw heavier components from the bottom of the lipid separator, or other port means depending on the properties of the lipids may be used. Furthermore, in some embodiments, a chemical solvation process may be utilized to provide a higher level of purity of TAG. For example, using light alkane solvents like hexane or heptanes yields a purer TAG than mechanical means because phospholipids and proteins are typically insoluble or slightly soluble in alkanes. Consequently, the resulting TAG may be low in contamination by phosphorus and metals, which is desirable in some fuels.

After extraction of TAG, TAG is converted into hydrocarbons that may then be fractionated to form constituents of gasoline, diesel or jet fuel. Such conversion process is known to those skilled in the art. TAG can also be converted into alkyl esters such as methyl or ethyl to form biodiesel, via transesterification, in conversion process known to those skilled in the art.

Figure 9:
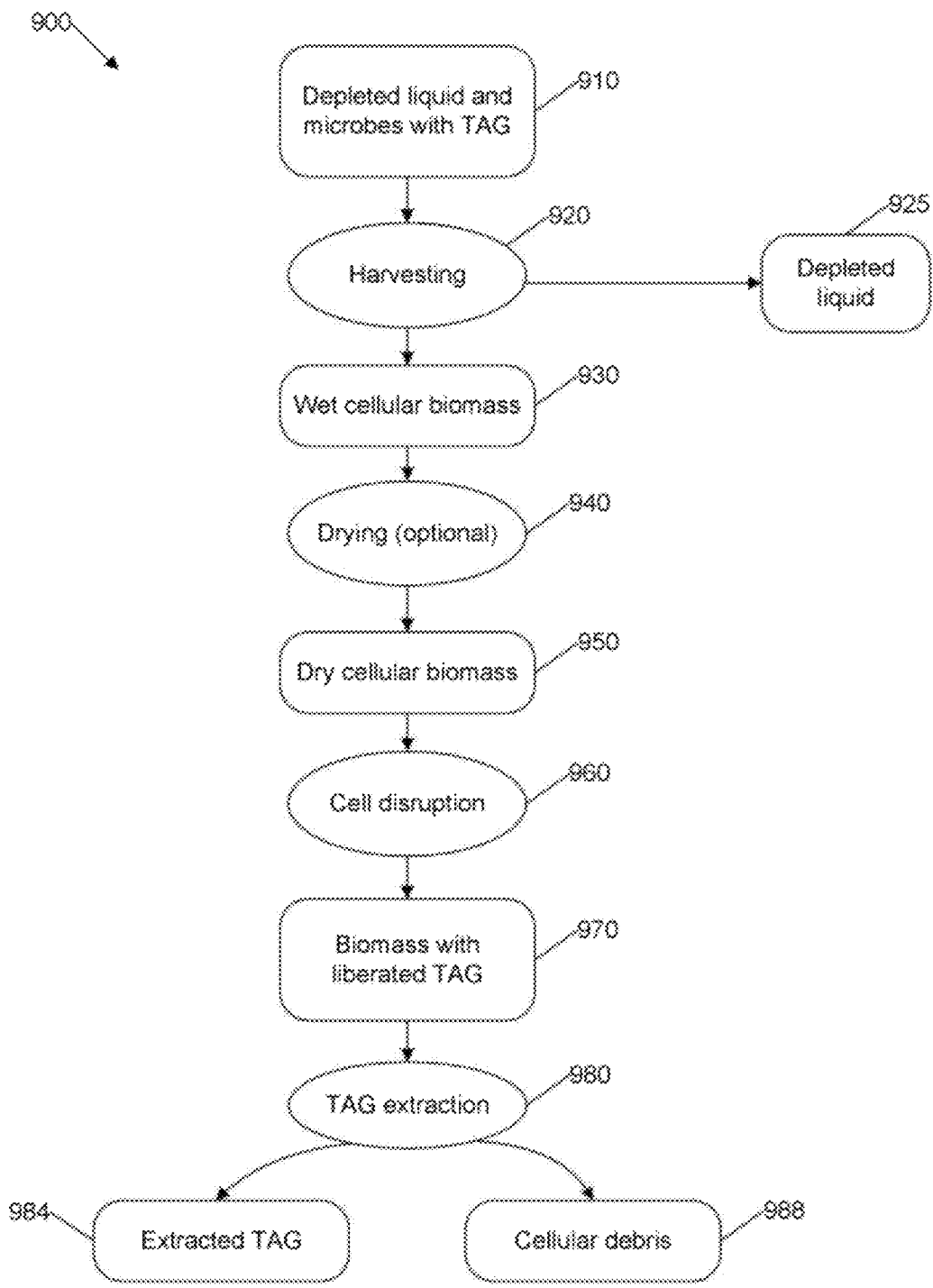
FIG. 9 is a flow chart of a microbial biomass collection process according to an embodiment of the invention.

Referring now to FIG. 9, a flow chart of a microbial biomass or intermediary product collection process 900 in accordance with an embodiment of the invention is shown. The microbial collection process 900 includes a receiving stage 910 for receiving the depleted fluid 540 with suspended microbes containing TAG from the inoculation and fermentation process 500 and uses one or more separation technique as described herein to harvest or collect 920 microbial biomass or intermediary product 930. In some embodiments, mechanical means such as one or more of filtration, sieving, screening, centrifugation or precipitation, is used to separate the microbial biomass 930 from the depleted liquid 925. Accordingly, in a preferred embodiment, it is advantageous to use *P. menonorum* because its filamentatious structure enables the use of simple, inexpensive mechanical separators. In contrast, non-aggregating unicellular microbes would require more expensive means, such as centrifuges.

In some embodiments, the depleted liquid 925 is recycled as part of the water 134 added to the feedstock in the pretreatment stage 100 of FIG. 1. The depleted liquid 925 may require buffering, not shown, to mitigate the otherwise inhibitory effect of metabolites secreted by the microbes in the metabolization stage 530 of FIG. 5.

The microbial biomass or intermediary product 930 consists of wet microbial biomass. Accordingly, a drying step 940 may optionally be performed, to speed the extraction process.

The drying step 940 may utilize heating in an oven, heating and evacuation in a vacuum oven, lyophilization, with or without use of a cryogenic liquid, or other desiccation means. The result of this step 940 is a dry cellular biomass or intermediary product 950.

Either the wet biomass 930 or the dry biomass 950 is then subjected to a cell disruption step 960 that breaks up the cell structures to render the TAG accessible to chemical solvents. The cell disruption step 960 may utilize methods including one or more of mechanical, thermal, or chemical methods. For example, mechanical disruption methods may include one or more of ultrasonic, cutting, pressing, rolling or abrading means. Thermal methods may use heated air or microwave energy, among other means. Chemical means use one of several chemical agents, including but not limited to chloroform, chloroform and methanol, or methylene chloride. The output of the cell disruption step 960 is a biomass with liberated TAG 970. Disrupting chemicals used in this step 960 may be captured, recovered and reused in a closed-cycle system. The microbial collection process 900 also includes a TAG extraction or initial purification step 980. In some embodiments, TAG extraction is performed via chemical solvation, using solvents including short-chain alkanes such as hexane and heptanes. Solvation is followed by decantation, repeated as needed to achieve the required yield of TAG. The output of the TAG extraction step 980 is extracted and purified TAG 984, along with cellular debris 988. Solvents used in this step 980 may be captured, recovered and reused in a closed-cycle system.

As stated above, the dry biomass contains the TAG within the microbial cells. The next step simultaneously disrupts the cell and extracts the TAG. In one embodiment, it relies on a mixture of solvents:
 a. a polar organic solvent (such as methanol, ethanol, isopropanol, or the like) to disrupt the cell structures and also extract the lipids, and
 b. a non-polar organic solvent (such as hexane, chloroform, methylene chloride, or the like) to extract the lipids efficiently.

In one embodiment, the solvent comprises a mixture of 10% methanol and 90% chloroform, by volume. In another embodiment, the solvent comprises a mixture of 10% ethanol and 90% hexane. Generally, the amount of methanol used can vary between 0% and 30% and the amount of ethanol used can vary between 0% and 30%. The nonpolar organic solvent completes the balance (e.g, so that the solvent mixture adds to 100%). The percentages need not be precise.

If the dry biomass is dense and jerky-like, it may be presoaked in the solvent mixture for several hours prior to the next step. If it is porous and fluffy, pre-soaking is not needed.

Cell disruption and TAG extraction proceeds by percolating hot solvent mixtures repeatedly through an amount of dry biomass. In the laboratory, this can be accomplished by a Soxhlet apparatus. At an industrial scale, the Soxhlet apparatus may be replaced by a system that is more robust and more energy-efficient at large scale. The underlying chemical principle remains the same: repeated exposure of the dry biomass to the hot pure solvents until nearly all the cells are disrupted and nearly all the liquids including neutral lipid TAG has escaped the biomass and gone into solution. In the Soxhlet apparatus, heat is applied to a reservoir of solvent, causing it to boil. The vapor rises until it condenses in a condenser cooled just below the boiling point. The condensate drips into a vessel containing the dry biomass (e.g., inside a filter). The hot, pure (and hence chemically more active) solvent level rises to submerge the biomass. In the Soxhlet process, the solvent is not only hot, but pure, because it is recondensed from vapor. Consequently, as more material is dissolved and extracted from the biomass, the material is collected in the reservoir and the solvent is boiled off, making the solvent pure when it again comes into contact with the biomass.

A siphon at the top of the vessel completely drains the vessel back into the solvent reservoir every time the liquid in the vessel reaches the top of the bend in the siphon. The biomass, constrained inside the filter, cannot flow with the draining fluid, so that the reservoir only collects fluid. This process can take several tens of minutes. During this time, the solvent mixture is both breaking down the cell structures and dissolving the TAG (and other intracellular molecules). When the vessel empties into the solvent reservoir, it now carries the solute with it. The cycle of evaporation-condensation-filling-dissolving-siphoning may be repeated until no further significant quantity of TAG is extracted from the biomass.

In some embodiments, the reservoir contains lipids (e.g., TAG), other biomolecules soluble in the polar solvent, and the solvent itself. An evaporation and distillation stage evaporates the solvent out of the mixture and condenses it, recapturing the solvent for reuse. What now remains in the reservoir is called crude TAG, since it may contain impurities.

A refining step includes treating the crude TAG in a solvent made of short-chain hydrocarbons such as heptane or mixtures of heptane with hexane or petroleum ether. One embodiment uses a 1:1 mixture of heptane and low-boiling-point petroleum ether (with boiling point between 40° C. and 60° C.). In other embodiments, the ratio of the solvents in the mixture can vary from about 1:100, about 1:10, or about 1:5 to about 5:1, about 10:1, or about 100:1.

This organic mixture is then decanted off or centrifuged from the insoluble residues and the organic layer can be washed with brine (NaCl in water) or other alkali salt solution. TAG remains dissolved in this solvent, while phospholipids, methanol, proteins and other impurities soluble in water are washed out. While not wishing to be bound by any particular theory, it is generally important to remove phospholipids, as many transport fuel specifications require low levels of phosphorus in the fuel.

In one embodiment, the brine wash is followed by a deionized water wash, which removes the NaCl. Following the water wash, the material may be dried using anhydrous sodium sulfate ($Na_2SO_4$) to remove residual water. Other analogous materials can also be used for the drying step. The sodium sulfate is thereafter removed by filtration (e.g., using filter paper in a sintered-glass filter funnel). The filtered liquid containing the extracted TAG is heated to evaporate the petroleum solvents (e.g., heptane and petroleum ether), which may be re-condensed for reuse. This process produces the purified TAG as an oily residue.

In one example embodiment, approximately 2 kg of wet biomass yields ≤1 kg of dry biomass. As an example, approximately 6 L of nonpolar-polar solvent mixture is used in the Soxhlet to extract the TAG. The approximately 6.1 L of TAG-solvent mixture is evaporated to yield approximately ≤0.1 L of TAG. Approximately 100 mL of heptane-petroleum ether solvent and similar quantities of brine and deionized water, and approximately 50 gm of sodium sulfate, anhydrous, are used to purify the TAG, yielding ≤0.1 L of final product. As can easily be appreciated, the above numbers do not represent the best possible TAG yield, but are merely examples of amounts that can be expected in a moderate-scale laboratory implementation of the process.

Figure 10A:
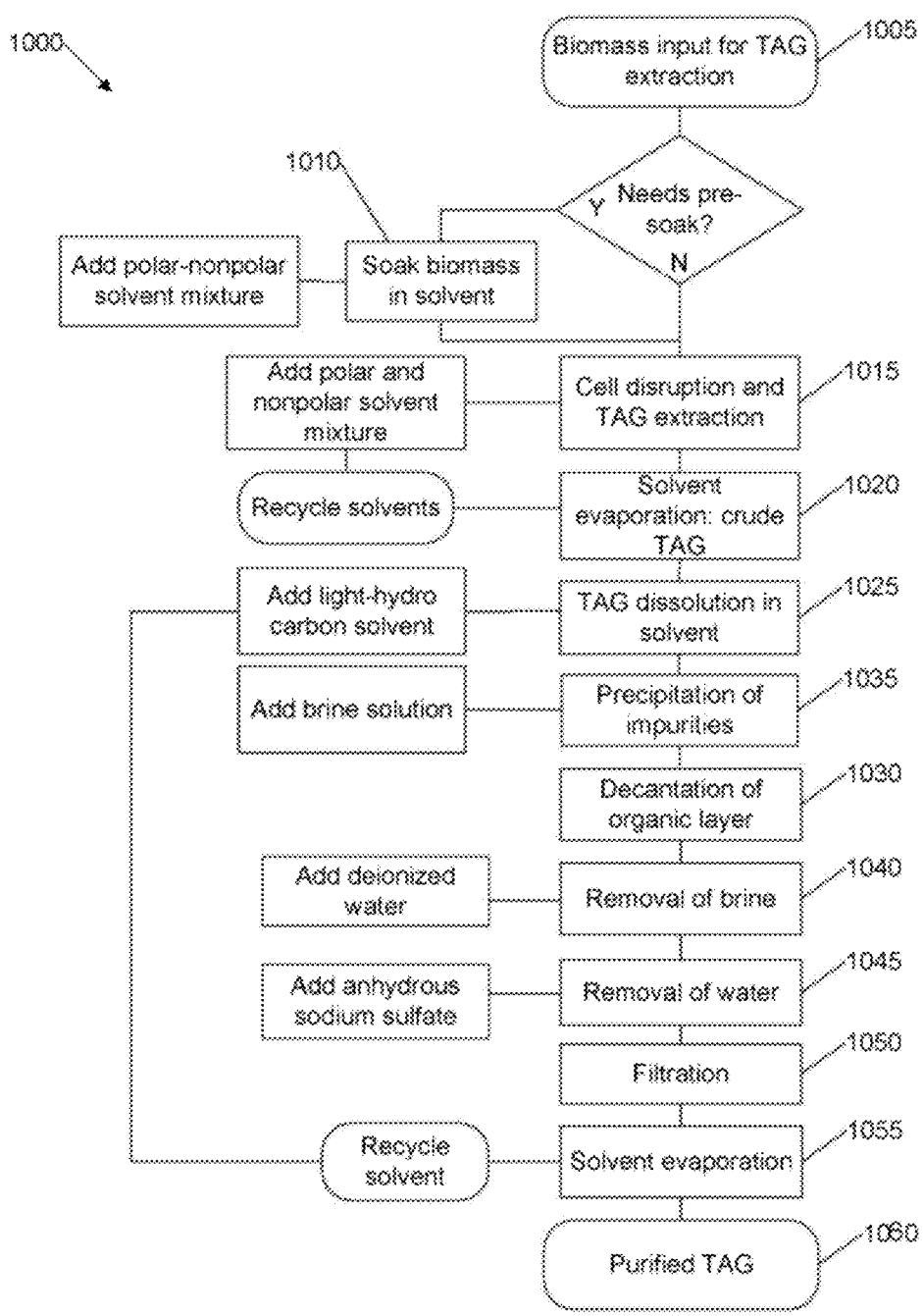
FIG. 10A is a flow chart of a TAG extraction and purification process according to an embodiment of the invention.

In accordance with some embodiments, a method of producing TAG includes a number of steps, each of which are shown in FIG. 10A. In one embodiment, a TAG extraction and purification process 1000 includes: starting with wet biomass in step 1005, optionally drying the biomass (not shown), optionally pre-soaking the dry biomass in a mixture of nonpolar and polar organic solvents in step 1010, disrupting the cell structures and extracting the TAG in step 1015 (e.g., via a Soxhlet-like process using a mixture of alcoholic and non-polar organic solvents), evaporating the solvent mixture from the collected liquid to produce crude TAG in step 1020, mixing the crude TAG with a light-hydrocarbon solvent in step 1025; decanting the organic layer off from the insoluble residue in step 1030, washing the resulting mixture (organic layer) with brine or other alkali salt solution and removing the water-soluble impurities in step 1035, washing the resulting liquid in water to remove the salt in step 1040, removing water from the resulting liquid using sodium sulfate, anhydrous, or other suitable material in step 1045; filtering the resulting liquid (e.g., using filter paper and a sintered-glass filter funnel) in step 1050; and evaporating the light-hydrocarbon solvents from the resulting liquid in step 1055, resulting in purified TAG in step 1060.

Figure 10B:
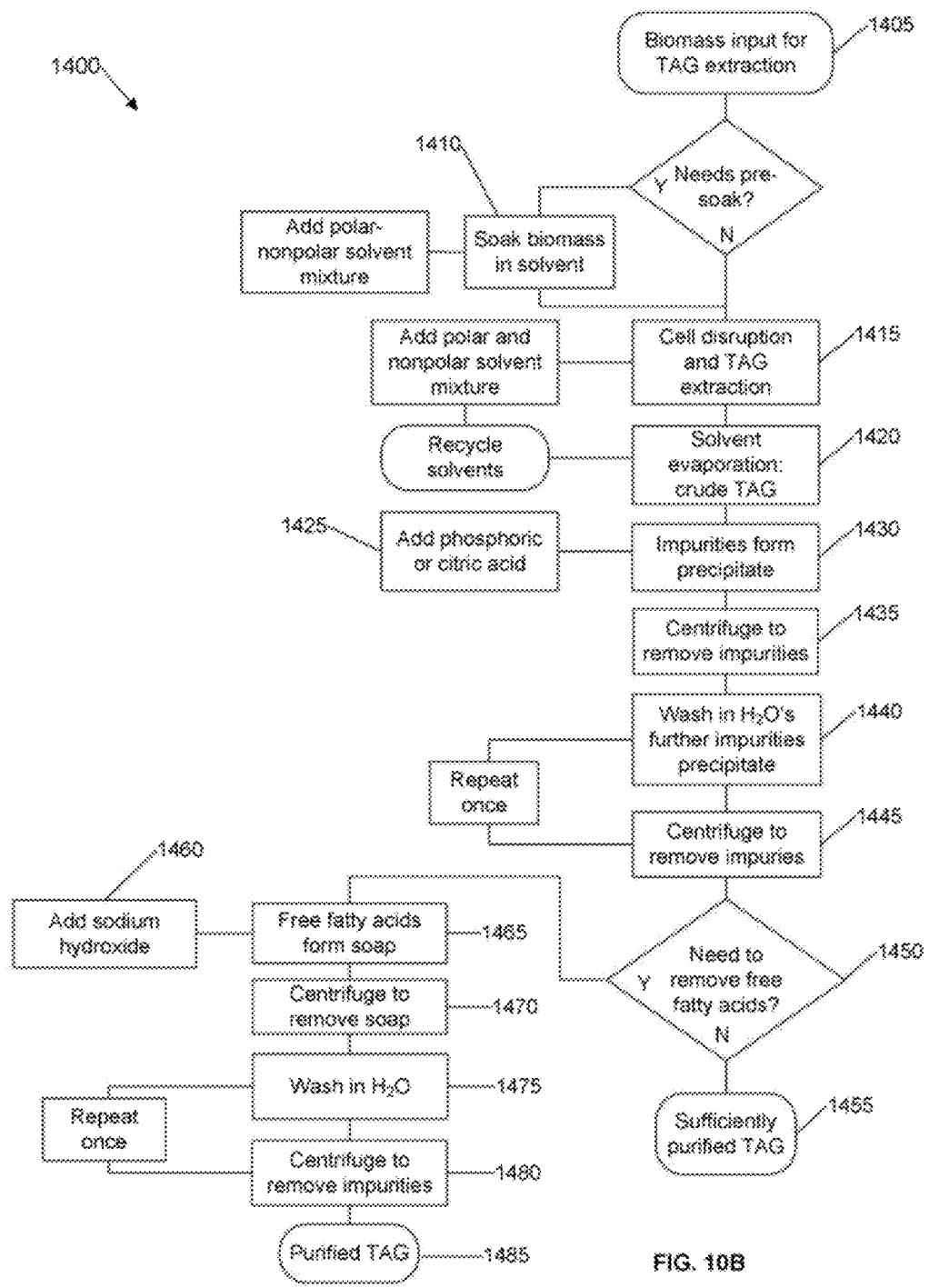
FIG. 10B is a flow chart of a TAG extraction and purification process according to another embodiment of the invention.

Referring now to FIG. 10B, a method of producing TAG, in accordance with another embodiment, is shown. With the appropriate choice of microbe and culture nutrients, the crude TAG produced by the extraction process (using, for example, the ethanol-hexane solvent mixture) includes approximately 10% phospholipids, approximately 5% free fatty acids, and the remainder mostly TAG, with some mono-acyl-glycerides and di-acyl-glycerides. Purification of the crude TAG removes phospholipids and free fatty acids, to the extent specified by downstream processes that upgrade TAG into fuel.

Similar to the method shown in FIG. 10A, TAG extraction and purification process 1400 includes: starting with wet biomass in step 1405, optionally drying the biomass (not shown), optionally pre-soaking the dry biomass in a mixture of nonpolar and polar organic solvents in step 1410, disrupting the cell structures and extracting the TAG in step 1415 (e.g., via a Soxhlet-like process using a mixture of alcoholic and non-polar organic solvents), evaporating the solvent mixture from the collected liquid to produce crude TAG in step 1420.

Crude TAG is combined with a chosen acid in step 1425. Typically, phosphoric acid of 85% concentration is used (a concentration that is conveniently available from suppliers), and this material is added in a volume ratio of approximately 1:100, acid to crude TAG. The ratio may vary by a factor of five in either direction. A citric acid solution of approximately 10% can be used as an alternative to phosphoric acid. The phospholipids and acid form a salt that separates from the TAG in step 1430. After mixing the acid and crude TAG, the material is centrifuged in step 1435 to enable removal of the bulk of the phospholipid salts.

Centrifugation is followed by a wash of the TAG with pure water in step 1440, further separating impurities that are removed by another centrifugation. This water wash and centrifugation step may be repeated, if needed, as shown in step 1445.

The TAG at this point (step 1450) is believed to contain up to approximately 5% or more free fatty acids. Some downstream processes can make use of these acids and convert them to fuel, while others cannot. If the downstream process can use the free fatty acids, then the TAG is deemed sufficiently purified and is delivered for conversion to fuel in step 1455. If not, the following additional purification steps are performed.

A titration is performed on an aliquot of the TAG to quantify its free fatty acid concentration in step 1465. Using a procedure well known in the art, the appropriate amount of sodium hydroxide is calculated, and that amount is added to the TAG in step 1460. The sodium hydroxide combines with the free fatty acids, yielding soap (the process is called saponification) in step 1465. The soap is removed via a centrifugation step, as shown in step 1470.

Centrifugation is followed by a wash of the TAG with pure water in step 1475, further separating impurities that are removed by another centrifugation in step 1480. This water wash and centrifugation step may be repeated, if needed. The end result of this process is purified TAG delivered for downstream conversion to fuel (shown in step 1485).

Figure 11:
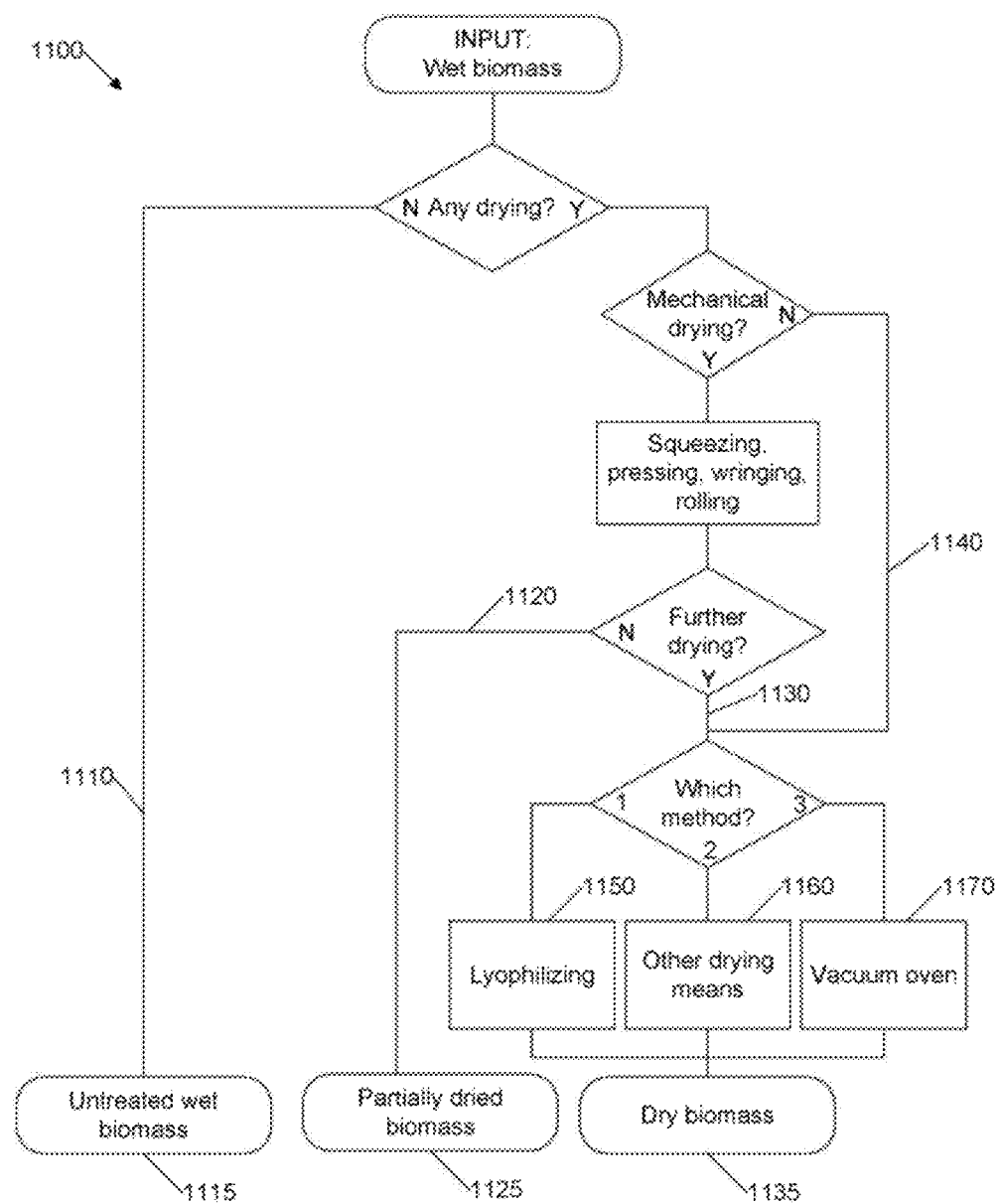
FIG. 11 is a flow chart of a biomass drying process according to an embodiment of the invention.

Referring now to FIG. 11, a biomass drying process 1100 is shown. Drying process 1100 includes optional paths for no drying 1110 (resulting in untreated wet biomass 1115), for mechanical removal of gross water only 1120 (resulting in partially dried biomass 1125), for mechanical water removal followed by more thorough drying 1130 (resulting in dry biomass 1135), and for thorough drying not preceded by mechanical water removal 1140 (resulting in dry biomass 1135). Three means for thorough drying are shown: lyophilizing 1150, using a vacuum oven 1170, and other drying means 1160 (e.g., drying apparatus shown in FIGS. 7 and 8).

In some embodiments, maintaining the purity of the solvent, as is done by the evaporation-recondensation cycle in the Soxhlet apparatus, is not, in fact, necessary to obtain efficient extraction of the lipids. As is easily appreciated, in the Soxhlet, the biomass remains stationary inside a confining filter (thimble), and the solvent acts by diffusive processes within the biomass. In such a diffusion-dominated extraction, it is important to keep the chemical kinetics favorable to continued dissolution of the lipids in the solvent. If the solvent were allowed to accumulate dissolved lipids, the chemical kinetics of dissolution would become less favorable due to partition coefficients of the lipids in the solvents, leading to limited efficiency of lipid extraction.

In an alternative embodiment, the biomass is not confined to be stationary inside a filter (e.g., such as in the Soxhlet apparatus), but is freely suspended, as a slurry, in the solvent. An agitator such as, for example, a rotary stirring mechanism moves the biomass in a solvent bath. In some embodiments, the solvent is heated to a temperature range typically between about 50 and 100° C., or in general from about half the boiling point of the solvent mixture up to just below the boiling point of the solvent mixture.

Physical agitation ensures that the solvent reaches all portions of the biomass. Generally, agitation makes the chemical kinetics of dissolution more favorable, so that extraction effectiveness may be achieved that is equivalent to the Soxhlet process. In effect, physical agitation replaces the evaporation-condensation cycle; in both cases, the solvent is heated to increase the kinetics of the dissolution reaction. While not wishing to be bound by any particular theory, it is believed that by avoiding the two phase transition cycle required in the Soxhlet process, the heating-physical agitation method saves a very significant amount of energy and cost. For example, evaporation and condensation is needed only at the final separation stage, and then only needs to be performed once instead of many times over. While not wishing to be bound by any particular theory, it is also believed that the physical apparatus required for this physical agitation-based process is much less expensive than that required for the Soxhlet process, thus saving a significant amount of capital expenditure.

Following the dissolution process, the lipid-laden solvent is separated from the biomass via physical filtration. An evaporation stage evaporates the solvent; thus, the solvent is recaptured in its pure state to process the next batch of biomass and leaves the crude lipid extract to be processed further.

In some embodiments, the cellular debris 988 is sent to a gasifier and consumed to produce on-site electricity and/or process heat. The cellular debris 988 may also be used as part of the carbon and non-carbon nutrients in the metabolization stage 530 of FIG. 5. Alternatively, the cellular debris 988 may be collected, processed and sold as other products, such as livestock feed.

As is easily appreciated, TAG produced in accordance with embodiments of the present invention may be used as a liquid fuel suitable for transportation uses. In some embodiments, the fuel product includes saturated non-aromatic hydrocarbon molecules (e.g., alkanes and branched alkanes) with molecular weights in a predetermined range (e.g., as required by vehicle engines).

Table 1 shows exemplary TAG produced by *P. menonorum*.

TABLE 1

Fatty acid profile of the TAG produced by P. menonorum

| Fatty Acid Common Name | Carbon Chain Length | Number of Double Bonds | Abundance (wt %) |
|---|---|---|---|
| Myristic Acid | 14 | 0 | 0.31 |
| Pentadecylic Acid | 15 | 0 | 0.21 |
| Palmitic acid | 16 | 0 | 20.89 |
| Margaric Acid | 17 | 0 | 0.21 |
| Stearic Acid | 18 | 0 | 7.07 |
| Oleic Acid | 18 | 1 | 20.52 |
| Linoleic acid | 18 | 2 | 45.31 |
| Linolenic Acid | 18 | 3 | 3.50 |
| Arachic Acid | 20 | 0 | 0.27 |
| Behenic Acid | 22 | 0 | 0.59 |
| Lignoceric Acid | 24 | 0 | 1.12 |

As shown in Table 1, the main components of this particular TAG product include linoleic acid, oleic acid, stearic acid and palmitic acid. The carbon chain length distribution in Table 1 indicates that any liquid transportation fuel can be refined from the product, with reasonable efficiency.

As is easily appreciated, the product composition may be adjusted, by varying process conditions, to partially offset feedstock variations and to meet application specifications. Depending on product specifications, in some embodiments, the liquid fuel product may contain a proportion of saturated aromatic carbon compounds. For example, jet fuel specifications call for aromatic components comprising between 8% and 25%, by weight, of the total fuel composition.

Filtration/Extraction Apparatus

In accordance with the above, in certain embodiments described herein, the filtration/drying chamber, cell disruption apparatus and TAG extraction apparatus described hereinabove comprise a cellulose degrading fungus. In a preferred embodiment, the fungus comprises a cellulose degrading fungus of the genus *Penicillium*. For example, the filtration/drying apparatus may be a vessel as shown in FIGS. 7A, 7B and 8. However, it will be readily appreciated that any suitable filtration/drying system suitable for the extraction of moisture from a wet mass of a cellulose degrading fungus can be used.

Similarly, the cell disruption and TAG extraction apparatus may be an apparatus as described hereinabove and in the process diagramed in FIG. 10. However, it will be readily appreciated that any suitable cell disruption system or TAG extraction suitable for the disruption of a cellulose degrading fungus or the extraction of TAG from a cellulose degrading fungus can be used.

As used herein, the terms "filtration apparatus", "drying chamber", "filter", "drying vessel", "drying apparatus" and the like refer to an apparatus or chamber in which a mycelial mat of a cellulose degrading fungus such as a fungus of the genus *Penicillium* can be dispersed on a filtration surface such as a filter, screen, sheet and the like. A filtration apparatus, such as any of those described herein and in the Figures, are useful for the extraction of moisture from a mass of cellulose degrading fungi such as the fungus described herein as *Penicillium menonorum*. For example, in a filtration apparatus, any one of a number of variables such as temperature, airflow, and the like may be monitored and/or controlled to achieve a desired level of extraction of moisture. In a preferred embodiment, the mycelial mat is dried until it reaches a constant weight. In other embodiments, the mycelial mat can comprises less than 50% moisture, less than 45% moisture, less than 40% moisture, less than 35% moisture, less than 30% moisture, less than 25% moisture, less than 20% moisture, less than 15% moisture, less than 10% moisture, less than 5% moisture, less than 4% moisture, less than 3% moisture, less than 2% moisture and less than 1% moisture. It will be readily appreciated that any suitable drying apparatus, including a screen or sheet, can be utilized.

As used herein, the term "cell disruption apparatus" and the like refers to an apparatus in which the cellular structure of a cellulose degrading fungus such as a fungus of the genus *Penicillium* can be disrupted to result in the liberation of cellular components such as TAG. A suitable apparatus may utilize methods including one or more of mechanical, thermal, or chemical methods. For example, mechanical disruption methods may include one or more of ultrasonic, cutting, pressing, rolling or abrading means. Thermal methods may use heated air or microwave energy, or for example, cryogenic means such as freezing in liquid nitrogen, among other means. Chemical means use one of several chemical agents, including but not limited to hexane and methanol, chloroform, chloroform and methanol, or methylene chloride. Accordingly, a cell disruption apparatus, such as any of those described herein and in the Figures, is useful for the liberation of TAG from a mass of cellulose degrading fungi such as the fungus described herein as *Penicillium menonorum*.

As used herein, the terms "extraction apparatus", "TAG extraction apparatus" and the like refer to an apparatus in which the lipids, including TAG, from a cellulose degrading fungus, such as a fungus of the genus *Penicillium*, can go into solution. A suitable apparatus may utilize the solvents and conditions described hereinabove. However, it will be appreciated that any apparatus used to solubilize liberated TAG is useful as a TAG extraction apparatus. Accordingly, a TAG extraction apparatus, such as any of those described hereinabove, is useful for the extraction of TAG from a mass of cellulose degrading fungi such as the fungus described herein as *Penicillium menonorum*.

Accordingly, one embodiment described herein is a filtration apparatus comprising a filter housing having a filtration surface disposed therein, and a mycelial mat of a cellulose degrading fungus of the genus *Penicillium* dispersed on the filtration surface. In a preferred embodiment, the filtration apparatus comprises *Penicillium menonorum*. Preferably, the filtration apparatus comprises a fungus of the genus *Penicillium*, the species being the same as NRRL deposit Accession No: 50410. In some aspects, the mycelial mat comprises a moisture content of less than about 85% w/w. In other aspects, the mycelial mat comprises a moisture content of less than about 50% w/w. In other aspects, the mycelial mat comprises a moisture content of less than about 25% w/w. In still other aspects, the mycelial mat comprises a moisture content of less than about 15% w/w. In yet other aspects, the mycelial mat comprises a moisture content of less than about 5% w/w.

Another embodiment described herein includes an extraction apparatus comprising a vessel comprising a solvent and a fungus, wherein the solvent is in contact with the fungus. In a preferred embodiment, the extraction apparatus comprises hyphal filaments of a cellulose degrading fungus of the genus *Penicillium* dispersed in an aprotic solvent. Typical solvents can include a polar organic solvent (such as methanol, ethanol, isopropanol, or the like) and a non-polar organic solvent (such as hexane, chloroform, methylene chloride, or the like). It will be appreciated that any suitable solvent or mixture of solvents that allows for extraction of TAG from disrupted hyphal filaments and other cells of the fungus can be used. In a preferred embodiment, the extraction apparatus comprises *Penicillium menonorum*. Preferably, the apparatus comprises a fungus of the genus *Penicillium*, the species being the same as NRRL deposit Accession No: 50410.

Another embodiment presented herein is an extraction apparatus comprising a vessel comprising a solvent and a fungus, wherein the solvent is in contact with the fungus. In a preferred embodiment, the extraction apparatus comprises hyphal filaments of a cellulose degrading fungus of the genus *Penicillium* dispersed in a solvent comprising less than 80% water. In some embodiments, the solvent comprises at least one aliphatic solvent. In some embodiments, the solvent comprises at least one polar solvent. In certain embodiments, the polar solvent is aprotic. In some embodiments, the solvent comprises a non-polar organic solvent (such as hexane, chloroform, methylene chloride, or the like) and a polar organic solvent (such as methanol, ethanol, isopropanol, or the like). In one preferred embodiment, the solvent comprises hexane and ethanol. In a preferred embodiment, the alcohol-based solvent is at a concentration of about 0%, 1%, 2%, 3%, 4%, 5%, 6,%, 7%, 8%, 9%, 10%, 15%, 20%, 25% or about 30%, by volume. In a preferred embodiment, the ethanol is at a concentration of about 10-20%. In a more preferred embodiment, the ethanol is at a concentration of about 10%. In another embodiment, the solvent comprises a mixture of methanol and chloroform. In a preferred embodiment, the apparatus comprises *Penicillium menonorum*. Preferably, the apparatus comprises a fungus of the genus *Penicillium*, the species being the same as NRRL deposit Accession No: 50410.

In a preferred embodiment, the fungus in the filtration apparatus or extraction apparatus described above can have a 5.8S ribosomal RNA gene sequence with sequence identity with the nucleic acid of SEQ ID NO: 1. In a preferred embodiment, the fungus can have an ITS1 sequence having sequence identity with the nucleic acid of SEQ ID NO: 2. In a preferred embodiment, the fungus can have an ITS2 sequence having sequence identity with the nucleic acid of SEQ ID NO: 3. In a preferred embodiment, the fungus can have a 28S rRNA gene sequence having sequence identity with the nucleic acid of SEQ ID NO: 4. More preferably, the sequence identity with SEQ ID NOs: 1, 2, 3 and/or 4 is at least 10%, 20%, 30%, 40%, 50%, 60%, 70%, 80%, 85%, 86%, 87%, 88%, 89%, 90%, 91%, 92%, 93%, 94%, 95%, 96%, 97%, 98% or at least 99% nucleotide sequence identity with the nucleic acid of SEQ ID NO: 1, 2, 3 and/or 4.

Extracting Aromatic Compounds

As stated above, extracting product from a digester is different, depending on whether the product is TAG from cellulose breakdown or aromatic hydrocarbons from lignin breakdown. The digester that receives the solid, lignin-rich portion of pretreated feedstock includes water, nutrients and an appropriate inoculum added to break the lignin down into a variety of aromatic compounds. At the end of the fermentation or digestion cycle, the solid mass is a combination of microbes and undigested solid feedstock, which can sometimes be waste.

The aromatic compounds are included as part of the liquid and gas phase of the digester output (rather than being stored intracellularly as in TAG production). This is because the microbes break lignin down not primarily to digest it for nutrient value, but to gain access to proteins inside the lignin structures. Thus, the microbes do not absorb and metabolize the lignin breakdown products.

In some embodiments, the solid portion of the digester contents can sometimes be waste that can be disposed of or gasified to produce electricity and process heat. Standard chemical separation and purification processes may be implemented to capture the aromatics from the liquid and gas-phase outputs of the fermentation.

After extraction of the aromatic compounds, the aromatics may then be fractionated by molecular weight. The fractionated aromatics may then be blended with alkanes to form constituents of gasoline, diesel or jet fuel. Such blending process is known to those skilled in the art.

Figure 12:
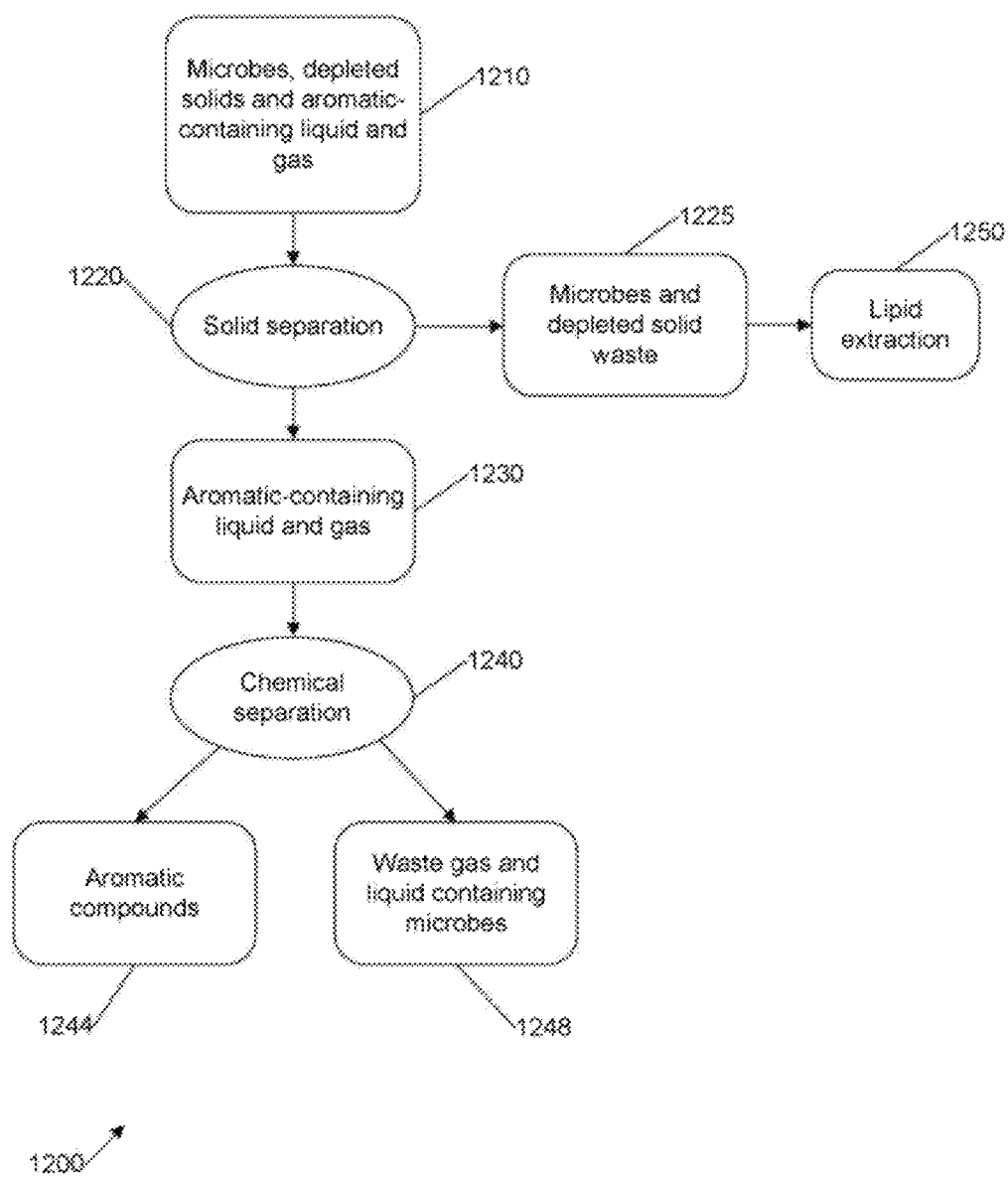
FIG. 12 is a flow chart of a separation process according to an embodiment of the invention.

Referring now to FIG. 12, a flow chart of a separation process 1200 in accordance with an embodiment of the invention is shown. The separation process 1200 includes a receiving stage 1210 for receiving the mixture 640 containing depleted solids, microbes, and gas and liquid containing the desired aromatic compounds yielded by the metabolization step 630 of FIG. 6.

The separation process 1200 subjects the mixture 640 to a mechanical solids separation step 1220. This separation step 1220 uses one or more of standard mechanical means such as screening, sieving, centrifugation or filtration to achieve the separation. The separated depleted solids and microbes 1225 can be sent to a gasifier and consumed to produce on-site electricity and/or process heat. Alternatively, the depleted solids may be collected, processed and sold as other products, such as livestock feed. In yet another embodiment, the separated depleted solids and microbes 1225 may be further processed, such as via lipid extraction 1250.

The separation step 1220 also outputs liquid and gas 1230 containing the target aromatic compounds. A chemical separation step 1240, using standard chemical processes known in the art, separates aromatic compounds from the others and fractionates them by molecular weight, yielding the aromatic compounds of interest 1244. The byproduct of this chemical separation step 1240 is the waste gas and liquid 1248, which may contain microbial cell bodies. In some embodiments, this waste liquid 1248 is recycled to form part of the input water mixture 134 of the feedstock pretreatment stage 130 of FIG. 1.

The production of TAG and aromatic compounds may be associated with or implemented by a cellulose processing plant and/or a bio-refinery producing transportation fuel. The association may be integral, parallel, or separate.

In some embodiments, a cellulose processing plant receives agricultural waste (or other cellulosic material including animal manure), converts it into TAGs by microbial action, and then extracts intermediates from TAGs that may be converted to fuel. In contrast, a bio-refinery typically receives TAG and aromatic compounds, processes them and blends them into transportation fuels.

In one embodiment, the production of TAG and aromatic compounds is implemented by a cellulose processing plant in parallel with a bio-refinery. In such an embodiment, glycerol produced by the bio-refinery is used to generate further lipids, and then either convert the lipids into fuel or pass the lipids to the bio-refinery plant which converts the lipids to fuel.

In another embodiment, the production of TAG and aromatic compounds is implemented by a cellulose processing plant integrated with a bio-refinery. In such an embodiment, the cellulose processing system is utilized to produce glycerol. For example, the same vessel may contain both the cellulose digestion mixture and the glycerol consumption mixture intermingled. The microbes for cellulose digestion and glycerol consumption may be intermingled if they are compatible. It will be appreciated that the same microbe may perform both cellulose digestion and glycerol consumption simultaneously. Similarly, a single combined lipid product may be recovered from both processes.

In another embodiment, the production of TAG and aromatic compounds is implemented by a cellulose processing plant separate from a bio-refinery. In such an embodiment, the glycerol processing is separate from the cellulose processing. In one example, the glycerol feed may be reduced all the way to the fuel product. Alternatively, the glycerol feed may provide lipids as an intermediate product, with fuel production being completed at the separate bio-refinery or chemical refinery. In some embodiments, alkanes are extracted from TAGs and recycled in the glycerol processor to generate further fuel. This process may be repeated in cyclical fashion until the feed material is exhausted.

From the above description, a method in accordance with embodiments of the present invention, include a series of steps. These steps include one or more of the following:

(1) Receiving and pretreating cellulosic feedstock;
(2) Optionally, adding glycerol obtained as a co-product of TAG transesterification;
(3) Separating the pretreated feedstock into liquid and solid phases;
(4) Inoculating the liquid phase with microbes that are capable of converting the carbon into lipids, then allowing the microbes to do so;
(5) Harvesting the resulting microbial biomass from the liquid;
(6) Extracting the lipids for subsequent conversion into fuels.
(7) Mixing the solid-phase pretreated feedstock with water and nutrients, then inoculating it with microbes capable of attacking the lignin and converting it into aromatic compounds;
(8) Separating the resulting aromatics from the liquid and gas phases of the digester output;
(9) Recycling the remaining solid-phase matter as a co-product or as feed for gasification and conversion to heat and electricity or as added carbon feedstock for subsequent microbial processing;
(10) Recycling the liquid-phase matter as broth for the next batch of feedstock and fermentation.

Additionally, in some embodiments, the pretreatment process 100, as shown in FIG. 1, leaves considerable cellulose and hemicellulose in the solid phase or portion 148. In such embodiments, the solid-phase feedstock 148 is inoculated with a consortium of microbes that includes species to digest the cellulose and hemicellulose and produce intracellular TAG as well as species to break down the lignin and secrete aromatic molecules in step 620. Following the metabolization step 630, the aromatic compound separation 1220 proceeds as indicated in FIG. 12, but the solid phase extract 1225 is no longer mere waste or recycling material, but is subjected to the TAG extraction process 980 of FIG. 9.

In some embodiments, the liquid-solid separation step 140 at the end of the feedstock pretreatment process 100 of FIG. 1 is absent. In such embodiments, the unseparated feedstock is inoculated with a consortium of microbes capable of digesting both liquid and solid phases, the aromatic compounds are separated as shown in FIG. 12, and the TAG is extracted as shown in FIG. 9.

Figure 13:
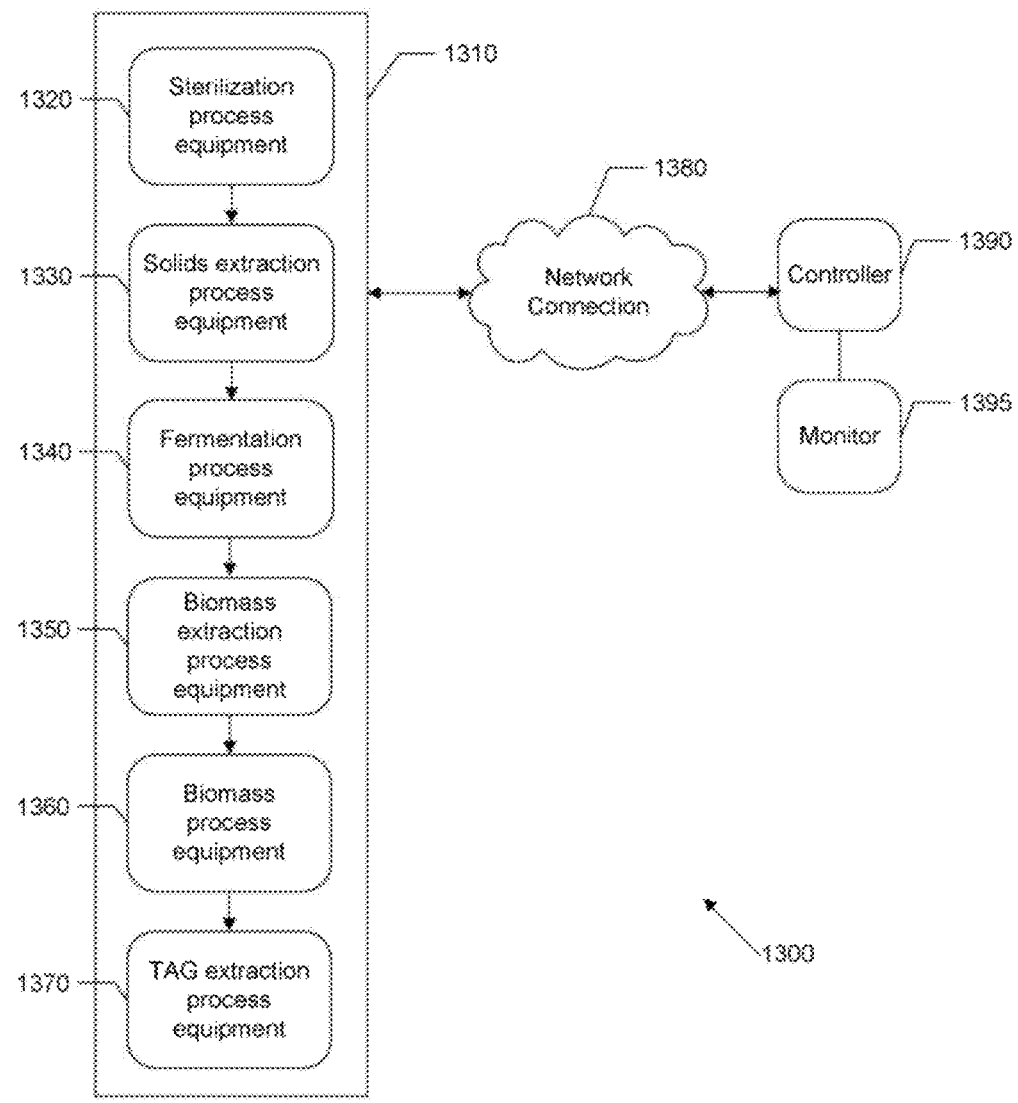
FIG. 13 is a block diagram of process equipment used in accordance with FIGS. 1-12.

Turning now to FIG. 13, a system 1300 for producing TAG in accordance with an embodiment is shown. System 1300 includes a processing plant or facility 1310 in communication with a controller 1390. In one embodiment, processing plant 1310 communicates with controller 1390 via a network connection 1380. Network connection 1380 may be wireless or hard-wired. Network connection 1380 may also include the use of a web browser or other internet connectivity to allow observation and control from a remote location.

In some embodiments, controller 1390 provides operating instructions for processing plant 1310's operating conditions. Controller 1390 may receive information from processing plant 1310 and utilize the information as feedback to adjust operating instructions to processing plant 1310. Parameters that can be actively controlled in this way include, among others, temperature, pH, dissolved oxygen, and the controlled continuous feed or carbon and/or carbon nutrients.

In one embodiment, the operating conditions may be presented on a monitor or display 1395 and a user may interact with the operating conditions via a user interface. The monitor 1395 may be in the form of a cathode ray tube, a flat panel screen or any other display module. The user interface may include a keyboard, mouse, joystick, write pen or other device such as a microphone, video camera or other user input device.

Processing facility 1310 includes sterilization process equipment or sterilizer 1320, solids extraction process equipment or solids extractor 1330, bioreactor 1340 (e.g., fermentation process equipment or fermentor), microbial biomass extraction process equipment or microbial biomass extractor 1350, cell disruption process equipment or cell disruptor 1360 and TAG extraction and purification process equipment or TAG extractor 1370. In one embodiment, cell disrupter 1360 is microbial biomass process equipment. In some embodiments, controller 1390 is in communication with fermentor 1340 and provides/controls the operating conditions of fermentor 1340.

Sterilization process equipment 1320 and solids extraction process equipment 1330 together perform the cellulosic feedstock pretreatment process 100 of FIG. 1. Fermentation process equipment 1340 performs the inoculation and fermentation process 500 of FIG. 5. Microbial biomass extraction process equipment 1350, cell disruption process equipment 1360 and TAG extraction process equipment 1370 together perform the microbial biomass collection process 900 of FIG. 9.

Those of skill will appreciate that the various illustrative logical blocks, modules, and algorithm steps described in connection with the embodiments disclosed herein can often be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the design constraints imposed on the overall system. Skilled persons can implement the described functionality in varying ways for each particular application, but such implementation decisions should not be interpreted as causing a departure from the scope of the invention. In addition, the grouping of functions within a module, block or step is for ease of description. Specific functions or steps can be moved from one module or block without departing from the invention.

The various illustrative logical blocks and modules described in connection with the embodiments disclosed herein can be implemented or performed with a general purpose processor, a digital signal processor (DSP), application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any processor, controller, microcontroller, or state machine. A processor can also be implemented as a combination of computing devices, for example, a combination of a DSP and a microprocessor, a plurality of microprocessors, one or more microprocessors in conjunction with a DSP core, or any other such configuration.

The steps of a method or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of storage medium. An exemplary storage medium can be coupled to the processor such that the processor can read information from, and write information to, the storage medium. In the alternative, the storage medium can be integral to the processor. The processor and the storage medium can reside in an ASIC.

Facilities and Processes for Producing Biofuels and Co-Products

As described hereinabove, the cellulose degrading fungus of the genus *Penicillium* can be grown in a bioprocess reactor under conditions that permit the fungus to produce biofuel and one or more economically valuable co-products. Some economically valuable products and co-products include, for example, lipids, aromatic compounds and other breakdown products, conditioned medium, residual solids derived from digested feedstock, metabolites, phospholipids, and spent fungal cells. Each of these co-products is discussed briefly below.

The main product of this process is lipids sequestered inside the fungal cells and extracted via the processes described hereinabove. The lipids are primarily tri-acyl-glycerides (TAG), and their fatty acid components have a carbon chain length distribution well suited to subsequent processing into fuel (whether biodiesel as fatty acid methyl esters or petroleum replacement fuels as hydrocarbons). The TAG forms anywhere from 5% to more than 35-40% of the total dry weight of the fungal cells.

The liquid culture medium contains metabolites produced by the fungus during its life cycle. These metabolites may include co-products which are useful as pharmacologically active compounds such as antibiotics, antifungals, anti-cancer agents, anti-atherosclerotic agents, and the like.

Phospholipids are often present in the TAG extract. As extracted from the cells, phospholipids are present as anywhere from ~1% to ~30% of the crude extract. These are typically separated from the actual TAG in a subsequent purification process; when the phospholipids themselves are purified, they form lecithin, a co-product.

The spent fungal cells, after the TAG has been extracted, contain proteins that can form a co-product: a nutrient for land and aquatic species raised as food for humans, and/or as pets. The material can also find use as a human foodstuff or ingredient thereof.

Accordingly, facilities made up of a plurality of bioprocess reactors are useful as a means to increase production of the biofuels and other co-products. As such, described herein is a bioprocessing facility for producing co-products, the facility comprising a plurality of bioprocess reactors. The plurality of bioprocess reactors can vary in size and capacity in order to allow scale-up of a culture, for example. The bioprocess reactors as described hereinabove can comprise a cellulose degrading fungus of the genus *Penicillium* growing in a liquid medium, the liquid medium comprising a carbon source and a nitrogen source, wherein the ratio of carbon to nitrogen in the medium ranges from about 1:1 to about 1000:1. In typical embodiments, the fungus comprises *Penicillium menonorum*. In preferred embodiments, the fungus comprises a species being the same as NRRL deposit Accession No: 50410.

In accordance with the above, also described herein is a process for manufacturing a plurality of co-products, the process comprising: a) inoculating a bioprocess reactor with an inoculum of a cellulose degrading fungus of the genus *Penicillium*; b) allowing a sufficient time for production of TAG by said fungus, wherein said TAG comprises at least 5% of the dry weight of the fungus; c) harvesting said fungus; d) extracting lipids from said fungus, thereby producing a lipid co-product. The process can further comprise e) drying said fungus, thereby producing a feed co-product. In some aspects, the TAG comprises at least 35% of the dry weight of the fungus. In other aspects, the lipid co-product comprises a TAG co-product and a phospholipid co-product. In still other aspects, the phospholipid co-product comprises lecithin. In yet other aspects, the feed co-product is suitable for animal and/or human consumption. In typical embodiments, the fungus comprises *Penicillium menonorum*. In preferred embodiments, the fungus comprises a species being the same as NRRL deposit Accession No: 50410.

In some embodiments, one or more co-products are harvested from the reaction vessel to separate the one or more co-products from the other remaining components. Co-products which can be harvested include, for example, lipids, aromatic compounds and other breakdown products, conditioned medium, residual solids derived from digested feedstock, metabolites, phospholipids, and fungal biomass. The one or more co-products can be harvested separately, or they can be harvested together. The one or more co-products can be harvested simultaneously, in sequence, or separately. After harvesting a component or co-product, the one or more co-products may need to be further extracted, as described elsewhere herein.

In some embodiments, the bioprocess reactor comprises a carbon source selected from the group consisting of: a solid feedstock, a lysate in a liquid, a gaseous vapor, and a combination thereof. Thus, for example, in embodiments where lignin is present in solid feedstock, aromatic compounds can be harvested from the reaction medium. In certain embodiments, the aromatic compounds are further extracted from the medium.

Furthermore, also described herein is a facility comprising: a vessel for holding liquid medium conditioned by a cellulose degrading fungus of the genus *Penicillium*; an extraction apparatus comprising an extract of lipids derived from said fungus; and a drying apparatus comprising dried fungus. It will be appreciated that some metabolites produced by the cellulose degrading fungus are secreted by the organism into the liquid medium. As such, the vessel can contain one or more metabolites that are useful as co-products. The extraction apparatus can comprise extraction solvent that contains lipids extracted from the cellulose degrading fungus. Typically, the extract comprises TAG. Additionally, the extract of lipids can comprise phospholipids, such as, for example, phosphatidylcholine, phosphatidylethanolamine, and phosphatidylinositol and the like. When such phospholipids themselves are purified, they can form lecithin. The drying apparatus can comprise dried biomass, comprising spent fungal cells after the TAG has been extracted. The dried biomass typically contains proteins, carbohydrates, and fiber that are suitable for animal and/or human consumption. In typical embodiments, the fungus comprises *Penicillium menonorum*. In preferred embodiments, the fungus comprises a species being the same as NRRL deposit Accession No: 50410.

Improved Animal Feeds

Presented herein is the discovery that feed formulations incorporating fungal biomass have superior qualities and that animals fed using such formulations may have increased survival compared to existing feeds. Also presented herein is the discovery that feed formulations incorporating fungal biomass have at least equivalent if not superior qualities to standard feed formulations that do not incorporate fungal biomass and that animals fed using such formulations have at least equivalent if not increased survival compared to existing feeds. Also disclosed herein is a new animal meal formulation that also provides a market for whey, which had been a waste product from a different industry: cheese manufacture.

Another aspect of this disclosure is the admixture of the microbial biomass, following extraction of the lipids comprising fuel precursors, with whey. Whey liquids are a waste product resulting from the manufacture of cheese. The volume of this waste product is significant, as it constitutes approximately 85-90% of the milk volume, and retains 55% of milk nutrients. Among the most abundant of these nutrients are lactose (3.8-5.0% w/v), soluble proteins (0.6-0.8% w/v), lipids, and mineral salts. The waste must be processed in sewage treatment plants, and many jurisdictions impose significant costs on the cheese producers in order to process the material. Accordingly, whey disposal represents a major expense in cheese production. The composition of whey varies from process to process, but represents approximately 3.8-5% w/w of lactose or lactate, and 0.4-0.8% w/w of proteins. By combining the whey with the dried microbial animal meal, a new product is formed with beneficial nutritive properties. This renders the whey, heretofore a waste creating disposal expense, into a co-product representing a source of revenue to the cheese producer.

Contemplated herein are compositions that include one or more specific genera and species of microbes that not only convert a wide range of cellulosic feedstocks into lipids effectively, but also yield desirable co-products. An example of the latter includes the spent microbial biomass after the lipids have been extracted, which can be sold as protein meal to feed livestock in agriculture, aquaculture or pets. The protein meal may also find use as a source of human nutrition. Primary or secondary metabolites produced and/or secreted by the one or more microbes provide another class of co-products. In some embodiments, the metabolites may be primary metabolites.

As described hereinabove, the cellulose degrading fungus of the genus *Penicillium* can be grown in a bioprocess reactor under conditions that permit the fungus to produce biofuel and one or more economically valuable co-products. Some economically valuable products and co-products include, for example, lipids, metabolites, phospholipids, and spent fungal cells. The discussion below focuses on the last-named co-product.

The spent fungal cells, after the TAG has been extracted, contain proteins that can form a co-product: a nutrient for land and aquatic species of animals raised as food for humans, and/or as pets. The material can also find use as a human foodstuff or ingredient thereof.

Accordingly, facilities made up of a plurality of bioprocess reactors are useful as a means to increase production of the biofuels and other co-products. As such, described herein is a bioprocessing facility for producing co-products, the facility comprising a plurality of bioprocess reactors. The plurality of bioprocess reactors can vary in size and capacity in order to allow scale-up of a culture, for example. The bioprocess reactors as described hereinabove can comprise a cellulose degrading fungus of the genus *Penicillium* growing in a liquid medium, the liquid medium comprising a carbon source and a nitrogen source, wherein the ratio of carbon to nitrogen in the medium ranges from about 1:1 to about 1000:1. In typical embodiments, the fungus comprises *Penicillium menonorum*. In preferred embodiments, the fungus comprises a species being the same as NRRL deposit Accession No: 50410.

Animal Feed Compositions

Provided herein are animal feed compositions comprising a fungal biomass derived from a cellulose degrading fungus of the genus *Penicillium*. The animal feed compositions provided herein can comprise the fungal biomass in an amount ranging from about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95% to about 100% by weight. In some embodiments, the animal feed can comprise the biomass in an amount ranging from 5% to 10% by weight. In typical embodiments, the fungus comprises *Penicillium menonorum*, and related strains as described hereinabove and in the incorporated materials of Application No. 61/372,828, filed Aug. 11, 2010, entitled, "Bioreactors Comprising Fungal Strains." In preferred embodiments, the fungus comprises a species being the same as NRRL deposit Accession No: 50410.

In certain embodiments provided herein, the animal feed has been substantially depleted of a lipid product. As used herein, the term "substantially depleted" refers to a significant depletion of the lipid product from the fungal biomass. In certain embodiments, substantial depletion refers to depletion of more than 20%, 30%, 40%, 50%, 60%, 70%, 75%, 80%, 85%, 90%, 95% or more than 99% of the lipid product. The lipid product can be, for example TAG. In some embodiments, the lipid product can comprise TAG and a phospholipid co-product such as lecithin.

As described in Example 6 below, it has been surprisingly discovered that providing an animal feed comprising a fungal biomass derived from a cellulose degrading fungus of the genus *Penicillium* may result in unusual and significant enhanced survival, indicating that such feed formulations can be in many ways superior to existing premium feeds. Accordingly, the animal feed formulations presented herein can be utilized in methodologies for improving the longevity of an animal. In some embodiments, the animal feed provided herein performs at least as well as, or superior to animal feed formulations currently known in the art for the purpose of improving animal growth and survival.

Additionally provided herein is the surprising finding that providing an animal feed comprising a fungal biomass derived from a cellulose degrading fungus of the genus *Penicillium* can result in a significant increase in the resistance of an animal to an infection. Accordingly, methods for enhancing the resistance of an animal to infection are provided. The infection can be, for example, a viral infection, a bacterial, fungal or other microbial infection, or some other parasitic infection. It will be appreciated that in embodiments where the animal feed provided herein enhances the animal's immune system, the method can comprise enhancing the animal's resistance to any infection that is targeted by the animal's immune system. In some embodiments, the animal feed provided herein performs at least as well as, or superior to animal feed formulations currently known in the art for the purpose of improving resistance to infection.

In embodiments provided herein, the animal feed comprising a fungal biomass derived from a cellulose degrading fungus of the genus *Penicillium* is suitable for animal and/or human consumption. In some embodiments, the animal feed is suitable for consumption by a land animal. Land animals are any animals that live predominantly on land and include, for example, cows, chickens, pigs, cats, dogs, humans, rodents, and the like. In some embodiments, the animal feed is suitable for consumption by aquatic animals. Aquatic animals include, for example, fish, shrimp, prawns, aquatic mammals, and the like.

Animal Meal Including Whey

A major waste stream in cheese production is liquid whey. Municipalities operating sewage treatment facilities often charge cheese producers a fixed amount per gallon of whey poured into the sewage stream. Thus, handling waste whey becomes a significant expense in cheese production. The present invention discloses a means to treat the whey such that it can become a revenue source rather than an expense. At the same time, the treatment removes the burden of treating whey in sewage treatment facilities.

Accordingly, presented herein is the discovery that whey can be mixed with fungal cell residual biomass to form a protein meal slurry. This solves several problems. First, it combines the proteins and other nutrients of the fungal biomeal with those of the whey, adding to the nutritional value of the product. Second, it changes the consistency of the dry, granular fungal biomeal into a slurry that can be pumped into tanker trucks for transport, and thence into feeding stations for distribution to farm animals. This, in turn, can reduce the cost of dairy operations: the same tanker trucks that transport milk from the dairy farm to the cheese producer can now, instead of returning empty for the next load of milk, return carrying food for the dairy animals. Example 7, below, lists properties measured for mixtures of whey and fungal-cell biomeal.

In some embodiments, an admixture is provided comprising fungal biomass and whey. In some aspects, the fungal biomass comprises biomass derived from a cellulose degrading fungus of the genus *Penicillium*. In some embodiments, the biomass and the whey form a slurry. In certain aspects, the biomass and whey can be in a dry biomass/whey ratio ranging from about 1:100 to about 100:1 (vol/vol). The ratio of dry biomass/whey can be, for example, about 1:100, 1:90, 1:80, 1:70, 1:60, 1:50, 1:40, 1:30, 1:20, 1:10, 1:5, 1:4, 1:3, 1:2, 1:1, 2:1, 3:1, 4:1, 5:1, 10:1, 20:1, 30:1, 40:1, 50:1, 60:1, 70:1, 80:1, 90:1, or about 100:1. In typical embodiments, the biomass and whey are in a dry biomass/whey ratio ranging from about 1:10 to about 10:1 (vol/vol). Thus, for example, in one embodiment of the invention, 0.17 liters of dry fungal-cell biomeal are mixed with 0.5 liters of whey to produce a slurry capable of being pumped with standard equipment into and out of tanker trucks such as milk tankers. In other embodiments, between 1 liters of fungal-cell biomeal can be combined with between 4 and 5 liters of whey for the same purpose.

In typical embodiments, the fungus comprises *Penicillium menonorum*, and related strains as described hereinabove. In preferred embodiments, the fungus comprises a species being the same as NRRL deposit Accession No: 50410.

In certain embodiments provided herein, the animal feed has been substantially depleted of a lipid product. As used herein, the term "substantially depleted" refers to a significant depletion of the lipid product from the fungal biomass. In certain embodiments, substantial depletion refers to depletion of more than 20%, 30%, 40%, 50%, 60%, 70%, 75%, 80%, 85%, 90%, 95% or more than 99% of the lipid product. The lipid product can be, for example TAG. In some embodiments, the lipid product can comprise TAG and a phospholipid co-product such as lecithin.

Accordingly, also provided herein are a methods of manufacture of an animal feed comprising combining dried fungal biomass with whey, thereby forming an admixture. In one embodiment, the method comprises, prior to combining: extracting a lipid product from fungal biomass; and drying the fungal biomass, thereby producing dried fungal biomass.

Also provided, is a method of feeding an animal comprising providing to the animal an admixture comprising fungal biomass and whey. In some aspects, the method further comprises identifying an animal that would likely benefit from consuming the admixture. For example, identifying an animal that would likely have a superior rate of growth or enhanced immune system function if fed the fungal biomass or admixture described herein as compared to if fed another feed. In some aspects, the fungal biomass comprises biomass derived from a cellulose degrading fungus of the genus *Penicillium*.

In certain aspects, the biomass/whey admixture is suitable for animal and/or human consumption. In embodiments provided herein, the animal feed comprising a fungal biomass derived from a cellulose degrading fungus of the genus *Penicillium* is suitable for animal and/or human consumption. In some embodiments, the animal feed is suitable for consumption by a land animal. Land animals are any animals that live predominantly on land and include, for example, cows, chickens, pigs, cats, dogs, humans, rodents, and the like. In some embodiments, the animal feed is suitable for consumption by aquatic animals. Aquatic animals include, for example, fish, shrimp, prawns, aquatic mammals, and the like.

EXAMPLES

The following examples, including the experiments conducted and results achieved are provided for illustrative purposes only and are not to be construed as limiting upon the teachings herein.

Example 1

Identification and Sequencing

A region of the genome of strain MM-P1 was sequenced to allow comparison to sequences in the National Center for Biotechnology Information (NCBI) nucleotide database. The region included the internal transcribed spacer 1 (ITS1), the 5.8S ribosomal RNA (5.8S rRNA) gene, the internal transcribed spacer 2 (ITS2), and part of the 28S ribosomal RNA (28S rRNA) gene. The identified sequence is set forth in FIG. 14.

A section of this sequence (773 nucleotides) was run through the NCBI Blastn program to identify related sequences in the NCBI nucleotide database. The most similar sequence (98% identical) was that of the same region in *Penicillium pimiteouiense*. Because the MM-P1 sequence was not identical to any other sequence in the database, it was considered to potentially be a new species.

Example 2

Comparison to Related Organisms

The ribosomal sequence of strain MM-P1 was compared to the corresponding ribosomal sequences from other closely related fungi to determine the phylogeny of MM-P1. The nucleotide sequences corresponding to the ITS1, 5.8S rRNA, ITS2, and partial 28S rRNA regions of these species and other *Penicillium* and *Eupenicillium* species were obtained from NCBI. Using the computer software, Geneious (version 5.0), the nucleotide sequences were assembled into a phylogenetic tree. FIG. 15 shows a dendrogram of MM-P1 and its near neighbors, as determined by parsimony analysis. Numbers above the lines indicate bootstrap values for those nodes; only bootstrap values over 70% are shown. The dendrogram set forth in FIG. 15 shows that MM-P1 was closely related to *P. pimiteouiense* and suggested some other close relatives to be used for comparison purposes, including *P. griseolum, P. striatisporum, P. vinaceum, Eupenicillium parvum*, and *E. rubidurum*. The conclusion from these studies is that MM-P1 is most closely related to *E. rubidurum, P. pimiteouiense, P. vinaceum, E. parvum*, and *P. striatisporum*.

Example 3

Relationship of Toxigenic/Pathogenic Penicillium to the Newly-Identified Species An extensive literature search was performed to identify *Penicillium* species and organisms in related genera that are known to produce toxins. Many toxins are known to be produced by more than one species. As for all chemicals, the dose of the toxin will determine how harmful it is to an organism. Therefore, we focused primarily on toxic compounds that are commonly known to cause illness in humans and other animals following consumption of foods contaminated with the toxin-producing organism. Specifically, we looked at patulin, ochratoxins, roquefortines, PR toxin, penitrems, citrinin, penicillic acid, secalonic acid D, and wortmannin. FIG. 16 sets forth a cluster of organisms, some that are most closely related to MM-P1, and others that are more distantly related but still in the same genus. The phylogram was drawn from a maximum parsimony analysis. As seen in FIG. 16, species that produce these toxins are typically phylogenetically related. None of the species most-closely related to MM-P1 are known to produce any of these toxins. Indeed, *P. pimiteouiense* isolated from human kidney cells was specifically found to not produce ochratoxin A (Peterson S W et al. 1999 *Penicillium pimiteouiense*: A New Species Isolated from Polycystic Kidney Cell Cultures. Mycologia 91:269-277, the contents of which are hereby incorporated by reference in their entirety).

Also shown in FIG. 16 are some strains (e.g. *P. decumbens*) that were included to put MM-P1 in its larger context, because they occurred in a previous dendrogram (FIG. 15) with MM-P1; *P. marneffei* is included because it causes infections in immune-compromised humans and *P. camemberti* is included because of its importance in the food industry. In cases where ribosomal RNA gene sequence could not be found (i.e., for *P. confertum, P. palitans*, and *P. nordicum*), a close relative was used to construct the tree; the toxin occurrence indicator dot is not for the stand-in strain, except for the occurrence of ochratoxins and citrinin in *P. verrucosum* (och-ratoxins but not, to our knowledge, citrinin also occur in *P. nordicum*). The phylogenetic tree was created using Geneious (v.5.0) Tree Builder.

Example 4

Growth and Culture of MM-P1

Overview: MM-P1 is grown as a submerged, stirred culture in an aqueous medium. Following growth, the mycelia mass is removed from the culture by filtration and then air dried. When dry, the mycelia are subjected to solvent extraction to remove the majority of the cellular lipids. The remaining components of the mycelia (proteins, carbohydrates, etc.) are then re-dried and available for the use proposed herein.

Details of culture: The substrate for growth of the culture is one or more of the agricultural products in the following exemplary, non-exhaustive list:
  Evaporated cane juice, composed primarily of sucrose but possibly containing dextrose, fructose, cellulosic components of sugar cane, and soil remaining from sugar cane harvest.
  Sorghum grain
  Water-based extract of almond hulls, possibly containing ground almond hulls
  Grape pomace (grape skins, seeds, and stems remaining after juice extraction by the wine and fruit juice industries)
In addition, the following organic and inorganic (mineral) nutrients are added to the culture medium to promote growth:
  Glycerol
  Yeast extract (water-soluble portion of autolyzed cultured yeast) and/or corn steep liquor
  Ammonium phosphate
  Magnesium sulfate
  Calcium chloride
  Ferric citrate
  Potassium sulfate
  Sodium acetate
  Sodium molybdate
  Copper sulfate
  Cobalt nitrate
  Zinc sulfate
  Boric acid
  Manganese chloride
The culture medium is sterilized using a high temperature, high pressure protocol. After the medium has cooled, it is inoculated with MM-P1 and oxygenated. Over the course of the growth of MM-P1 (~6 days), the culture pH is kept at or above pH 5.5 by the addition of potassium hydroxide as needed. At the end of growth, the fungal mycelia and other solids are separated from the culture by filtration and dried. When dry, the lipids are extracted from the mycelia using a hexane/ethanol solvent mixture. The hexane/ethanol/lipid mixture is removed by decanting and the residual solvents are then evaporated, leaving the mycelia as a dry powder.

The solid product has the following basic properties (properties may vary as a function of feed ingredient and culture conditions):

| | |
|---|---|
| Crude protein | 26.9% |
| Carbohydrate | 30.05% |
| Crude fiber | 30.2% |
| Crude fat | 1.75% |

-continued

|  |  |
|---|---|
| Moisture | 8.11% |
| Ash | 2.5% |

Proteins are composed of amino acids. The amino acid composition of the product is as follows (properties may vary as a function of feed ingredient and culture conditions):

|  |  |
|---|---|
| L-Aspartic Acid | 2.15% |
| L-Threonine | 1.29% |
| L-Serine | 1.51% |
| L-Glutamic Acid | 5.09% |
| Glycine | 2.73% |
| L-Alanine | 4.38% |
| L-Valine | 2.15% |
| L-Cysteine | 0.07% |
| L-Methionine | 0.29% |
| L-Isoleucine | 0.79% |
| L-Leucine | 2.15% |
| L-Tyrosine | 0.36% |
| L-Phenylalanine | 0.50% |
| L-Lysine | 1.22% |
| L-Histidine | 0.14% |
| L-Arginine | 0.79% |
| L-Proline | 1.29% |

Example 5

Culture of MM-P1 in a Bioprocess Reactor

MM-P1 is grown in a bioprocess reactor as a submerged, stirred culture in an aqueous medium as follows. A liquid medium in a bioprocess reactor is prepared. The liquid medium contains a carbon source at a concentration of 15.8 g of carbon (atom) per liter. The liquid medium additionally contains yeast extract which comprises additional carbon. The ratio of carbon to nitrogen in the liquid medium is in the range of about 20:1 to about 100:1. Mineral additives as set forth in the table below are added to the liquid medium. Half of the specified amount of each mineral in the table is added initially, and the rest is added as a concentrated solution by sterile transfer 48 hours after onset of growth. Additionally, Tween80 is added.

| Ingredient | Formula | Molecular weight of molecule (g/mol) |
|---|---|---|
| Yeast Extract |  |  |
| Magnesium Sulfate | $MgSO_4 \cdot 7H_2O$ | 246.48 |
| Boric acid | $H_3BO_3$ | 61.83 |
| Manganese chloride | $MnCl_2 \cdot 4H_2O$ | 197.91 |
| Zinc sulfate | $ZnSO_4 \cdot 7H_2O$ | 287.54 |
| Sodium molybdate | $Na_2MoO_4 \cdot 2H_2O$ | 241.97 |
| Copper sulfate | $CuSO_4 \cdot 5H_2O$ | 249.68 |
| Cobalt nitrate | $Co(NO_3)_2 \cdot 6H_2O$ | 291.03 |
| Sodium Acetate | $C_2H_3NaO_2 \cdot 3H_2O$ | 136.08 |
| Potassium Sulfate | $K_2SO_4$ | 174.25 |
| Calcium Chloride | $CaCl_2 \cdot 2H_2O$ | 147.01 |
| Ferric Citrate | $C_6H_8O_7Fe \cdot xH_2O$ | 244.95 |
| Ammonium Phosphate | $(NH_4)_2HPO_4$ | 132.06 |

The liquid culture medium is then sterilized by high temperature (121-124° C.), high pressure, (15-17 PSI). The medium is then cooled to 37° C.

The sterile culture medium is then inoculated with spores (~500 to 1000 viable spores per ml final concentration). The culture is grown at 36-39° C. with a sterile oxygen-enriched sparge (~90 liters per minute of 80% oxygen) and agitation at a stir rate of 60 RPM with a marine blade type impeller. The pH is maintained at 5.5 or above by addition of sterile potassium hydroxide using feedback-controlled automated base addition.

After 48 hours of growth, the remaining mineral additives are added to the culture. After 96 hours of growth, $MgSO_4$ is added to obtain a final concentration of 50 mM.

Following 6 days of culture, the organism is harvested by separating out the biomass from the conditioned culture medium.

Example 6

Animal Meal Tailored for Prawns and Other Aquaculture Species

Fungal biomass can function as an animal feed by itself, but its properties can be enhanced by combining it with other nutrition sources. One example is provided in the case of prawn aquaculture, where the fungal biomass has been combined with other material to improve prawn survivability and weight gain. The following Table lists a variety of compositions that have been developed with fungal biomass and tested on Pacific white shrimp, which is actually a prawn, *Litopenaeus vannamei*.

Biomeal Incorporated Into Prawn Feed

| Ingredient | B % | C % | D % | E % | F % | G % |
|---|---|---|---|---|---|---|
| Biomeal | 0.00 | 3.00 | 6.00 | 9.00 | 12.00 | 15.00 |
| Soybean meal, 45% | 31.43 | 32.22 | 33.01 | 33.81 | 34.60 | 34.32 |
| Wheat flour | 25.00 | 25.00 | 25.00 | 25.00 | 25.00 | 25.00 |
| Feed peas | 18.15 | 14.39 | 10.64 | 6.89 | 3.14 | 0.00 |
| Fishmeal, Herring | 10.00 | 10.00 | 10.00 | 10.00 | 10.00 | 10.00 |
| Wheat gluten | 5.00 | 5.00 | 5.00 | 5.00 | 5.00 | 5.00 |
| Squid meal | 2.50 | 2.50 | 2.50 | 2.50 | 2.50 | 2.50 |
| Krill | 2.50 | 2.50 | 2.50 | 2.50 | 2.50 | 2.50 |
| Fish oil, 999 | 2.44 | 2.43 | 2.43 | 2.43 | 2.42 | 2.38 |
| Lecithin, Deoiled | 1.46 | 1.46 | 1.46 | 1.46 | 1.46 | 1.44 |
| Mono calcium phosphate | 1.28 | 1.25 | 1.22 | 1.18 | 1.15 | 1.09 |
| Rovimix 2050 (Vitamin Mineral Premix) | 0.20 | 0.20 | 0.20 | 0.20 | 0.20 | 0.20 |
| Cholesterol | 0.05 | 0.05 | 0.05 | 0.04 | 0.04 | 0.04 |

All diets, above, have 35% crude protein and 6.5-6.7% crude fat, with increasing crude fiber 1 to r (3.1 to 6.3%)

The Table above lists the fungal biomass as "Biomeal". A range of compositions was studied, ranging from zero to 15% fungal biomass, where it was used to progressively substitute for feed pea meal, which is a standard shrimp and prawn feed ingredient. The substitution was used to maintain protein and fat content within industry standard specifications.

The feed formulations of the Table above were fed to batches of Pacific white shrimp in separate tanks, in batches of 35 prawns per tank. Prawns were periodically removed from the tank and weighed, and mortality was monitored, over a six-week trial period. One tank of prawns was fed a premium commercial feed (designated as "control CP" in the Table below). Weight gain and survival was measured for all formulations and is presented in the Table below. In the table below, "SGR" refers to specific growth rate, and "ADG" refers to average daily weight gain.

| Diets | Initial weight (g) | Weight week 3 (g) | Final weight week 6 (g) | Weight gain (%) | SGR (%/day) | ADG (g/day) | Survival rate (%) |
|---|---|---|---|---|---|---|---|
| Control CP | 1.35 ± 0.23 a | 2.55 ± 1.05 a | 4.66 ± 2.41 a | 245.13 ± 28.48 a | 2.94 ± 0.20 a | 0.08 ± 0.01 a | 80.00 ± 6.17 b |
| BM 0% | 1.35 ± 0.22 a | 2.34 ± 0.78 a | 3.61 ± 1.47 b | 169.00 ± 21.62 b | 2.35 ± 0.19 b | 0.05 ± 0.01 b | 80.00 ± 4.67 b |
| BM 3% | 1.35 ± 0.22 a | 2.47 ± 0.77 a | 3.91 ± 1.40 b | 190.61 ± 16.53 b | 2.54 ± 0.13 b | 0.06 ± 0.01 b | 84.29 ± 5.95 ab |
| BM 6% | 1.35 ± 0.22 a | 2.44 ± 0.77 a | 4.03 ± 1.53 b | 202.64 ± 31.67 b | 2.63 ± 0.25 b | 0.06 ± 0.01 b | 80.00 ± 7.00 b |
| BM 9% | 1.35 ± 0.23 a | 2.46 ± 0.79 a | 3.87 ± 1.64 b | 187.94 ± 32.81 b | 2.51 ± 0.26 b | 0.06 ± 0.01 b | 89.29 ± 3.60 a |
| BM 12% | 1.35 ± 0.22 a | 2.50 ± 0.71 a | 3.99 ± 1.36 b | 197.73 ± 17.49 b | 2.59 ± 0.14 b | 0.06 ± 0.01 b | 90.00 ± 5.47 a |
| BM 15% | 1.35 ± 0.23 a | 2.38 ± 0.71 a | 3.77 ± 1.36 b | 180.75 ± 20.47 b | 2.45 ± 0.18 b | 0.06 ± 0.01 b | 85.71 ± 2.33 ab |

The designations "a" and "b" in the above Table indicate outcomes that are different in a statistically significant manner. The designation "ab" indicates an outcome that is not statistically distinguishable from either outcome "a" or outcome "b". Data were analyzed using Analysis of Variance (ANOVA) and Duncan's New Multiple Range Tests to determine whether significant differences existed between population means. All statistical analyses were conducted using SPSS for Windows, version 15.0. The Table shows that the prawn weight gain from samples B through G was statistically distinguishable from that of the commercial feed, being less. This is likely attributable to the fact that the commercial feed was available in a range of pellet sizes, small sizes being more easily consumed by smaller prawns earlier in the experiment, while the experimental samples B through G were only made in a single, large, size. The larger pellets being less easily consumed by the younger prawns accounts for the difference in weight gain, so that a repeated test with properly sized pellets will eliminate the difference in weight outcome.

The results for survival rate are, however, different. In this case, samples E and F exhibited a higher survival rate that is statistically significant, compared to both the commercial feed and the formulations of samples B and D. This is considered by aquaculture experts to be highly unusual and significant, and indicates that feed formulations incorporating the fungal biomass are, in fact, superior to existing premium feeds.

The prawn example presented above is intended only to be exemplary and not as limiting the detailed formulations of feeds incorporating fungal biomass, nor the range of aquatic or terrestrial animals for which it may be used.

Example 7

Mixture of Whey with MM-P1 Fungal-Cell Biomeal

Overview: an experiment has verified that mixing whey with fungal-cell biomeal yields an animal feed with good nutritional properties that can be pumped as a fluid slurry.

Dried fungal cells, after extraction of TAG, measured 1 kg. Their dietary composition was essentially similar to the cells of Example 2. They were combined with 4 liters of whey provided by Cantare Foods, a cheese producer based in San Diego, Calif. The components of the whey were measured to be as given in the following Table.

Cantaré Foods Whey Sample

| Component | As sent | Dry wt. |
|---|---|---|
| Moisture (vacuum oven) 70 C. (%) | 94.48 | ///// |
| Dry Matter (%) | 5.52 | ///// |
| Crude Protein (%) | 0.4 | 7.32 |
| Phosphorus (%) | 0.04 | 0.67 |
| Calcium (%) | 0.04 | 0.72 |

-continued

| Component | As sent | Dry wt. |
|---|---|---|
| Salt-NaCl (%) | 0.28 | 5.08 |
| Chloride (%) | 0.17 | 3.08 |
| Glucose (%) | <0.1 | |
| Fructose (% sugar) | <0.1 | |
| Sucrose (% sugar) | <0.1 | |
| Maltose (% sugar) | <0.1 | |
| Lactose (% sugar) | 4.4 | |

The general composition of whey is provided in the following Table.

General Composition of Fresh Whey

| S.No | Constituent | Unit | Sweet whey | Acid whey |
|---|---|---|---|---|
| 1 | Water | % | 93-94 | 94-95 |
| 2 | Dry matter | % | 6-6.5 | 5-6 |
| 3 | Lactose | % | 4.4-5 | 3.8-4.4 |
| 4 | Lactic acid | % | traces | up to 0.8 |
| 5 | Total protein | % | 0.8-1.0 | 0.8-1.0 |
| 6 | Whey protein | % | 0.6-0.65 | 0.6-0.65 |
| 7 | Citric acid | % | 0.1 | 0.1 |
| 8 | Minerals | % | 0.5-0.7 | 0.5-0.7 |
| 9 | pH | | 6.4-6.2 | 5.0-4.6 |
| 10 | SH Value | | about 4 | 20-25 |

The resulting mixture contained nutritional components listed in the following Table. The mixture proved easy to pour and pump.

Whey Sample—Biomeal

| Component | As sent | Dry wt. |
|---|---|---|
| Moisture (vacuum oven) 70 C. (%) | 74.36 | ///// |
| Dry Matter (%) | 25.64 | ///// |
| Crude Protein (%) | 3.24 | 12.6 |
| Acid hydrolysis fat (%) | 2.61 | 10.2 |
| Acid detergent fiber (%) | 2.96 | 11.6 |
| Ash (%) | 1.65 | 6.44 |
| Total digestible nutrients (%) | 23 | 89.6 |
| Net energy-lactation (Mcal/lb) | 0.24 | 0.94 |
| Net energy-maint. (Mcal/lb) | 0.25 | 0.99 |
| Net energy-gain (Mcal/lb) | 0.17 | 0.65 |
| Digestible energy (Mcal/lb) | 0.46 | 1.79 |
| Metabolizable energy (Mcal/lb) | 0.43 | 1.67 |

The following table describes the nutrient composition in various biomeal:whey combinations.

Whey Sample—Biomeal

| | Component | | | | | | | | | | | |
|---|---|---|---|---|---|---|---|---|---|---|---|---|
| | Whey Sample alone | | 1:3 (Biomeal:Whey) | | 1:5 (Biomeal:Whey) | | 1:7 (Biomeal:Whey) | | 1:10 (Biomeal:Whey) | | 1:7 (Biomeal:hot Whey, 70° C.) | |
| Moisture (vacuum oven) 70 C. (%) | As sent | Dry wt. | As sent | Dry wt. | As sent | Dry wt. | As sent | Dry wt. | As sent | Dry wt. | As sent | Dry wt. |
| Dry Matter (%) | 94.48 | ///// | 74.36 | ///// | 80.57 | ///// | 83.37 | ///// | 86.81 | ///// | 82.77 | ///// |
| Crude Protein (%) | 5.52 | ///// | 25.64 | ///// | 19.43 | ///// | 16.63 | ///// | 13.19 | ///// | 17.23 | ///// |
| Acid hydrolysis fat (%) | 0.4 | 7.32 | 3.24 | 12.6 | 2.23 | 11.5 | 1.78 | 10.7 | 1.26 | 9.58 | 2.1 | 12.2 |
| Acid detergent fiber (%) | 0.04 | 0.67 | 2.61 | 10.2 | 2.76 | 14.2 | 1.76 | 10.6 | 2.05 | 15.6 | 1.76 | 10.2 |
| Ash (%) | 0.04 | 0.72 | 2.96 | 11.6 | 3.7 | 19.1 | 2.86 | 17.2 | 3.89 | 29.5 | 3.14 | 18.2 |
| Total digestible nutrients (%) | 0.28 | 5.08 | 1.65 | 6.44 | 0.97 | 4.98 | 0.62 | 3.72 | 0.61 | 4.66 | 0.87 | 5.07 |
| Net energy-lactation (Mcal/lb) | 0.17 | 3.08 | 23 | 89.6 | 18.1 | 93.1 | 15.1 | 91 | 12.1 | 91.9 | 15.3 | 88.8 |
| Net energy-maint. (Mcal/lb) | <0.1 | | 0.24 | 0.94 | 0.19 | 0.98 | 0.16 | 0.96 | 0.13 | 0.97 | 0.16 | 0.93 |
| Net energy-gain (Mcal/lb) | <0.1 | | 0.25 | 0.99 | 0.2 | 1.03 | 0.17 | 1.01 | 0.13 | 1.02 | 0.17 | 0.98 |
| Digestible energy (Mcal/lb) | <0.1 | | 0.17 | 0.65 | 0.13 | 0.68 | 0.11 | 0.66 | 0.09 | 0.67 | 0.11 | 0.65 |
| Metabolizable energy (Mcal/lb) | <0.1 | | 0.46 | 1.79 | 0.36 | 1.86 | 0.3 | 1.82 | 0.24 | 1.84 | 0.31 | 1.78 |
| Moisture (vacuum oven) 70 C. (%) | 4.4 | | 0.43 | 1.67 | 0.34 | 1.74 | 0.28 | 1.71 | 0.23 | 1.73 | 0.29 | 1.66 |

Example 8

Mixture of Whey with MM-P1 Fungal-Cell Biomeal for Dairy Cattle

Dried MM-P1 fungal cells, after extraction of TAG, are combined with whey provided a cheese producer, in a ratio of 1 L fungal biomass to 4 L whey, forming a slurry. The slurry is pumped into an empty milk tanker truck. The tanker truck transports the slurry to a dairy farm, where the slurry is pumped to a storage tank for animal feeding. Dairy cattle at the farm are fed the slurry. The empty tanker truck is ready to be filled with milk for the return truck to the cheese producer.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. For example, while the feedstock received by a cellulose processing plant has been referred to as containing cellulosic material, any type of feedstock which may yield alkanes and/or aromatic compounds may be used. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. An admixture for animal feed comprising:
   fungal biomass comprising a cellulose degrading fungus, wherein said fungus is a species being the same as NRRL deposit Accession No: 50410, and
   animal feed providing additional nutrition,
   wherein the wherein the composition comprises 1% to 90% fungal biomass by weight, and wherein the admixture does not contain whey.

2. The admixture of claim 1, wherein the admixture comprises 5% to 20% fungal biomass by weight.

3. The admixture of claim 1, wherein said fungal biomass has been substantially depleted of a lipid product.

4. The admixture of claim 1, wherein the fungal biomass is a product of aerobic fermentation of a feedstock comprising biological matter.

5. The admixture of claim 4, wherein the biological matter comprises at least one of: simple sugars, cane juice or its condensates or its dry solid evaporate, whey, grains, stover, forage, grasses, oilseed crops, nut shells, nut hulls, fruit pomace, plant waste, algae, wood, wood byproducts, bark, paper, paper products, animal manure, food waste, yard waste, almond hulls, grape pomace, agriculture waste, sawdust.

6. The admixture of claim 4, wherein the biological matter comprises at least one of: a cellulosic carbon source or a lysate or a hydrolysate thereof, a hemicellulosic carbon source or a lysate or a hydrolysate thereof, and a lignocellulosic carbon source or a lysate or a hydrolysate thereof.

7. The admixture of claim 1, wherein the fungal biomass comprises greater than 25% cell dry weight (cdw) crude protein.

8. The admixture of claim 1, wherein the fungal biomass comprises 5% to 50% of the admixture by weight.

9. The admixture of claim 1, wherein the fungal biomass comprises at least 10% (cdw) lipid comprising triacylglycerol (TAG).

10. The admixture of claim 1, wherein the fungal biomass comprises mycelial residue following extraction of lipids.

11. The admixture of claim 10, wherein the lipids comprise at least one of: TAG, wax esters, mono-unsaturated hydrocarbon chains, di-unsaturated hydrocarbon chains, and any molecular forms having a straight-chain saturated hydrocarbon portion.

12. The admixture of claim 1, wherein the fungal biomass comprises biomass harvested at a particular time to optimize production of a non-lipid portion of the biomass, the particular time being either a time that an available nitrogen ingredient is exhausted, or a time when log-phase growth terminates.

13. The admixture of claim 1, wherein the fungal biomass comprises 25% to 75% (cdw) crude protein.

14. The admixture of claim 1, wherein the fungal biomass comprises 50% and 90% of the admixture by weight.

15. The admixture of claim 1, wherein the admixture is in the form of a pellet.

16. The admixture of claim 1, wherein the admixture is in the form of a slurry.

17. The admixture of claim 1, wherein the fungal biomass is a dried fungal biomass that is a product of fermentation of a feedstock with said fungus in a liquid culture.

18. The admixture of claim 17, wherein the admixture is produced by a product of combining the dried fungal biomass with said animal feed.

19. The admixture of claim 1, wherein the animal feed is formulated for an aquatic animal.

20. The admixture of claim 1, wherein the animal feed is formulated for a terrestrial animal.

* * * * *